(12) United States Patent
Taniguchi et al.

(10) Patent No.: US 9,150,588 B2
(45) Date of Patent: *Oct. 6, 2015

(54) SUBSTITUTED PYRIDAZIN-4(1H)-ONES AS PHOSPHODIESTERASE 10A INHIBITORS

(75) Inventors: Takahiko Taniguchi, Kanagawa (JP);
Masato Yoshikawa, Kanagawa (JP);
Tomoaki Hasui, Kanagawa (JP);
Makoto Fushimi, Kanagawa (JP); Jun Kunitomo, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/816,011

(22) PCT Filed: Aug. 9, 2011

(86) PCT No.: PCT/JP2011/068205
§ 371 (c)(1),
(2), (4) Date: Feb. 8, 2013

(87) PCT Pub. No.: WO2012/020780
PCT Pub. Date: Feb. 16, 2012

(65) Prior Publication Data
US 2013/0137675 A1 May 30, 2013

(30) Foreign Application Priority Data
Aug. 10, 2010 (JP) ................ 2010-179430

(51) Int. Cl.
A61K 31/501 (2006.01)
C07D 403/04 (2006.01)
(Continued)

(52) U.S. Cl.
CPC ............ C07D 498/04 (2013.01); C07D 401/04 (2013.01); C07D 401/14 (2013.01);
(Continued)

(58) Field of Classification Search
CPC ....................... A61K 31/501; C07D 403/04
USPC ............... 514/247; 544/238; 546/210, 268.1; 548/373.1
See application file for complete search history.

(56) References Cited

U.S. PATENT DOCUMENTS

2005/0075372 A1 4/2005 Lahm et al.
2009/0163545 A1 6/2009 Goldfarb
(Continued)

FOREIGN PATENT DOCUMENTS

JP 2004-538327 12/2004
WO 02/48115 6/2002
(Continued)

OTHER PUBLICATIONS

International Search Report issued Sep. 27, 2011 in corresponding International (PCT) Application No. PCT/JP2011/068205.
(Continued)

Primary Examiner — Douglas M Willis
(74) Attorney, Agent, or Firm — Wenderoth, Lind & Ponack, L.L.P.

(57) ABSTRACT

A compound having PDE inhibitory represented by formula (1), $W^1$-$W^2$ (1), wherein (i) $W^1$ is

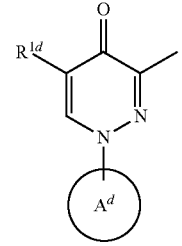

and $W^2$ is

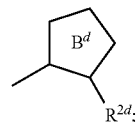

(ii) $W^1$ is

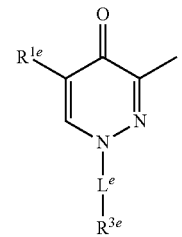

and $W^2$ is

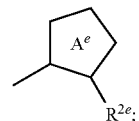

or (iii) $W^1$ is

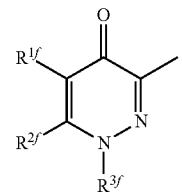

and $W^2$ is

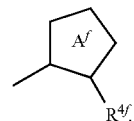

or a pharmaceutically acceptable salt thereof; and a method of treating or preventing schizophrenia.

9 Claims, No Drawings

(51) Int. Cl.

| | | |
|---|---|---|
| *C07D 498/04* | (2006.01) | |
| *C07D 401/04* | (2006.01) | |
| *C07D 403/14* | (2006.01) | |
| *C07D 405/04* | (2006.01) | |
| *C07D 405/14* | (2006.01) | |
| *C07D 409/14* | (2006.01) | |
| *C07D 417/14* | (2006.01) | |
| *C07D 491/048* | (2006.01) | |
| *C07D 401/14* | (2006.01) | |
| *C07D 409/04* | (2006.01) | |
| *C07D 413/14* | (2006.01) | |

(52) U.S. Cl.
CPC ............ *C07D403/04* (2013.01); *C07D 403/14* (2013.01); *C07D 405/04* (2013.01); *C07D 405/14* (2013.01); *C07D 409/04* (2013.01); *C07D 409/14* (2013.01); *C07D 413/14* (2013.01); *C07D 417/14* (2013.01); *C07D 491/048* (2013.01)

(56) References Cited

U.S. PATENT DOCUMENTS

| | | |
|---|---|---|
| 2010/0152193 A1 | 6/2010 | Alberati et al. |
| 2010/0197651 A1 | 8/2010 | Taniguchi et al. |
| 2010/0216793 A1 | 8/2010 | Alberati et al. |
| 2011/0144115 A1 | 6/2011 | Vernhet et al. |
| 2012/0028951 A1 | 2/2012 | Taniguchi et al. |
| 2012/0277204 A1 | 11/2012 | Taniguchi et al. |
| 2012/0277430 A1 | 11/2012 | Taniguchi et al. |
| 2012/0277431 A1 | 11/2012 | Taniguchi et al. |

FOREIGN PATENT DOCUMENTS

| | | |
|---|---|---|
| WO | 03/015518 | 2/2003 |
| WO | 2006/072828 | 7/2006 |
| WO | 2008/001182 | 1/2008 |
| WO | 2008/004117 | 1/2008 |
| WO | 2008/030158 | 3/2008 |
| WO | 2010/004215 | 1/2010 |
| WO | 2010/057121 | 5/2010 |
| WO | 2010/057126 | 5/2010 |
| WO | 2010/063610 | 6/2010 |
| WO | 2010/090737 | 8/2010 |
| WO | 2010/094009 | 8/2010 |
| WO | 2010/094762 | 8/2010 |
| WO | 2010/123716 | 10/2010 |
| WO | 2012/018058 | 2/2012 |
| WO | 2012/018059 | 2/2012 |

OTHER PUBLICATIONS

STN Online Caplus File AN=2002:487243, RN=220206-01-9, 371155-03-2, 246029-45-8, 474977-01-0, 2002.

STN Online Caplus File AN=2006:690333, RN=934356-38-4, 2006.

Christopher D. Smith et al.; "Synthesis of Linked Heterocycles Via Use of Bis-Acetylenic Compounds"; Tetrahedron Letters; 2006; 47(19); p. 3209-3212.

Frank S. Menniti et al.; "Phosphodiesterases in the CNS: Targets for Drug Development"; Nature Reviews—Drug Discovery; 2006; vol. 5; p. 660-670.

Miles D. Houslay et al.; "cAMP-Specific Phosphodiesterase-4 Enzymes in the Cardiovascular System: A Molecular Toolbox for Generating Compartmentalized cAMP Signaling"; Circulation Research, Journal of the American Heart Association; 2007; vol. 100(7); p. 950-966.

Jun Nakayama et al.; "Expression Cloning of a Human $\alpha$1,4-N-acetylglucosaminyltransferase that Forms GlcNAc$\alpha$1→4Gal$\beta$→R, a Glycan Specifically Expressed in the Gastric Gland Mucous Cell-Type Mucin"; Proc. Natl. Acad. Sci. USA; 1999; vol. 96; p. 8991-8996.

Kotomi Fujishige et al.; "Cloning and Characterization of a Novel Human Phosphodiesterase that Hydrolizes Both cAMP and cGMP (PDE10A)"; The Journal of Biological Chemistry; 1999; vol. 274; p. 18428-18445.

K. Loughney et al.; "Isolation and Characterization of PDE10A, a Novel Human 3', 5'-Cyclic Nucelotide Phosphodiesterase"; GENE, an International Journal on Genes and Genomes; 1999; vol. 234; p. 109-117.

Kotomi Fujishige et al.; "Striatum- and Testis-Specific Phosphodisterase PDE10A; Isolation and Characterization of a Rat PDE10A"; European Journal of Biochemistry; 1999; vol. 266; p. 1118-1127.

Thomas F. Seeger et al.; "Immunohistochemical localization of PDE10A in the Rat Brain"; Brain Research; 2003; vol. 985; p. 113-126.

Yoshihisa Kurasawa et al., "Quinolone Analogues 7 [1-6]. Synthesis of 3-Heteroaryl-1-methylpyridazino[3,4-*b*]quinoxalin-4(1*H*)-ones", Journal of Heterocyclic Chemistry, 2005, vol. 42, No. 2, pp. 249-254.

SUBSTITUTED PYRIDAZIN-4(1H)-ONES AS PHOSPHODIESTERASE 10A INHIBITORS

TECHNICAL FIELD

The present invention relates to a novel heterocyclic compound, a production method thereof and a medicament containing same and the like. More particularly, the present invention relates to a compound having an inhibitory action on phosphodiesterase 10A and effective as a medicament for the prophylaxis or treatment of mental diseases such as schizophrenia and the like, and the like.

BACKGROUND OF THE INVENTION

Phosphodiesterase (PDE) is an enzyme that hydrolyzes cAMP and cGMP that function as intracellular second messengers into 5'-AMP and 5'-GMP, respectively. PDE gene is constituted with 21 genes, and currently classified into 11 kinds of families based on the molecular structure of the enzymes. Furthermore, each PDE is classified into the following 3 kinds: 1) cAMP-PDEs (PDE4, PDE7, PDE8), 2) cGMP-PDE (PDE5, PDE6, PDE9), and 3) dual-substrate PDEs (PDE1, PDE2, PDE3, PDE10, PDE11), based on the substrate specificity.

cAMP and cGMP are involved in various physiological functions such as control of ion channel, muscle relaxation, learning and memory function, differentiation, apoptosis, lipogenesis, glycogenolysis and gluconeogenesis. Particularly, they are known to play an important role in the differentiation and survival, as well as control of neurotransmission of the nerve cell (non-patent document 1). Phosphorylation of various molecules that control physiological functions such as transcription factors ion channel and receptor, which is caused by protein kinase A (PKA) and protein kinase G (PKG), contributes to such control by cAMP and cGMP, and the amounts of cAMP and cGMP in the cell are under spatiotemporal regulation via generation by adenylate cyclase and guanylate cyclase in response to extracellular stimulations and degradation thereof by PDE (non-patent document 2). Since PDE is a sole enzyme that decomposes cAMP and cGMP in vivo, PDE is considered to play an important role in the regulation of cyclic nucleotide signaling.

PDE10A is a molecule cloned by 3 independent groups and reported in 1999 (non-patent documents 3, 4). Expression analysis thereof has clarified that PDE10A shows high expression only in the brain and testis, and has a localized expression pattern in the PDE family (non-patent documents 5, 6). In the brain, both PDE10A mRNA and PDE10A protein show high expression in medium spiny nerve cells of the striatum (medium spiny neurons, MSNs) (non-patent documents 7, 8). MSNs are classified as two major kinds of pathways. One of them is called a direct pathway or nigrostriatal pathway, and mainly expresses dopamine $D_1$ receptors. The other pathway, indirect pathway, is called a striatum-globus pallidus pathway, and mainly expresses dopamine $D_2$ receptors. The direct pathway is involved in the functions of motion execution and reward learning and, on the other hand, the indirect pathway is involved in the suppression of motility. The activity of the output nucleus of the basal nucleus is regulated by the balance of antagonistic inputs from these two kinds of pathways. Since PDE10A is expressed in MSNs of both pathways, the both pathways are considered to be activated by inhibition of PDE10A. Since the action of existing antipsychotic agents having a $D_2$ receptor shutting off action is mainly mediated by the activation of indirect pathway, a PDE10A inhibitor is expected to show an anti-mental disease action like existing drugs.

The excess $D_2$ receptor shutting off action in the brain by existing drugs causes side effects such as hyperprolactinemia and extrapyramidal syndrome. However, since PDE10A shows striatum pathway specific expression and shows a lower expression level in the pituitary gland mainly involved in the prolactin release, PDE10A inhibitor is considered to have no prolactin concentration increasing action in plasma. Moreover, since PDE10A is also expressed in the direct pathway MSNs and activated by a PDE10A inhibitor, it is considered to have superior characteristics than existing antipsychotic agents that activate only indirect pathways. That is, since the direct pathway is involved in the motion execution, it is considered to antagonistically act against extrapyramidal syndrome caused by excessive activation of indirect pathway. Furthermore, this pathway is expected to show actions to enhance the output from the striatum-thalamus circuit and promote cognitive functions of reward learning and problem solving. Since existing antipsychotic agents show a shutting off action on many receptors, they pose problems of side effects such as body weight increase and abnormal metabolism. PDE10A inhibitor is also considered to be superior to the existing drugs in the side effects, since it directly activates second messenger signaling without blocking dopamine and/or other neurotransmitter receptors. In view of the specific expression and its function in the brain nerve system, PDE10A is considered to be useful as a drug discovery target in neurological diseases, in particular, mental diseases such as schizophrenia.

Patent document 1 discloses, as a PDE10A inhibitor, a compound of the following formula:

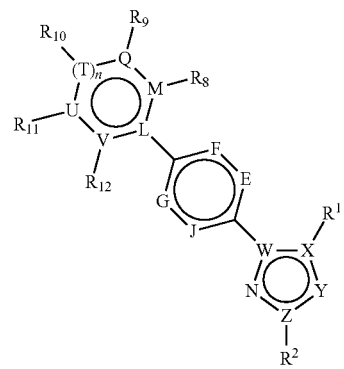

(the definition of each symbol is as described in patent document 1),
and the following compounds

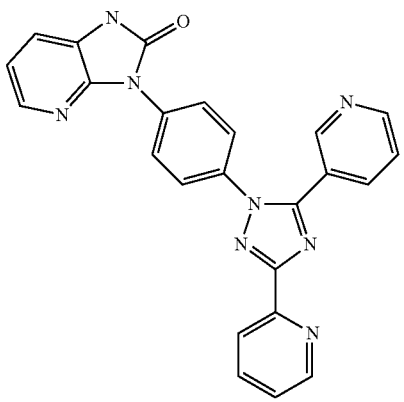

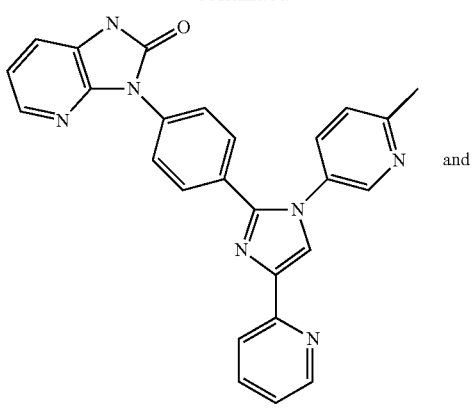

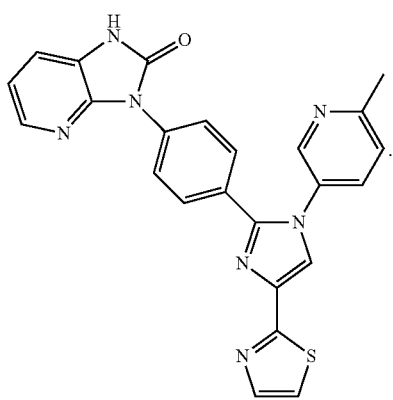

Patent document 2 discloses, as a PDE10A inhibitor, a compound of the following formula:

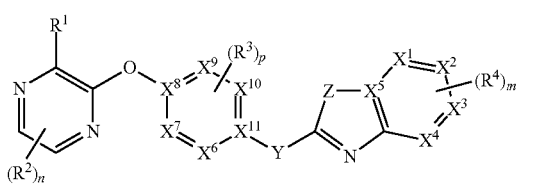

(the definition of each symbol is as described in patent document 2), and
the following compounds:

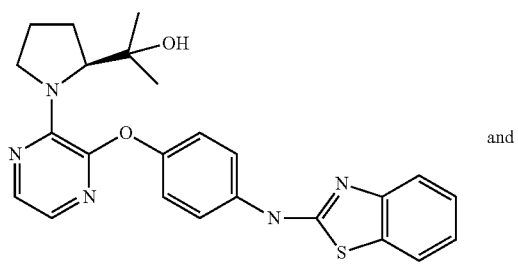

and

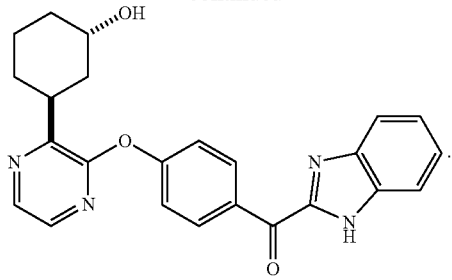

Patent document 3 discloses, as a PDE10A inhibitor, a compound of the following formula:

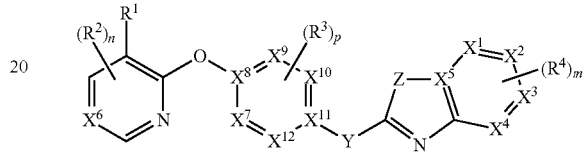

(the definition of each symbol is as described in patent document 3), and
the following compounds:

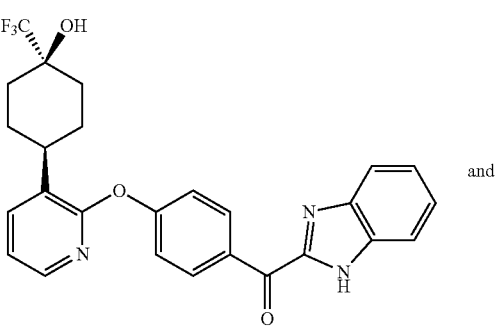

and

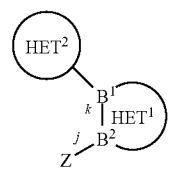

Patent document 4 discloses, as a PDE10A inhibitor, a compound of the following formula:

wherein Z is

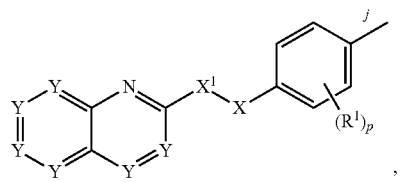

and
the definition of each symbol is as described in patent document 4.

Patent document 5 discloses the following compound as a PDE10A inhibitor.

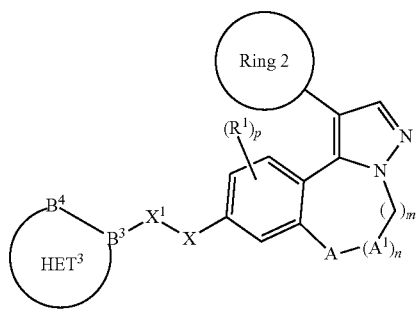

(the definition of each symbol is as described in patent document 5).

Patent document 6 discloses, as a PDE10A inhibitor, a compound of the following formula:

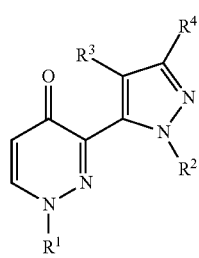

(the definition of each symbol is as described in patent document 6), and
the following compounds:

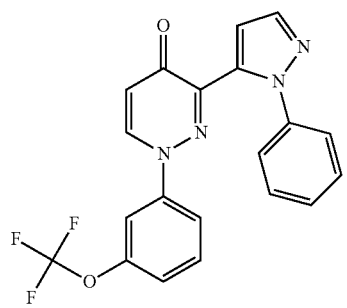 [SMILES: O=c1ccn(-c2cccc(OC(F)(F)F)c2)nc1-c1ccnn1-c1ccccc1]

and

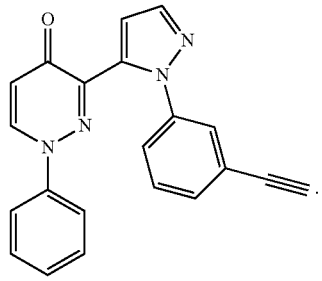 [SMILES: C#Cc1cccc(-n2nccc2-c2nn(-c3ccccc3)ccc2=O)c1]

Patent document 7 discloses lifespan altering compounds represented by

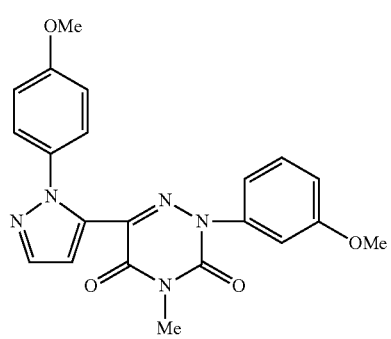

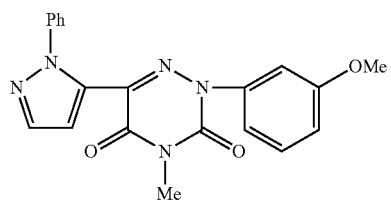

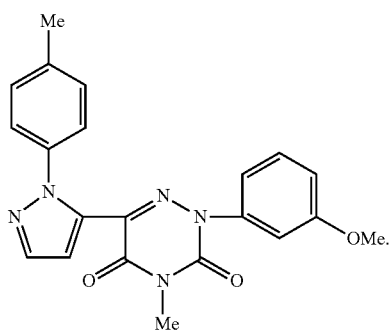

Patent document 8 discloses compounds having a neutrophil elastase inhibitory action and production intermediate compounds therefor, which are represented by

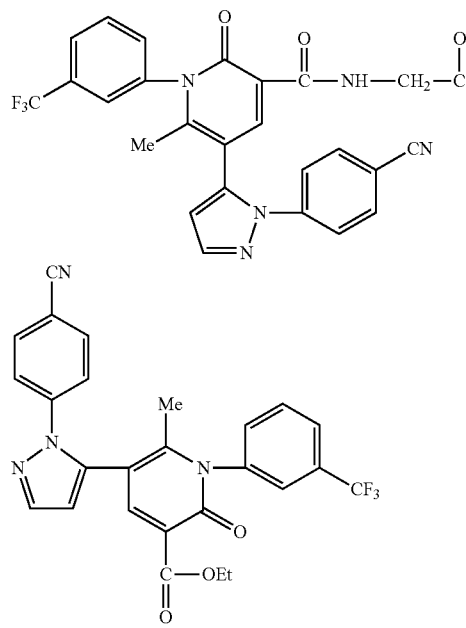
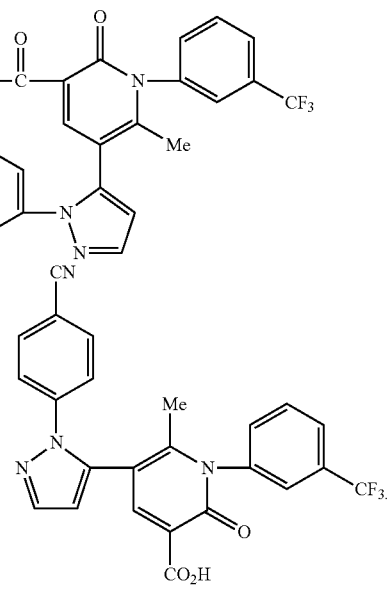

Non-patent document 9 discloses the following compound:

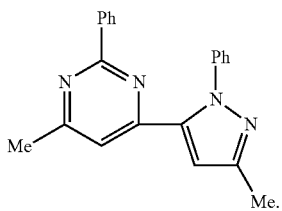 [SMILES: Cc1cc(-c2cc(C)nn2-c2ccccc2)nc(-c2ccccc2)n1]

Patent document 9 discloses, as a PDE10A inhibitor, a compound of the following formula:

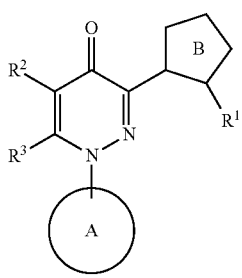

(the definition of each symbol is as described in patent document 9).

DOCUMENT LIST

Patent Documents patent document 1: WO2008/004117
patent document 2: WO2010/057121
patent document 3: WO2010/057126
patent document 4: WO2006/072828
patent document 5: WO2008/001182
patent document 6: WO2010/063610
patent document 7: US 20090163545 A
patent document 8: WO2008/030158
patent document 9: WO2010/090737

Non-Patent Documents non-patent document 1: Nat. Rev. Drug Disc. 2006, vol. 5: 660-670
non-patent document 2: Circ. Res. 2007, vol. 100(7): 950-966
non-patent document 3: Proc. Natl. Acad. Sci. USA 1999, vol. 96: 8991-8996
non-patent document 4: J. Biol. Chem. 1999, vol. 274: 18438-18445, Gene 1999, vol. 234: 109-117
non-patent document 5: Eur. J. Biochem. 1999, vol. 266: 1118-1127
non-patent document 6: J. Biol. Chem. 1999, vol. 274: 18438-18445
non-patent document 7: Eur. J. Biochem. 1999, vol. 266: 1118-1127
non-patent document 8: Brain Res. 2003, vol. 985: 113-126
non-patent document 9: Tetahedron Letters 2006, vol. 47: 3209-3212

SUMMARY OF THE INVENTION

Problems to be Solved by the Invention

The present invention aims to provide a compound having a PDE10A inhibitory action and useful as a prophylactic or therapeutic drug for mental diseases such as schizophrenia and the like.

Means of Solving the Problems

The present inventors discovered that a compound expressed by the formula (1$^x$) or a salt thereof (referred to as compound (1$^x$) in this specification), and a compound expressed by the formula (1) or a salt thereof (referred to as compound (1) in this specification) have a PDE 10A inhibitory action and after extensive investigation, completed the present invention.

In this specification, the compound ($1^x$) or compound (1), or a prodrug thereof is also referred to the compound of the present invention.

Accordingly, the present invention provides

[1] a compound represented by the formula ($1^x$)

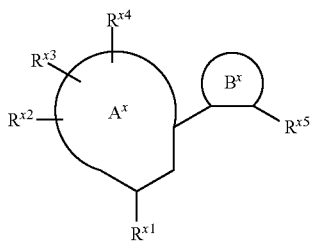

($1^x$)

wherein $R^{x1}$ and $R^{x5}$ are the same or different and each is a substituent, $R^{x2}$, $R^{x3}$ and $R^{x4}$ are the same or different and each is absent, a hydrogen atom or a substituent, ring $A^x$ is a 5- or 6-membered ring optionally further substituted, and ring $B^x$ is a heterocycle optionally further substituted, wherein any two of $R^{x1}$, $R^{x2}$, $R^{x3}$ and $R^{x4}$ are optionally bonded to form, together with ring $A^x$, an optionally substituted bicyclic fused ring, or an optionally substituted tricyclic fused ring, or a salt thereof,

[2] the compound of the above-mentioned [1], which is represented by the formula ($1^{x'}$)

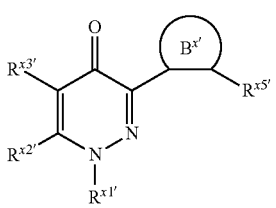

($1^{x'}$)

wherein $R^{x1'}$ and $R^{x5'}$ are substituents, $R^{x2'}$ and $R^{x3'}$ are the same or different and each is a hydrogen atom or a substituent, and ring $B^{x'}$ is a heterocycle optionally further substituted, provided that when $R^{x1'}$ is an optionally substituted aromatic ring, ring $B^{x'}$ is not a 5-membered aromatic heterocycle optionally further substituted, or a salt thereof,

[3] a compound represented by the formula (1)

$$W^1\text{-}W^2 \quad (1)$$

wherein (1) when $W^1$ is

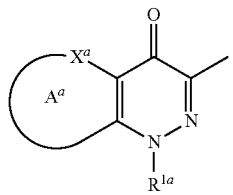

(ring $A^a$ is an optionally substituted 5- to 7-membered heterocycle; $X^a$ is an oxygen atom, a sulfur atom or —$NR^a$— ($R^a$ is a hydrogen atom or a substituent); and $R^{1a}$ is a substituent), $W^2$ is

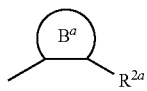

(ring $B^a$ is a nitrogen-containing heterocycle optionally further substituted; and $R^{2a}$ is a substituent), (2) when $W^1$ is

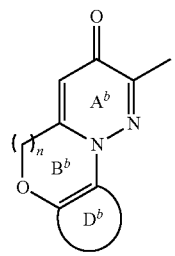

(ring $A^b$ is a ring optionally further substituted; ring $B^b$ is an optionally substituted ring; ring $D^b$ is an optionally substituted 6- to 10-membered aromatic hydrocarbon ring; and n is 0, 1 or 2), $W^2$ is

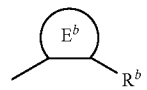

(ring $E^b$ is a 5- to 10-membered aromatic heterocycle optionally further substituted; and $R^b$ is a substituent), (3) when $W^1$ is

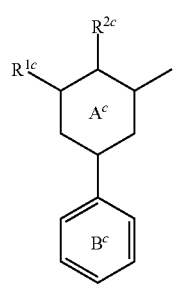

(ring $A^c$ is a 6-membered heterocycle optionally further substituted; ring $B^c$ is an optionally substituted 6-membered aromatic ring; $R^{1c}$ is a hydrogen atom or a substituent (excluding an aromatic ring group and —CO—$R^x$ ($R^x$ is a substituent)); and $R^{2c}$ is a hydrogen atom, a hydroxy group, an oxo group or an optionally substituted $C_{1-6}$ alkoxy group), $W^2$ is

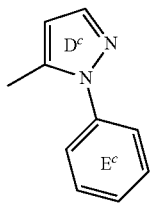

(ring $D^c$ is a pyrazole ring optionally further substituted; and ring $E^c$ is an optionally substituted benzene ring), (4) when $W^1$ is

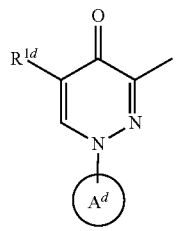

(ring $A^d$ is an optionally substituted 3- to 10-membered non-aromatic ring; and $R^{1d}$ is a hydrogen atom or a $C_{1-6}$ alkoxy group), $W^2$ is

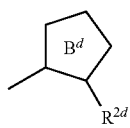

(ring $B^d$ is a 5-membered aromatic heterocycle optionally further substituted; and $R^{2d}$ is a substituent, (5) when $W^1$ is

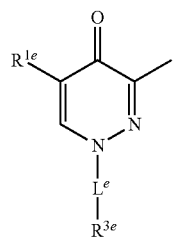

($R^{1e}$ is a $C_{1-6}$ alkoxy group; $R^{3e}$ is an optionally substituted $C_{1-6}$ alkyl group, optionally substituted 3- to 6-membered hydrocarbon ring group, or an optionally substituted 5- to 10-membered heterocyclic group; and $L^e$ is an optionally substituted $C_{1-3}$ alkylene group or a sulfonyl group), $W^2$ is

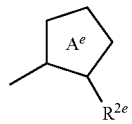

(ring $A^e$ is a 5-membered aromatic heterocycle optionally further substituted; and $R^{2e}$ is a substituent), alternatively, when, in (6), $W^1$ is

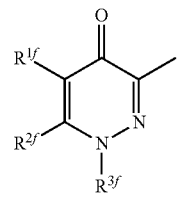

($R^{1f}$ is an optionally substituted $C_{1-6}$ alkoxy group; $R^{2f}$ is a hydrogen atom or a substituent; and $R^{1f}$ is an optionally substituted $C_{1-6}$ alkyl group or an optionally substituted cyclic group), $W^2$ is

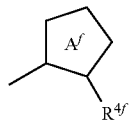

(ring $A^f$ is a non-aromatic 5-membered heterocycle optionally further substituted; and $R^{4f}$ is an optionally substituted $C_{1-6}$ alkyl group or an optionally substituted cyclic group), provided that a compound wherein the partial structural formula for $W^1$

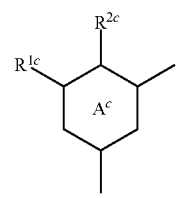

is represented by

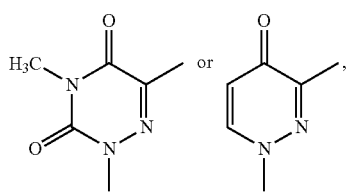

and
4-methyl-6-(3-methyl-1-phenyl-1H-pyrazol-5-yl)-2-phenylpyrimidine are excluded,
or a salt thereof,

[4] 3-(1-phenyl-1H-pyrazol-5-yl)-1-[3-(trifluoromethyl)phenyl]furo[3,2-c]pyridazin-4(1H)-one, or a salt thereof,

[5] 3-(1-phenyl-1H-pyrazol-5-yl)-1-[3-(trifluoromethyl)phenyl]-6,7-dihydrofuro[3,2-c]pyridazin-4(1H)-one, or a salt thereof,

[6] 1-(1-benzyl-1,2,3,6-tetrahydropyridin-4-yl)-5-methoxy-3-(1-phenyl-1H-pyrazol-5-yl)pyridazin-4(1H)-one, or a salt thereof,

[7] 2-{4-[5-methoxy-4-oxo-3-(1-phenyl-1H-pyrazol-5-yl)pyridazin-1(4H)-yl]piperidin-1-yl}pyridine-3-carbonitrile, or a salt thereof,

[8] a medicament comprising the compound or salt of any one of the above-mentioned [1]-[7],

[9] the medicament of the above-mentioned [8], which is a phosphodiesterase 10A inhibitor,

[10] the medicament of the above-mentioned [8], which is for the prophylaxis or treatment of schizophrenia,

[11] a method for preventing or treating schizophrenia, which comprises administering an effective amount of the compound or salt of any one of the above-mentioned [1]-[7] to a mammal,

[12] use of the compound or salt of any one of the above-mentioned [1]-[7] in the manufacture of a medicament for the prophylaxis or treatment of schizophrenia,

[13] the compound of any one of the above-mentioned [1]-[7] or a salt thereof for the prophylaxis or treatment of schizophrenia, and the like.

DETAILED DESCRIPTION OF THE INVENTION

The compound of the present invention has a PDE 10A inhibitory activity and is useful as a drug for preventing or treating schizophrenia, etc.

DESCRIPTION OF EMBODIMENTS

The present invention is explained in detail below.

Unless otherwise specified, in this specification, "optionally further substituted" means that a group optionally has substituent(s) other than those clearly shown in the chemical formula.

Unless otherwise specified, in this specification, examples of the "halogen atom" include fluorine, chlorine, bromine and iodine.

Unless otherwise specified, in this specification, the phrase "optionally halogenated" or the term "halogeno" means that one or more (e.g., 1 to 3) halogen atoms can be present as substituents.

Unless otherwise specified, in this specification, examples of the "alkyl (group)" include $C_{1-6}$ alkyl (group).

Unless otherwise specified, in this specification, examples of the "$C_{1-6}$ alkyl (group)" include methyl, ethyl, propyl, isopropyl, butyl, isobutyl, sec-butyl, tert-butyl, pentyl, isopentyl, neopentyl, and hexyl.

Unless otherwise specified, in this specification, the term "optionally halogenated $C_{1-6}$ alkyl (group)" means $C_{1-6}$ alkyl (group) which can be substituted by halogen atom(s), and examples thereof include trifluoromethyl.

Unless otherwise specified, in this specification, examples of the "alkenyl (group)" include $C_{2-6}$ alkenyl (group).

Unless otherwise specified, in this specification, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.

Unless otherwise specified, in this specification, examples of the "alkynyl (group)" include $C_{2-6}$ alkynyl (group). Examples of the "$C_{2-6}$ alkynyl (group)" include ethynyl, 1-propyn-1-yl, 2-propyn-1-yl, 4-pentyn-1-yl, and 5-hexyn-1-yl.

Unless otherwise specified, in this specification, examples of the "$C_{3-7}$ cycloalkyl-$C_{2-6}$ alkynyl (group)" include cyplopropyletynyl.

Unless otherwise specified, in this specification, examples of the "$C_{3-7}$ cycloalkyl (group)" include cyclopropyl, cyclobutyl, cyclopentyl, and cyclohexyl.

Unless otherwise specified, in this specification, examples of the "$C_{6-14}$ aryl (group)" include phenyl, 1-naphthyl, 2-naphthyl, 2-biphenylyl, 3-biphenylyl, 4-biphenylyl, and 2-anthryl.

Unless otherwise specified, in this specification, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

Unless otherwise specified, in this specification, examples of the "$C_{6-14}$ aryl-$C_{2-6}$ alkenyl (group)" include styryl.

Unless otherwise specified, in this specification, examples of the "heterocycle" include a 3- to 8-membered heterocycle containing 1-4 hetero atoms selected from a nitrogen atom, a sulfur atom and an oxygen atom.

Unless otherwise specified, in this specification, examples of the "heterocycle" include a non-aromatic heterocycle, and an aromatic heterocycle can be mentioned.

Unless otherwise specified, in this specification, examples of the "non-aromatic heterocycle" include a 3- to 8-membered non-aromatic heterocycle and the like. Concrete examples thereof include oxirane ring, azetidine ring, oxetane ring, thietane ring, pyrrolidine ring, dihydrofuran ring, tetrahydrofuran ring, tetrahydrothiophene ring, imidazolidine ring, oxazolidine ring, isooxazoline ring, piperidine ring, dihydropyran ring, tetrahydropyran ring, tetrahydrothiopyran ring, morpholine ring, thiomorpholine ring, piperazine ring, dihydrooxazin ring, tetrahydrooxazin ring, dihydropyrimidine ring, tetrahydropyrimidine ring, azepane ring, oxepane ring, thiepane ring, oxazepane ring, thiazepane ring, azocane ring, oxocane ring, thiocane ring, oxazocane ring, and thiazocane ring.

Unless otherwise specified, in this specification, examples of the "aromatic heterocycle" include a 5- or 6-membered aromatic heterocycle. Concrete examples thereof include furan ring, pyran ring, thiopyran ring, thiophene ring, pyrrole ring, oxazole ring, isoxazole ring, thiazole ring, isothiazole ring, imidazole ring, pyrazole ring, 1,2,3-oxadiazole ring, 1,2,4-oxadiazole ring, 1,3,4-oxadiazole ring, furazan ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, dihydropyridazine ring, pyrimidine ring, pyrazine ring, and triazine ring.

Unless otherwise specified, in this specification, examples of the "hydrocarbon ring" include "aromatic hydrocarbon ring", and "non-aromatic hydrocarbon ring".

Unless otherwise specified, in this specification, examples of the "aromatic hydrocarbon ring" include an aromatic hydrocarbon ring having a carbon number of 6-14. Concrete examples thereof include benzene ring, naphthalene ring, anthracene ring, and phenanthrene ring. Unless otherwise specified, the "aromatic hydrocarbon ring" may be monocyclic, bicyclic, or tricyclic.

Unless otherwise specified, in this specification, examples of the "non-aromatic hydrocarbon ring" include a $C_{3-7}$ cycloalkane, a $C_{3-7}$ cycloalkene and a $C_{4-10}$ cycloalkadiene.

Unless otherwise specified, in this specification, examples of the "hydrocarbon ring group" include "aromatic hydrocarbon ring group", and "non-aromatic hydrocarbon ring group".

Unless otherwise specified, in this specification, examples of the "aromatic hydrocarbon ring group" include an aromatic hydrocarbon ring group having a carbon number 6-14. Concrete examples thereof include phenyl group, naphthyl group, anthracenyl group, and phenanthrenyl ring. Unless otherwise specified, the "aromatic hydrocarbon ring group" may be monocyclic, bicyclic, or tricyclic.

Unless otherwise specified, in this specification, examples of the "non-aromatic hydrocarbon ring group" include a $C_{3-7}$ cycloalkyl (group), a $C_{3-7}$ cycloalkenyl (group), and a $C_{4-10}$ cycloalkadienyl (group), each of which may be condensed with one or more (preferably 1 or 2) hydrocarbon rings.

Unless otherwise specified, in this specification, the "heterocyclic group" (and a heterocyclic moiety in a substituent) is a non-aromatic heterocyclic group, or a heteroaryl group (i.e., aromatic heterocyclic group), and examples thereof include a 3- to 14-membered heterocyclic group having 1 to 5 hetero atoms selected from a nitrogen atom, a sulfur atom and an oxygen atom. This "heterocyclic group" can be monocyclic, bicyclic or tricyclic.

Unless otherwise specified, in this specification, examples of the "3- to 14-membered heterocyclic group" include a 3- to 14-membered aromatic heterocyclic group having 1 to 5 hetero atoms selected from a nitrogen atom, a sulfur atom and an oxygen atom such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl), methylenedioxyphenyl and the like; and a saturated or unsaturated 3- to 14-membered non-aromatic heterocyclic group having 1 to 5 hetero atoms selected from a nitrogen atom, a sulfur atom and an oxygen atom such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl and the like.

Unless otherwise specified, in this specification, examples of the "aromatic heterocyclic group" (and the aromatic heterocyclic moiety in a substituent) include the "3- to 14-membered aromatic heterocyclic group having 1 to 5 hetero atoms selected from a nitrogen atom, a sulfur atom and an oxygen atom" as exemplified above as the above-mentioned "heterocyclic group".

Unless otherwise specified, in this specification, examples of the "non-aromatic heterocyclic group" (and the aromatic heterocyclic moiety in a substituent) include the "saturated or unsaturated 3- to 14-membered non-aromatic heterocyclic group having 1 to 5 hetero atoms selected from a nitrogen atom, a sulfur atom and an oxygen atom" as exemplified above as the above-mentioned "heterocyclic group".

Unless otherwise specified, in this specification, examples of the "saturated heterocyclic group" (and the saturated heterocyclic moiety in a substituent) include those saturated among the above-mentioned non-aromatic heterocyclic groups. Specific examples thereof include tetrahydrofuryl, morpholinyl, thiomorpholinyl, piperidinyl, pyrrolidinyl, piperazinyl and the like.

Unless otherwise specified, in this specification, examples of the "5- to 6-membered saturated heterocyclic group" (and the saturated heterocyclic moiety in a substituent) include those having 5- to 6-membered group from among the above-mentioned saturated heterocyclic groups.

Unless otherwise specified, in this specification, examples of the "nitrogen-containing heterocycle" include 3- to 8-membered saturated or unsaturated nitrogen-containing heterocycle containing, as a ring constituting atom besides carbon atom, 1 to 4 nitrogen atoms, and further optionally containing 1 or 2 hetero atoms selected from an oxygen atom and a sulfur atom (said sulfur atom is optionally oxidized). Specific examples include pyrrole, imidazole, pyrazole, triazole, tetrazolylpyridine, pyrazine, pyrimidine, pyridazine, dihydropyridazine, azetidine, pyrrolidine, piperidine, morpholine, thiomorpholine, piperazine, azepane, tetrahydropyrimidine, dihydropyridine, tetrahydropyridine and the like.

Unless otherwise specified, in this specification, examples of the "alkoxy (group)" include $C_{1-6}$ alkoxy (group).

Unless otherwise specified, in this specification, examples of the "$C_{1-6}$ alkoxy (group)" include methoxy, ethoxy, propoxy, isopropoxy, butoxy, isobutoxy, sec-butoxy, pentyloxy and hexyloxy.

Unless otherwise specified, in this specification, examples of the "$C_{3-7}$ cycloalkyloxy (group)" include cyclopropyloxy, cyclobutyloxy, cyclopentyloxy and cyclohexyloxy.

Unless otherwise specified, in this specification, examples of the "$C_{6-14}$ aryloxy (group)" include phenyloxy, 1-naphthyloxy and 2-naphthyloxy.

Unless otherwise specified, in this specification, examples of the "$C_{7-16}$ aralkyloxy (group)" include benzyloxy and phenethyloxy.

Unless otherwise specified, in this specification, examples of the "alkyl-carbonyloxy (group)" include $C_{1-6}$ alkyl-carbonyloxy (group).

Unless otherwise specified, in this specification, examples of the "$C_{1-6}$ alkyl-carbonyloxy (group)" include acetoxy and propionyloxy.

Unless otherwise specified, in this specification, examples of the "alkoxy-carbonyloxy (group)" include $C_{1-6}$ alkoxy-carbonyloxy (group).

Unless otherwise specified, in this specification, examples of the "$C_{1-6}$ alkoxy-carbonyloxy (group)" include methoxycarbonyloxy, ethoxycarbonyloxy, propoxycarbonyloxy and butoxycarbonyloxy.

Unless otherwise specified, in this specification, examples of the "mono-alkyl-carbamoyloxy (group)" include mono-$C_{1-6}$ alkyl-carbamoyloxy (group).

Unless otherwise specified, in this specification, examples of the "mono-$C_{1-6}$ alkyl-carbamoyloxy (group)" include methylcarbamoyloxy and ethylcarbamoyloxy.

Unless otherwise specified, in this specification, examples of the "di-alkyl-carbamoyloxy (group)" include di-$C_{1-6}$ alkyl-carbamoyloxy (group).

Unless otherwise specified, in this specification, examples of the "di-$C_{1-6}$ alkyl-carbamoyloxy (group)" include dimethylcarbamoyloxy and diethylcarbamoyloxy.

Unless otherwise specified, in this specification, examples of the "$C_{6-14}$ aryl-carbonyloxy (group)" include benzoyloxy and naphthylcarbonyloxy.

Unless otherwise specified, in this specification, examples of the "mono- or di-$C_{6-14}$ aryl-carbamoyloxy (group)" include phenylcarbamoyloxy and naphthylcarbamoyloxy.

Unless otherwise specified, in this specification, examples of the heterocyclic moiety of the "heterocyclyl-oxy (group)" include those similar to the above-mentioned "heterocyclic group". Specific examples of the "heterocyclyl-oxy (group)" include 5- to 14-membered heterocyclyl-oxy (group) having 1 to 5 hetero atoms selected from a nitrogen atom, a sulfur atom and an oxygen atom.

Unless otherwise specified, in this specification, examples of the aromatic heterocyclic moiety of the "heterocyclyl-oxy (group)" include those similar to the "aromatic heterocyclic group" as examples of the above-mentioned "heterocyclic group". Specific examples of the "aromatic heterocyclyl-oxy (group)" include 3- to 14-membered aromatic heterocyclyl-oxy (group) having 1 to 5 hetero atoms selected from a nitrogen atom, a sulfur atom and an oxygen atom.

Unless otherwise specified, in this specification, examples of the "$C_{1-6}$ alkylsulfonyloxy (group)" include methylsulfonyloxy and ethylsulfonyloxy.

Unless otherwise specified, in this specification, examples of the "halogeno $C_{1-6}$ alkylsulfonyloxy (group)" include halogenomethylsulfonyloxy and halogenoethylsulfonyloxy.

Unless otherwise specified, in this specification, examples of the "alkylsulfanyl (group)" include $C_{1-6}$ alkylsulfanyl (group).

Unless otherwise specified, in this specification, examples of the "$C_{1-6}$ alkylsulfanyl (group)" include methylsulfanyl, ethylsulfanyl, propylsulfanyl, isopropylsulfanyl, butylsulfanyl, sec-butylsulfanyl, and tert-butylsulfanyl.

Unless otherwise specified, in this specification, examples of the "$C_{3-7}$ cycloalkylsulfanyl (group)" include cyclopropylsulfanyl, cyclobutylsulfanyl, cyclopentylsulfanyl and cyclohexylsulfanyl.

Unless otherwise specified, in this specification, examples of the "$C_{6-14}$ arylsulfanyl (group)" include phenylsulfanyl, 1-naphthylsulfanyl and 2-naphthylsulfanyl.

Unless otherwise specified, in this specification, examples of the "$C_{7-16}$ aralkylsulfanyl (group)" include benzylsufanyl and phenethylsulfanyl.

Unless otherwise specified, in this specification, examples of the heterocyclic moiety of the "heterocyclyl-sulfanyl (group)" include those similar to the above-mentioned "heterocyclic group". Specific examples of the "heterocyclyl-sulfanyl (group)" include 5- to 14-membered heterocyclyl-sulfanyl (group) having 1 to 5 hetero atoms selected from a nitrogen atom, a sulfur atom and an oxygen atom.

Unless otherwise specified, in this specification, examples of the "alkyl-carbonyl (group)" include $C_{1-6}$ alkyl-carbonyl (group).

Unless otherwise specified, in this specification, examples of the "$C_{1-6}$ alkyl-carbonyl (group)" include acetyl, propionyl and pivaloyl.

Unless otherwise specified, in this specification, examples of the "$C_{3-7}$ cycloalkyl-carbonyl (group)" include cyclopropylcarbonyl, cyclopentylcarbonyl and cyclohexylcarbonyl.

Unless otherwise specified, in this specification, examples of the "$C_{6-14}$ aryl-carbonyl (group)" include benzoyl, 1-naphthoyl and 2-naphthoyl.

Unless otherwise specified, in this specification, examples of the "$C_{7-16}$ aralkyl-carbonyl (group)" include phenylacetyl and 3-phenylpropionyl.

Unless otherwise specified, in this specification, examples of the heterocyclic moiety of the "heterocyclyl-carbonyl (group)" include those similar to the above-mentioned "heterocyclic group". Specific examples thereof include 3- to 14-membered heterocyclyl-carbonyl (group) having 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2- ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

Unless otherwise specified, in this specification, examples of the "optionally esterified carboxy (group)" include carboxy, optionally substituted alkoxy-carbonyl, optionally substituted $C_{3-7}$ cycloalkyloxy-carbonyl, optionally substituted $C_{6-14}$ aryloxy-carbonyl, optionally substituted $C_{7-16}$ aralkyloxy-carbonyl, and optionally substituted silyloxy-carbonyl (e.g., TMS—O—CO—, TES—O—CO—, TBS—O—CO—, TIPS—O—CO—, TBDPS—O—CO—) and the like.

Unless otherwise specified, in this specification, examples of the "alkoxy-carbonyl (group)" include "$C_{1-6}$ alkoxy-carbonyl (group)".

Unless otherwise specified, in this specification, examples of the "$C_{1-6}$ alkoxy-carbonyl (group)" include methoxycarbonyl, ethoxycarbonyl, propoxycarbonyl, and tert-butoxycarbonyl.

Unless otherwise specified, in this specification, examples of the "$C_{3-7}$ cycloalkyloxy-carbonyl (group)" include cyclopropyloxycarbonyl, cyclopentyloxycarbonyl, and cyclohexyloxycarbonyl.

Unless otherwise specified, in this specification, examples of the "$C_{6-14}$ aryloxy-carbonyl (group)" include phenoxycarbonyl.

Unless otherwise specified, in this specification, examples of the "$C_{7-16}$ aralkyloxy-carbonyl (group)" include benzyloxycarbonyl and phenethyloxycarbonyl.

Unless otherwise specified, in this specification, examples of the "alkylsulfonyl (group)" include $C_{1-6}$ alkylsulfonyl (group).

Unless otherwise specified, in this specification, examples of the "$C_{1-6}$ alkylsulfonyl (group)" include methylsulfonyl and ethylsulfonyl.

Unless otherwise specified, in this specification, examples of the "$C_{3-7}$ cycloalkylsulfonyl (group)" include cyclopropylsulfonyl, cyclobutylsulfonyl, cyclopentylsulfonyl and cyclohexylsulfonyl.

Unless otherwise specified, in this specification, examples of the "$C_{6-14}$ arylsulfonyl (group)" include phenylsulfonyl, 1-naphthylsulfonyl and 2-naphthylsulfonyl.

Unless otherwise specified, in this specification, examples of the heterocyclic moiety of the "heterocyclyl-sulfonyl (group)" include those similar to the above-mentioned "heterocyclic group". Specific examples of the "heterocyclyl-sulfonyl (group)" include 5- to 14-membered heterocyclyl-sulfonyl (group) having 1 to 5 hetero atoms selected from a nitrogen atom, a sulfur atom and an oxygen atom.

Unless otherwise specified, in this specification, examples of the "alkylsulfinyl (group)" include $C_{1-6}$ alkylsulfinyl (group).

Unless otherwise specified, in this specification, examples of the "$C_{1-6}$ alkylsulfinyl (group)" include methylsulfinyl and ethylsulfinyl.

Unless otherwise specified, in this specification, examples of the "$C_{3-7}$ cycloalkylsulfinyl (group)" include cyclopropylsulfinyl, cyclobutylsulfinyl, cyclopentylsufinyl, and cyclohexysulfinyl.

Unless otherwise specified, in this specification, examples of the "$C_{6-14}$ arylsulfinyl (group)" include phenylsulfinyl, 1-naphthylsulfinyl and 2-naphthylsulfinyl.

Unless otherwise specified, in this specification, examples of the heterocyclic moiety of the "heterocyclyl-sulfinyl (group)" include those similar to the above-mentioned "heterocyclic group". Specific examples of the "heterocyclyl-sulfinyl (group)" include 5- to 14-membered heterocyclyl-sulfinyl (group) having 1 to 5 hetero atoms selected from a nitrogen atom, a sulfur atom and an oxygen atom.

Unless otherwise specified, in this specification, examples of the "alkyl-carbamoyl (group)" include mono- or di-$C_{1-6}$ alkyl-carbamoyl (group).

Unless otherwise specified, in this specification, examples of the "mono- or di-$C_{1-6}$ alkyl-carbamoyl (group)" include methylcarbamoyl, ethylcarbamoyl, propylcarbamoyl, dimethylcarbamoyl, diethylcarbamoyl and ethylmethylcarbamoyl.

Unless otherwise specified, in this specification, examples of the "aryl-carbamoyl (group)" include mono-, or di-$C_{6-14}$ aryl-carbamoyl (group)".

Unless otherwise specified, in this specification, examples of the "mono-, or di-$C_{6-14}$ aryl-carbamoyl (group)" include phenylcarbamoyl, 1-naphthylcarbamoyl, and 2-naphthylcarbamoyl.

Unless otherwise specified, in this specification, examples of the "mono- or di-alkylamino (group)" include mono- or di-$C_{1-6}$ alkylamino (group).

Unless otherwise specified, in this specification, examples of the "mono- or di-$C_{1-6}$ alkylamino (group)" include methylamino, ethylamino, propylamino, dimethylamino and diethylamino.

Unless otherwise specified, in this specification, examples of the "alkyl-carbonylamino (group)" include $C_{1-6}$ alkyl-carbonylamino.

Unless otherwise specified, in this specification, examples of the "$C_{1-6}$ alkyl-carbonylamino (group)" include acetylamino, propionylamino and pivaloylamino.

Unless otherwise specified, in this specification, as the "heterocyclic group" of the "heterocyclyl-amino (group)", for example, those similar to the above-mentioned "heterocyclic group" can be used. Examples of the "heterocyclyl-amino (group)" include 2-pyridyl-amino.

Unless otherwise specified, in this specification, as the "heterocyclyl-carbonyl" of the "heterocyclyl-carbonylamino (group)", those similar to the above-mentioned "heterocyclyl-carbonyl" can be used. Examples of the "heterocyclyl-carbonylamino (group)" include pyridyl-carbonylamino.

Unless otherwise specified, in this specification, as the "heterocyclic (group)" of the "heterocyclyl-oxycarbonylamino (group)", those similar to the above-mentioned "heterocyclic group" can be used. Examples of the "heterocyclyl-oxycarbonylamino (group)" include 2-pyridyl-oxycarbonylamino.

Unless otherwise specified, in this specification, as the "heterocyclic (group)" of the "heterocyclyl-sulfonylamino (group)", for example, those similar to the above-mentioned "heterocyclic group" can be used. Examples of the "heterocyclyl-sulfonylamino (group)" include 2-pyridyl-sulfonylamino.

Unless otherwise specified, in this specification, examples of the "alkoxy-carbonylamino (group)" include $C_{1-6}$ alkoxy-carbonylamino (group).

Unless otherwise specified, in this specification, the "$C_{1-6}$ alkoxy-carbonylamino (group)" include methoxycarbonylamino, ethoxycarbonylamino, propoxycarbonylamino and butoxycarbonylamino.

Unless otherwise specified, in this specification, examples of the "alkylsulfonylamino (group)" include $C_{1-6}$ alkylsulfonylamino (group).

Unless otherwise specified, in this specification, examples of the "$C_{1-6}$ alkylsulfonylamino (group)" include methylsulfonylamino and ethylsulfonylamino.

Unless otherwise specified, in this specification, examples of the "mono- or di-$C_{3-7}$ cycloalkylamino (group)" include cyclopropylamino, cyclopentylamino and cyclohexylamino.

Unless otherwise specified, in this specification, examples of the "$C_{3-7}$ cycloalkyl-carbonylamino (group)" include cyclopropylcarbonylamino, cyclopentylcarbonylamino and cyclohexylcarbonylamino.

Unless otherwise specified, in this specification, examples of the "$C_{3-7}$ cycloalkyloxy-carbonylamino (group)" include cyclopropoxycarbonylamino, cyclopentyloxycarbonylamino and cyclohexyloxycarbonylamino.

Unless otherwise specified, in this specification, examples of the "$C_{3-7}$ cycloalkylsulfonylamino (group)" include cyclopropylsulfonylamino, cyclopentylsulfonylamino and cyclohexylsulfonylamino.

Unless otherwise specified, in this specification, examples of the "mono- or di-$C_{6-14}$ arylamino (group)" include phenylamino and diphenylamino.

Unless otherwise specified, in this specification, examples of the "mono- or di-$C_{7-16}$ aralkylamino (group)" include benzylamino.

Unless otherwise specified, in this specification, examples of the "$C_{6-14}$ aryl-carbonylamino (group)" include benzoylamino and naphthoylamino.

Unless otherwise specified, in this specification, examples of the "$C_{6-14}$ arylsulfonylamino (group)" include phenylsulfonylamino, 2-naphthylsulfonylamino and 1-naphthylsulfonylamino.

Unless otherwise specified, in this specification, examples of the "$C_{1-3}$ alkylene (group)" include methylene, ethylene, propylene, —CH(CH$_3$)—CH$_2$—, —CH$_2$—CH(CH$_3$)—, —C(CH$_3$)$_2$— and the like.

[Substituent group A]
(1) halogen atom;
(2) nitro group;
(3) cyano group;
(4) optionally esterified carboxy group;
(5) optionally substituted alkyl group;
(6) optionally substituted alkenyl group;
(7) optionally substituted alkynyl group (e.g., optionally substituted $C_{3-7}$ cycloalkyl-$C_{2-6}$ alkynyl group);
(8) optionally substituted $C_{3-7}$ cycloalkyl group;
(9) optionally substituted $C_{6-14}$ aryl group;
(10) optionally substituted $C_{7-16}$ aralkyl group;
(11) optionally substituted $C_{6-14}$ aryl-$C_{2-6}$ alkenyl group;
(12) optionally substituted heterocyclic group;
(13) hydroxy group;
(14) optionally substituted alkoxy group;
(15) optionally substituted $C_{3-7}$ cycloalkyloxy group;
(16) optionally substituted $C_{6-14}$ aryloxy group;
(17) optionally substituted $C_{7-16}$ aralkyloxy group;
(18) optionally substituted alkyl-carbonyloxy group;
(19) optionally substituted alkoxy-carbonyloxy group;
(20) optionally substituted mono-alkyl-carbamoyloxy group;
(21) optionally substituted di-alkyl-carbamoyloxy group;
(22) optionally substituted $C_{6-14}$ aryl-carbonyloxy group;
(23) optionally substituted mono-, or di-$C_{6-14}$ aryl-carbamoyloxy group;
(24) optionally substituted heterocyclyl-oxy group (e.g., optionally substituted aromatic heterocyclyl-oxy group);
(25) optionally substituted $C_{1-6}$ alkylsulfonyloxy group (e.g., optionally substituted halogeno $C_{1-6}$ alkylsulfonyloxy group),
(26) mercapto group;
(27) optionally substituted alkylsulfanyl group;
(28) optionally substituted $C_{3-7}$ cycloalkylsulfanyl group;
(29) optionally substituted $C_{6-14}$ arylsulfanyl group;
(30) optionally substituted $C_{7-16}$ aralkylsulfanyl group;
(31) optionally substituted heterocyclyl-sulfanyl group;
(32) formyl group;
(33) optionally substituted alkyl-carbonyl group;
(34) optionally substituted $C_{3-7}$ cycloalkyl-carbonyl group;
(35) optionally substituted $C_{6-14}$ aryl-carbonyl group;
(36) optionally substituted $C_{7-16}$ aralkyl-carbonyl group;
(37) optionally substituted heterocyclyl-carbonyl group;
(38) optionally substituted alkylsulfonyl group;
(39) optionally substituted $C_{3-7}$ cycloalkylsulfonyl group;
(40) optionally substituted $C_{6-14}$ arylsulfonyl group;
(41) optionally substituted heterocyclyl-sulfonyl group;
(42) optionally substituted alkylsulfinyl group;
(43) optionally substituted $C_{3-7}$ cycloalkylsulfinyl group;
(44) optionally substituted $C_{6-14}$ arylsulfinyl group;
(45) optionally substituted heterocyclyl-sulfinyl group;
(46) sulfo group;
(47) sulfamoyl group;
(48) sulfinamoyl group;
(49) sulfenamoyl group;
(50) thiocarbamoyl group;
(51) optionally substituted carbamoyl group [e.g., optionally substituted alkyl-carbamoyl, optionally substituted aryl-carbamoyl and the like];
(52) optionally substituted amino group [e.g., amino, optionally substituted mono-, or di-alkylamino group, optionally substituted mono-, or di-$C_{3-7}$ cycloalkylamino group, optionally substituted mono-, or di-$C_{6-14}$ arylamino group, optionally substituted mono-, or di-$C_{7-16}$ aralkylamino group, optionally substituted heterocyclyl-amino group, optionally substituted $C_{6-14}$ aryl-carbonylamino group, formylamino group,
optionally substituted alkyl-carbonylamino group (e.g., mono-($C_{1-6}$ alkyl-carbonyl)-amino group),
optionally substituted $C_{3-7}$ cycloalkyl-carbonylamino group,
optionally substituted heterocyclyl-carbonylamino group,
optionally substituted alkoxy-carbonylamino group,
optionally substituted $C_{3-7}$ cycloalkyloxy-carbonylamino group,
optionally substituted heterocyclyl-oxycarbonylamino group,
optionally substituted carbamoylamino group,
optionally substituted alkylsulfonylamino group,
optionally substituted $C_{3-7}$ cycloalkylsulfonylamino group,
optionally substituted heterocyclyl-sulfonylamino group,
optionally substituted $C_{6-14}$ arylsulfonylamino group]

The number of said substituents is preferably 0 (i.e., unsubstituted), or 1-2.

The number of said substituent is more preferably 0 (i.e., unsubstituted).

In the substituent group A, examples of the substituents of the
"optionally substituted alkoxy-carbonyl group",
"optionally substituted alkyl group",
"optionally substituted alkenyl group",
"optionally substituted alkynyl group",
"optionally substituted alkoxy group",
"optionally substituted alkyl-carbonyloxy group",
"optionally substituted alkoxy-carbonyloxy group",
"optionally substituted mono-alkyl-carbamoyloxy group",
"optionally substituted di-alkyl-carbamoyloxy group",
"optionally substituted $C_{1-6}$ alkylsulfonyloxy group",
"optionally substituted alkylsulfanyl group",
"optionally substituted alkyl-carbonyl group", "optionally substituted alkylsulfonyl group",
"optionally substituted alkylsulfinyl group",
"optionally substituted alkyl-carbamoyl group",
"optionally substituted mono-, or di-alkylamino group",
"optionally substituted alkyl-carbonylamino group",
"optionally substituted mono-($C_{1-6}$ alkyl-carbonyl)-amino group",
"optionally substituted alkoxy-carbonylamino group", and
"optionally substituted alkylsulfonylamino group" include those selected from the following substituent group B.

In the substituent group A, examples of the substituents of the
"optionally substituted $C_{3-7}$ cycloalkyloxy-carbonyl group",
"optionally substituted $C_{6-14}$ aryloxy-carbonyl group",
"optionally substituted $C_{7-16}$ aralkyloxy-carbonyl group",
"optionally substituted $C_{3-7}$ cycloalkyl-$C_{2-6}$ alkynyl group",
"optionally substituted $C_{3-7}$ cycloalkyl group",
"optionally substituted $C_{6-14}$ aryl group",
"optionally substituted $C_{7-16}$ aralkyl group",
"optionally substituted $C_{6-14}$ aryl-$C_{2-6}$ alkenyl group",
"optionally substituted heterocyclic group",
"optionally substituted $C_{1-7}$ cycloalkyloxy group",
"optionally substituted $C_{6-14}$ aryloxy group",
"optionally substituted $C_{7-16}$ aralkyloxy group",
"optionally substituted $C_{6-14}$ aryl-carbonyloxy group",
"optionally substituted mono-, or di-$C_{6-14}$ aryl-carbamoyloxy group",
"optionally substituted heterocyclyl-oxy group",
"optionally substituted aromatic heterocyclyl-oxy group",
"optionally substituted $C_{2-7}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-7}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-7}$ cycloalkylsulfonyl group",
"optionally substituted $C_{6-14}$ arylsulfonyl group",
"optionally substituted heterocyclyl-sulfonyl group",
"optionally substituted $C_{3-7}$ cycloalkylsulfinyl group",
"optionally substituted $C_{6-14}$ arylsulfinyl group",
"optionally substituted heterocyclyl-sulfinyl group",
"optionally substituted carbamoyl group",
"optionally substituted amino group",
"optionally substituted mono- or di-$C_{3-7}$ cycloalkylamino group",
"optionally substituted mono- or di-$C_{6-14}$ arylamino group",
"optionally substituted mono- or di-$C_{7-16}$ aralkylamino group",
"optionally substituted heterocyclyl-amino group",
"optionally substituted $C_{6-14}$ aryl-carbonylamino group",
"optionally substituted $C_{3-7}$ cycloalkyl-carbonylamino group",
"optionally substituted heterocyclyl-carbonylamino group",
"optionally substituted $C_{3-7}$ cycloalkoxy-carbonylamino group",
"optionally substituted heterocyclyl-oxycarbonylamino group",
"optionally substituted carbamoylamino group",
"optionally substituted alkylsulfonylamino group",
"optionally substituted $C_{3-7}$ cycloalkylsulfonylamino group",
"optionally substituted heterocyclyl-sulfonylamino group", and
"optionally substituted $C_{6-14}$ arylsulfonylamino group" include those selected from the following substituent group B, and the following substituent group B'. The number of said substituents is 1—substitutable maximum number, more preferably 1-3, more preferably 1.

In the present specification, substituent group B consists of
(a) halogen atom;
(b) hydroxy group;
(c) nitro group;
(d) cyano group;
(e) optionally substituted $C_{6-14}$ aryl group (said $C_{6-14}$ aryl group is optionally substituted by substituent(s) such as halogen atom, hydroxy, cyano, amino, optionally halogenated $C_{1-6}$ alkyl, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{3-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like);
(f) optionally substituted $C_{6-14}$ aryloxy group (said $C_{6-14}$ aryloxy group is optionally substituted by substituent(s) such as halogen atom, hydroxy, cyano, amino, optionally halogenated $C_{1-6}$ alkyl, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like);
(g) optionally substituted $C_{7-16}$ aralkyloxy group (said $C_{7-15}$ aralkyloxy group is optionally substituted by substituent(s) such as halogen atom, hydroxy, cyano, amino, optionally halogenated $C_{1-6}$ alkyl, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like);
(h) optionally substituted mono-, or di-5- to 10-membered heterocyclic group having 1-4 hetero atoms selected from a nitrogen atom, a sulfur atom, and an oxygen atom (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinolin-2-yl and the like) (said heterocyclic group is optionally substituted by substituent(s) such as halogen atom, hydroxy, cyano, amino, optionally halogenated $C_{1-6}$ alkyl, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-5}$ alkyl-carbamoyl, mono-, or di-$C_{6-14}$ aryl-carbamoyl and the like);
(i) optionally substituted amino group [for example, amino group optionally substituted by 1 or 2 substituents selected from the group consisting of $C_{1-6}$ alkyl, $C_{2-6}$ alkenyl, $C_{6-14}$ aryl, $C_{7-16}$ aralkyl, heterocyclic group, and heterocyclyl-alkyl (said $C_{1-6}$ alkyl, $C_{2-6}$ alkenyl, $C_{6-14}$ aryl, $C_{7-16}$ aralkyl, heterocyclic group, and heterocyclyl-alkyl are each optionally substituted by substituent(s) such as halogen atom, hydroxy, cyano, amino, optionally halogenated $C_{1-6}$ alkyl (which is not a substituent for alkyl and alkenyl), mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono-, or di-$C_{1-6}$ alkyl-carbamoyl, mono-, or di-$C_{6-14}$ arylcarbamoyl and the like. Examples of the "heterocyclic group" and "heterocyclyl-" of the "heterocyclyl-alkyl" include those similar to the above-mentioned "heterocyclic group").];
(j) $C_{3-7}$ cycloalkyl;
(k) optionally substituted $C_{1-6}$ alkoxy group (said $C_{1-6}$ alkoxy group is optionally substituted by substituent(s) such as halogen atom, hydroxy, amino, mono-, or di-$C_{1-6}$ alkylamino, mono-, or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl, trimethylsilyl (TMS) and the like);
(l) formyl group;
(m) $C_{1-6}$ alkyl-carbonyl group (e.g., acetyl);
(n) $C_{3-7}$ cycloalkyl-carbonyl group;
(o) $C_{6-14}$ aryl-carbonyl group;
(p) $C_{7-16}$ aralkyl-carbonyl group;
(q) $C_{1-6}$ alkoxy-carbonyl group;
(r) $C_{6-14}$ aryloxy-carbonyl group;
(s) $C_{7-16}$ aralkyloxy-carbonyl group;
(t) $C_{1-6}$ alkylsulfanyl group;
(u) $C_{1-6}$ alkylsulfinyl group;
(v) $C_{1-6}$ alkylsulfonyl group;
(w) carbamoyl group;
(x) thiocarbamoyl group;
(y) mono-$C_{1-6}$ alkyl-carbamoyl group (e.g., methylcarbamoyl, ethylcarbamoyl and the like);
(z) alkyl-carbamoyl group (e.g., dimethylcarbamoyl, diethylcarbamoyl, ethylmethylcarbamoyl and the like);
(aa) mono-, or di-$C_{6-14}$ aryl-carbamoyl group (e.g., phenylcarbamoyl, 1-naphthylcarbamoyl, 2-naphthylcarbamoyl and the like); and
(bb) mono-, or di-5- to 7-membered heterocyclyl-carbamoyl group having 1-4 hetero atoms selected from a nitrogen atom, a sulfur atom, and an oxygen atom (e.g., 2-pyridylcarbamoyl, 3-pyridylcarbamoyl, 4-pyridylcarbamoyl, 2-thienylcarbamoyl, 3-thienylcarbamoyl and the like).

In the present specification, substituent group B' consists of
(a) optionally substituted $C_{1-6}$ alkyl group (said $C_{1-6}$ alkyl group is optionally substituted by substituent(s) such as a halogen atom, hydroxy, cyano, amino, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{3-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like);
(b) optionally substituted $C_{2-6}$ alkenyl group (said $C_{2-6}$ alkenyl group is optionally substituted by substituent(s) such as halogen atom, hydroxy, cyano, amino, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like); and
(c) optionally substituted $C_{2-6}$ alkynyl group (said $C_{2-6}$ alkynyl group is optionally substituted by substituent(s) such as halogen atom, hydroxy, cyano, amino, mono-, or di-$C_{1-6}$ alkylamino, mono-, or di-$C_{6-14}$ arylamino, mono-, or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono-, or di-$C_{1-6}$ alkyl-carbamoyl, mono-, or di-$C_{6-14}$ aryl-carbamoyl and the like).

The symbols in the following formula ($1^x$) are explained below.

$R^{x1}$ and $R^{x5}$ are the same or different and each is a substituent. Examples of the "substituent" include those selected from the aforementioned substituent group A.

$R^{x2}$, $R^{x3}$ and $R^{x4}$ are the same or different and each is absent, a hydrogen atom or a substituent. Examples of the "substituent" include those selected from the aforementioned substituent group A.

Ring $A^x$ is a 5- or 6-membered ring optionally further substituted. Examples of the "5- or 6-membered ring" include 5- or 6-membered rings from the aforementioned "heterocycle" and "hydrocarbon ring". Examples of the substituent of the "optionally substituted 5- or 6-membered ring" include those selected from the aforementioned substituent group A.

Ring $B^x$ is a heterocycle optionally further substituted. Examples of the "heterocycle" include the aforementioned "heterocycle". Examples of the substituent of the "optionally substituted heterocycle" include those selected from the aforementioned substituent group A.

Any two of $R^{x1}$, $R^{x2}$, $R^{x3}$ and $R^{x4}$ may be bonded to form, together with ring $A^x$, an optionally substituted bicyclic fused ring, or an optionally substituted tricyclic fused ring.

A compound represented by the formula ($1^{x'}$) and a salt thereof are encompassed in compound ($1^x$). The symbols in the following formula ($1^{x'}$) are explained.

$R^{x1'}$ and $R^{5x'}$ show substituents. Examples of the "substituent" include those selected from the aforementioned substituent group A.

$R^{x2'}$ and $R^{x3'}$ are the same or different and each is a hydrogen atom or a substituent. Examples of the "substituent" include those selected from the aforementioned substituent group A.

Ring $B^{x'}$ is a heterocycle optionally further substituted. Examples of the "heterocycle" include the aforementioned "heterocycle". Examples of the substituent of the "optionally substituted heterocycle" include those selected from the aforementioned substituent group A.

When $R^{x1'}$ is an optionally substituted aromatic ring, ring $B^{x'}$ is not a 5-membered aromatic heterocycle optionally further substituted.

Compound (1) is preferably, for example, the following compounds (1a), (1b), (1c), (1d), (1e) and (1f).
[Compound (1a)]
Compound (1) which is a compound represented by the following formula (1a) or a salt thereof.

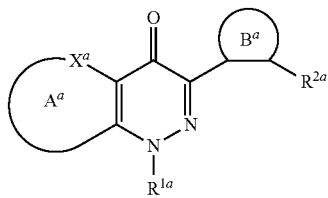

(1a)

wherein ring $A^a$ is an optionally substituted 5- to 7-membered heterocycle; $X^a$ is an oxygen atom, a sulfur atom or —$NR^a$— ($R^a$ is a hydrogen atom or a substituent); $R^{1a}$ is a substituent; ring $B^a$ is a nitrogen-containing heterocycle optionally further substituted; and $R^{2a}$ is a substituent.

As the "5- to 7-membered heterocycle" of the "optionally substituted 5- to 7-membered heterocycle" for ring $A^a$, among the aforementioned heterocycles, a 5- to 7-membered one having a structure corresponding to $X^a$ can be mentioned. Said "heterocycle" is preferably furan ring, dihydrofuran ring, thiophene ring, pyrazole ring, pyridine ring and the like, particularly preferably furan ring, dihydrofuran ring or the like.

Examples of the substituent of the "5- to 7-membered heterocycle" include those selected from the aforementioned substituent group A.

Preferred as ring $A^a$ is unsubstituted 5- to 7-membered heterocycle (e.g., furan ring, dihydrofuran ring).

Examples of the "nitrogen-containing heterocycle" of the "nitrogen-containing heterocycle optionally further substituted" for ring $B^a$ include the aforementioned "nitrogen-containing heterocycle". Preferred as said "nitrogen-containing heterocycle" is pyrazole ring, triazole ring, is tetrazole ring, pyridine ring or the like. Particularly preferred is pyrazole ring.

Examples of the substituent of the "nitrogen-containing heterocycle" include those selected from the aforementioned substituent group A.

Preferred as ring $B^a$ is nitrogen-containing heterocycle (e.g., pyrazole ring) free of further substituent.

$X^a$ is preferably an oxygen atom or —$NR^a$— ($R^a$ is a hydrogen atom or a substituent), more preferably an oxygen atom.

Examples of the "substituent" for $R^{1a}$ include those selected from the aforementioned substituent group A. Preferred are $C_{1-6}$ alkyl group substituted by a halogen atom (e.g., trifluoromethyl), alkoxy group substituted by a halogen atom (e.g., trifluoromethoxy), and pyrazolyl group.

Examples of the "substituent" for $R^{2a}$ include those selected from the aforementioned substituent group A. Preferred is $C_{6-14}$ aryl group (e.g., phenyl).

Examples of the "substituent" for $R^a$ include those selected from the aforementioned substituent group A.

As compound (1a), preferred is (1) a compound wherein
ring $A^a$ is an optionally substituted furan ring or optionally substituted dihydrofuran ring;
$X^a$ is an oxygen atom;
$R^{1a}$ is an optionally substituted phenyl group;
ring $B^a$ is an optionally substituted pyrazole ring;
$R^{2a}$ is an optionally substituted phenyl group;
or a salt thereof, more preferably, (2) a compound wherein
ring $A^a$ is a furan ring or dihydrofuran ring;
$X^a$ is an oxygen atom;
$R^{1a}$ is a phenyl group substituted by 1 to 3 substituents selected from a $C_{1-6}$ alkyl group substituted by a halogen atom, a $C_{1-6}$ alkoxy group substituted by a halogen atom, and a pyrazolyl group;
ring $B^a$ is a pyrazole ring; and
$R^{2a}$ is a phenyl group;
or a salt thereof.

[Compound (1b)]

Compound (1), which is a compound represented by the following formula (1b), or a salt thereof.

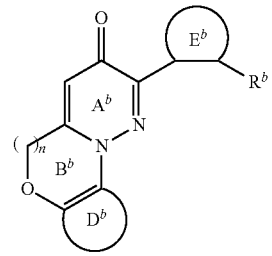

(1b)

wherein ring $A^b$ is a ring optionally further substituted; ring $B^b$ is an optionally substituted ring; ring $D^b$ is an optionally substituted 6- to 10-membered aromatic hydrocarbon ring; n is 0, 1 or 2; ring $E^b$ is a 5- to 10-membered aromatic heterocycle optionally further substituted; and $R^b$ is a substituent.

Examples of the substituent of the "ring optionally further substituted" for ring $A^b$ include those selected from the aforementioned substituent group A.

Preferred as ring $A^b$ is a ring (dihydropyridazine ring) free of further substituent.

Examples of the substituent of the "optionally substituted ring" for ring $B^b$ include those selected from the aforementioned substituent group A.

Preferred as ring $B^b$ is an unsubstituted ring (e.g., dihydrooxazin ring).

As the "6- to 10-membered aromatic hydrocarbon ring" of the "optionally substituted 6- to 10-membered aromatic hydrocarbon ring" for ring $D^b$, benzene ring and naphthalene ring can be mentioned. Preferred is benzene ring.

Examples of the substituent of the "6- to 10-membered aromatic hydrocarbon ring" include those selected from the aforementioned substituent group A can be mentioned.

Preferred as ring $D^b$ is 6- to 10-membered aromatic hydrocarbon ring (e.g., benzene ring) free of further substituent.

As the "5- to 10-membered aromatic heterocycle" of the "5- to 10-membered aromatic heterocycle optionally further substituted" for ring $E^b$, among the aforementioned aromatic heterocycles, a 5- to 10-membered one can be mentioned. Preferred as the "5- to 10-membered aromatic heterocycle" is pyrazole ring, triazole ring, tetrazole ring, furan ring, pyridine ring or the like. Preferred is a pyrazole ring.

Examples of the substituent of the "5- to 10-membered aromatic heterocycle" include those selected from the aforementioned substituent group A.

Preferred as ring $E^b$ is 5- to 10-membered aromatic heterocycle (e.g., pyrazole ring) free of further substituent.

n is preferably 1.

Examples of the "substituent" for $R^b$ include those selected from the aforementioned substituent group A. Preferred is $C_{6-14}$ aryl group (e.g., phenyl). Compound (1b) is preferably (1) a compound wherein
ring $A^b$ is a ring optionally further substituted (dihydropyridazine ring);
ring $B^b$ is an optionally substituted ring (e.g., dihydrooxazin ring);
ring $D^b$ is an optionally substituted benzene ring;
n is 1;
ring $E^b$ is a pyrazole ring optionally further substituted; and
$R^b$ is a phenyl ring optionally further substituted;
or a salt thereof, more preferably,
(2) a compound wherein
ring $A^b$ is a ring free of further substituent (dihydropyridazine ring);
ring $B^b$ is an unsubstituted ring (e.g., dihydrooxazin ring);
ring $D^b$ is a benzene ring;
n is 1;
ring $E^b$ is a pyrazole ring;
$R^b$ is a phenyl group;
or a salt thereof.
[Compound (1c)]
Compound (1), which is a compound represented by the following formula (1c), or a salt thereof.

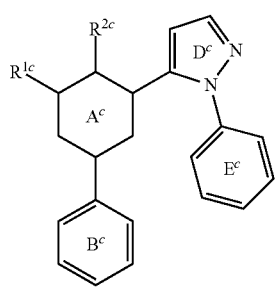

(1c)

wherein ring $A^c$ is a 6-membered heterocycle optionally further substituted; ring $B^c$ is an optionally substituted 6-membered aromatic ring; $R^{1c}$ is a hydrogen atom or a substituent (excluding aromatic ring group and —CO—$R^x$ ($R^x$ is a substituent)); $R^{2c}$ is a hydrogen atom, a hydroxy group, an oxo group or an optionally substituted $C_{1-5}$ alkoxy group; ring $D^c$ is a pyrazole ring optionally further substituted; ring $E^c$ is an optionally substituted benzene ring.

As the "6-membered heterocycle" of the "6-membered heterocycle optionally further substituted" for ring $A^c$, among the aforementioned heterocycles, a 6-membered one can be mentioned. Concrete examples thereof include the ring moiety of the group described as an example of the partial structural formula of the below-mentioned formula (1c).

Examples of the substituent of the "6-membered heterocycle" include those selected from the aforementioned substituent group A.

Preferred as ring $A^c$ is 6-membered heterocycle free of further substituent, more preferably 6-membered aromatic heterocycle (e.g., thiopyran ring, pyran ring, pyrazine ring, pyridine ring, pyridazine ring, dihydropyridazine ring, pyrimidine ring). More preferred is the ring moiety of the group described as an example of the partial structural formula of the below-mentioned formula (1c).

As the "6-membered aromatic ring" of the "optionally substituted 6-membered aromatic ring" for ring $B^c$, among the aforementioned aromatic heterocycles and aromatic hydrocarbon rings, a 6-membered one can be mentioned. The "6-membered aromatic ring" is preferably a benzene ring and the like.

Examples of the substituent of the "6-membered aromatic ring" include those selected from the aforementioned substituent group A. Preferred are a halogen atom (e.g., fluorine), and $C_{1-5}$ alkyl group substituted by a halogen atom (e.g., trifluoromethyl).

Preferred as ring $B^c$ is a benzene ring optionally substituted by a halogen atom (e.g., fluorine), and $C_{1-6}$ alkyl group substituted by a halogen atom (e.g., trifluoromethyl). More preferred is an unsubstituted benzene ring.

Examples of the "substituent" for $R^{1c}$ include those selected from the aforementioned substituent group A. Preferred are oxo group and $C_{1-6}$ alkoxy group (e.g., methoxy).

Preferred as $R^{1c}$ is a hydrogen atom, an oxo group, or a $C_{1-6}$ alkoxy group (e.g., methoxy).

Examples of the substituent of the "pyrazole ring optionally further substituted" for ring $D^c$ include, for example, those selected from the aforementioned substituent group A.

Preferred as ring $D^c$ is a pyrazole ring free of further substituent.

Examples of the substituent of the "optionally substituted benzene ring" for ring $E^c$ include those selected from the aforementioned substituent group A.

Preferred as ring $E^c$ is an unsubstituted benzene ring.

Examples of the partial structural formula of the formula (1c)

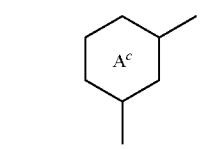

include

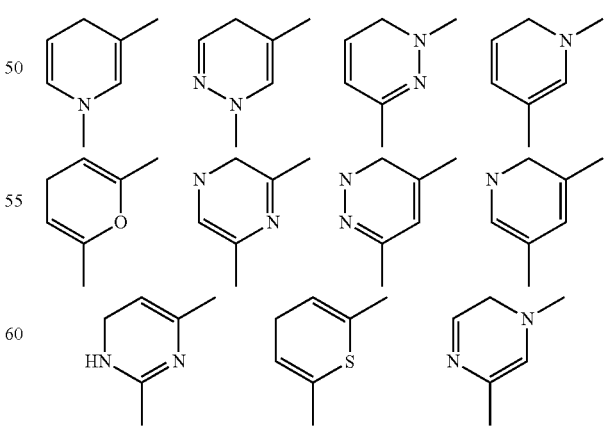

(wherein each ring is optionally further substituted at a position other than $R^{1c}$ and $R^{2c}$) and the like.

Compound (1c) is preferably (1)

a compound wherein a partial structural formula of the formula (1c):

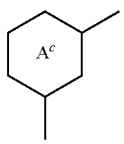

is

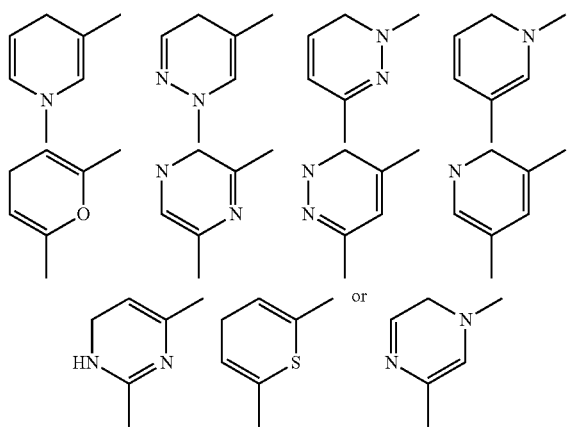

(wherein each ring is optionally further substituted at substitutable position), ring $B^c$ is an optionally substituted benzene ring;
$R^{1c}$ is a hydrogen atom, a $C_{1-6}$ alkoxy group or an oxo group;
$R^{2c}$ is a hydrogen atom, a hydroxy group, an oxo group or an optionally substituted $C_{1-6}$ alkoxy group;
ring $D^c$ is an optionally substituted pyrazole ring; and
ring $E^c$ is an optionally substituted benzene ring;
or a salt thereof, particularly preferably, (2)

a compound wherein a partial structural formula of the formula (1c):

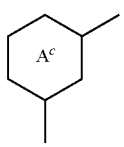

is

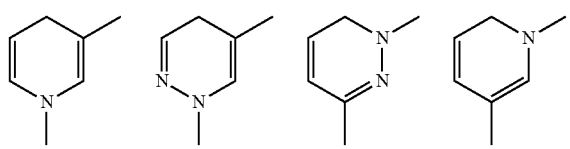

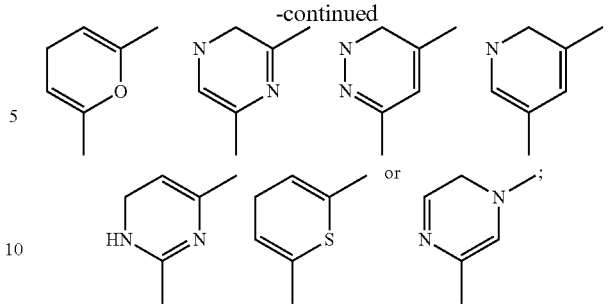

ring $B^c$ is a benzene ring optionally substituted by a halogen atom (e.g., fluorine) or a $C_{1-6}$ alkyl group substituted by a halogen atom (e.g., trifluoromethyl);
$R^{1c}$ is a hydrogen atom, a $C_{1-6}$ alkoxy group (e.g., methoxy) or an oxo group;
$R^{2c}$ is a hydrogen atom, a hydroxy group, an oxo group or a $C_{1-6}$ alkoxy group (e.g., methoxy);
ring $D^c$ is a pyrazole ring; and
ring $E^c$ is a benzene ring;
or a salt thereof.

[Compound (1d)]

Compound (1d), which is a compound represented by the following formula (1d) or a salt thereof.

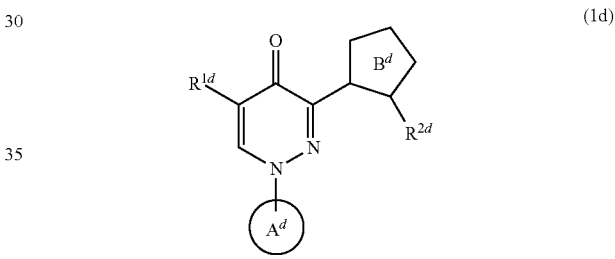

wherein ring $A^d$ is an optionally substituted 3- to 10-membered non-aromatic ring; $R^{1d}$ is a hydrogen atom or a $C_{1-6}$ alkoxy group; ring $B^d$ is a 5-membered aromatic heterocycle optionally further substituted; and $R^{2d}$ is a substituent.

As the "optionally substituted 3- to 10-membered non-aromatic ring" for ring $A^d$, among the aforementioned non-aromatic hydrocarbon rings and non-aromatic heterocycles, 3- to 10-membered one can be mentioned. The "3- to 10-membered non-aromatic ring" is preferably $C_{3-8}$ cycloalkane (e.g., cyclopropane), tetrahydronaphthalene ring, tetrahydropyridine ring, piperidine ring, azetidine ring, pyrrolidine ring, oxetane ring, azepane ring and the like, more preferably, $C_{3-8}$ cycloalkane (e.g., cyclopropane), tetrahydronaphthalene ring, tetrahydropyridine ring, piperidine ring, and azetidine ring.

Examples of the substituent of the "3- to 10-membered non-aromatic ring" include those selected from the aforementioned substituent group A. As the substituent, preferred are those selected from the group consisting of [substituent group A-1]

(a) optionally esterified carboxy group [e.g., optionally substituted alkoxy-carbonyl group, optionally substituted $C_{6-14}$ aryloxy-carbonyl group];
(b) optionally substituted alkyl group;
(c) optionally substituted alkenyl group;
(d) optionally substituted $C_{6-14}$ aryl group;
(e) optionally substituted heterocyclic group;

(f) optionally substituted alkyl-carbonyl group;
(g) optionally substituted $C_{6-14}$ aryl-carbonyl group; and
(h) optionally substituted carbamoyl group [e.g., optionally substituted alkyl-carbamoyl group, optionally substituted arylcarbamoyl group]. Preferred as ring $A^d$ are $C_{3-8}$ cycloalkane (e.g., cyclopropane), tetrahydronaphthalene ring, tetrahydropyridine ring, piperidine ring, and azetidine ring, which are optionally substituted by substituent(s) selected from substituent group A-1.

As the "5-membered aromatic heterocycle" of the "5-membered aromatic heterocycle optionally further substituted" for ring $B^d$, among the aforementioned aromatic heterocycles, 5-membered one can be mentioned. Concrete examples thereof include pyrrole, furan, thiophene, pyrazole, imidazole, isoxazole, oxazole, isothiazole, thiazole, triazole, oxadiazole, thiadiazole, and tetrazole. The "5-membered aromatic heterocycle" is preferably pyrazole ring, triazole ring, tetrazole ring, furan ring or the like. More preferred is pyrazole ring.

Examples of the substituent of the "5-membered aromatic heterocycle" include those selected from the aforementioned substituent group A.

Preferred as ring $B^d$ is an unsubstituted pyrazole ring.

Examples of the "substituent" for $R^{2d}$ include those selected from the aforementioned substituent group A. Preferred is an optionally substituted $C_{6-14}$ aryl group (e.g., phenyl), and particularly preferred is unsubstituted phenyl.

Compound (1d) is preferably
(1)
a compound wherein
ring $A^d$ is optionally substituted $C_{3-8}$ cycloalkane, an optionally substituted tetrahydronaphthalene ring, an optionally substituted tetrahydropyridine ring, an optionally substituted piperidine ring, or an optionally substituted azetidine ring;
$R^{1d}$ is a hydrogen atom or a $C_{1-6}$ alkoxy group;
ring $B^d$ is a pyrazole ring optionally further substituted; and
$R^{2d}$ is an optionally substituted phenyl group;
or a salt thereof, more preferably,
(2)
a compound wherein
ring $A^d$ is $C_{3-8}$ cycloalkane, a tetrahydronaphthalene ring, an optionally substituted tetrahydropyridine ring, an optionally substituted piperidine ring, or an optionally substituted azetidine ring;
$R^{1d}$ is a hydrogen atom or a $C_{1-6}$ alkoxy group;
ring $B^d$ is a pyrazole ring; and
$R^{2d}$ is a phenyl group;
or a salt thereof, more preferably,
(3)
a compound wherein
ring $A^d$ is $C_{3-8}$ cycloalkane; a tetrahydronaphthalene ring; a tetrahydropyridine ring optionally substituted by substituent(s) selected from an optionally substituted alkyl group, an optionally substituted alkenyl group, and an optionally substituted heterocyclic group; a piperidine ring optionally substituted by substituent(s) selected from an optionally substituted alkoxy-carbonyl group, an optionally substituted alkyl group, an optionally substituted $C_{6-14}$ aryl group, an optionally substituted heterocyclic group, an optionally substituted alkyl-carbonyl group, an optionally substituted $C_{6-14}$ aryl-carbonyl group, and an optionally substituted arylcarbamoyl group (e.g., phenylcarbamoyl); or an azetidine ring optionally substituted by substituent(s) selected from an optionally substituted heterocyclic group, an optionally substituted $C_{6-14}$ aryl-carbonyl group, an optionally substituted alkyl group, and an optionally substituted $C_{6-14}$ aryl group;
$R^{1d}$ is a hydrogen atom or a $C_{1-6}$ alkoxy group;
ring $B^d$ is a pyrazole ring; and
$R^{2d}$ is a phenyl group;
or a salt thereof, more preferably,
(4)
a compound of the above-mentioned (3) wherein
ring $A^d$ is
(A) $C_{3-8}$ cycloalkane (e.g., cyclopropane, cyclobutane, cyclopentane, cyclohexane),
(B) a tetrahydronaphthalene ring,
(C) a tetrahydropyridine ring optionally substituted by substituent(s) selected from (a) a $C_{1-6}$ alkyl group (e.g., methyl), (b) a $C_{1-6}$ alkenyl group (e.g., propenyl), (c) a $C_{1-6}$ alkyl group substituted by a phenyl group optionally substituted by a $C_{1-6}$ alkoxy group (e.g., benzyl, methoxybenzyl), and (d) a pyridyl group substituted by a halogen atom (e.g., chloropyridyl),
(D) a piperidine ring optionally substituted by substituent(s) selected from (a) a naphthyl group, (b) a thiazolyl group, (c) a benzofuranyl group, (d) a dihydrobenzofuranyl group, (e) a tetrahydropyranyl group, (f) a thienyl group substituted by a halogen atom or a $C_{1-6}$ alkylcarbonyl group (e.g., acetylthienyl), (g) a methylenedioxyphenyl group substituted by a halogen atom (e.g., fluorine), (h) a benzothiazolyl group optionally substituted by a $C_{1-6}$ alkyl group (e.g., methylbenzothiazolyl, benzothiazolyl), (i) a $C_{1-6}$ alkylcarbonyl group (e.g., acetyl), (j) a $C_{1-6}$ alkoxycarbonyl group substituted by $C_{1-6}$ alkyl (t-butoxycarbonyl), (k) $C_{1-6}$ alkyl optionally substituted by a phenyl group (e.g., methyl, benzyl, isopropyl), (l) a phenylcarbonyl group optionally substituted by a halogen atom (e.g., fluorine) (e.g., phenylcarbonyl, fluorophenylcarbonyl), (m) a carbamoyl group mono-substituted by a phenyl group (e.g., phenylcarbamoyl), (n) a pyridyl group optionally substituted by substituent(s) selected from a halogen atom (e.g., chlorine, fluorine), a cyano group, and a $C_{1-6}$ alkyl group substituted by a halogen atom (e.g., fluorine) (e.g., pyridyl, chloropyridyl, cyanopyridyl, trifluoromethylpyridyl), and (o) a phenyl group optionally substituted by substituent(s) selected from a halogen atom (e.g., fluorine, chlorine), a $C_{1-6}$ alkyl optionally substituted by a halogen atom (e.g., methyl), $C_{1-6}$ alkoxy optionally substituted by a halogen atom (e.g., fluorine) (e.g., methoxy), a cyano group, a $C_{1-6}$ alkylcarbonyl group (e.g., acetyl), a $C_{1-6}$ alkylsulfonyl group (e.g., methylsulfonyl), a sulfur atom substituted by 1-5 halogen atoms (e.g., fluorine), and an amino group di-substituted by a $C_{1-6}$ alkyl group (e.g., methyl) (e.g., phenyl, methylphenyl, acetylphenyl, cyanophenyl, fluorophenyl, difluorophenyl, dichlorophenyl, difluoromethoxyphenyl, trifluoromethoxyphenyl, trifluoromethylphenyl, pentafluorosulfanylphenyl, methylsulfonyl, methoxyphenyl, dimethylaminophenyl, chlorothiophenyl), or
(E) an azetidine ring substituted by substituent(s) selected from (a) a phenyl group, (b) a phenylcarboxy group, (c) a pyridyl group substituted by a $C_{1-6}$ alkyl group (e.g., methyl) substituted by a halogen atom (e.g., fluorine) (e.g., trifluoromethylpyridyl), and (d) a $C_{1-6}$ alkyl group di-substituted by a phenyl group (e.g., diphenylmethyl); or a salt thereof.

[Compound (1e)]
Compound (1), which is a compound represented by the following formula (1e) or a salt thereof.

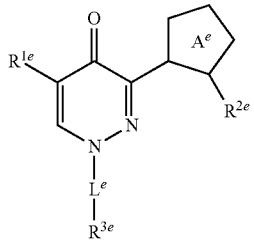

(1e)

wherein $R^{1e}$ is a $C_{1-6}$ alkoxy group; $R^{3e}$ is an optionally substituted $C_{1-6}$ alkyl group, an optionally substituted 3- to 6-membered hydrocarbon ring group, or an optionally substituted 5- to 10-membered heterocyclic group; $L^e$ is an optionally substituted $C_{1-3}$ alkylene group or a sulfonyl group; ring $A^e$ is a 5-membered aromatic heterocycle optionally further substituted; and $R^{2e}$ is a substituent.

As the substituent of the "optionally substituted $C_{1-6}$ alkyl group" for $R^{3e}$, substituent selected from the aforementioned substituent group B can be mentioned. Preferred is a halogen atom (e.g., fluorine).

As the "3- to 6-membered hydrocarbon ring group" of the "optionally substituted 3- to 6-membered hydrocarbon ring group" for $R^{3e}$, among the aforementioned hydrocarbon ring groups, 3- to 6-membered one can be mentioned. The "3- to 6-membered hydrocarbon ring group" is preferably a $C_{3-7}$ cycloalkyl group (e.g., cyclopropyl, cyclobutyl, cyclohexyl), a phenyl group or the like.

Examples of the substituent of the "3- to 6-membered hydrocarbon ring group" include those selected from the aforementioned substituent group A. As the substituent, preferred is substituent selected from the group consisting of
[substituent group A-2]
(a) cyano group;
(b) optionally esterified carboxy group [e.g., optionally substituted alkoxy-carbonyl group, optionally substituted $C_{6-14}$ aryloxy-carbonyl group];
(c) optionally substituted alkyl group;
(d) optionally substituted $C_{6-14}$ aryl group; and
(e) optionally substituted alkoxy group.

As the "5- to 10-membered heterocyclic group" of the "optionally substituted 5- to 10-membered heterocyclic group" for $R^{3e}$, among the aforementioned heterocyclic groups, 5- to 10-membered one can be mentioned. Concrete examples thereof include for example, tetrahydropyranyl group, piperidinyl group, tetrahydrofuranyl group, pyrrolidinyl group, morpholinyl group, quinolinyl group, isoquinolinyl group, oxetanyl group, pyridyl group, furyl group, azetidinyl group, pyrazolyl group, azepanyl group and the like. The "5- to 10-membered heterocyclic group" is preferably tetrahydropyranyl group, piperidinyl group, tetrahydrofuranyl group, pyrrolidinyl group, morpholinyl group, quinolinyl group, isoquinolinyl group, oxetanyl group, pyridyl group, furyl group and the like.

Examples of the substituent of the "5- to 10-membered heterocyclic group" include those selected from the aforementioned substituent group A. As the substituent, preferred are substituent selected from the group consisting of an optionally substituted alkoxy-carbonyl group, an optionally substituted alkyl group, and an optionally substituted alkoxy group.

Preferred as $R^{3e}$ is a $C_{3-7}$ cycloalkyl group (e.g., cyclopropyl, cyclobutyl, cyclohexyl) or a phenyl group, each of which is optionally substituted by substituent(s) selected from the group consisting of cyano, an optionally esterified carboxy group [e.g., optionally substituted alkoxy-carbonyl group, optionally substituted $C_{6-14}$ aryloxy-carbonyl group], an optionally substituted alkyl group, an optionally substituted $C_{6-14}$ aryl group, and an optionally substituted alkoxy group; or a tetrahydropyranyl group, a piperidinyl group, a tetrahydrofuranyl group, a pyrrolidinyl group, a morpholinyl group, a quinolinyl group, an isoquinolinyl group, an oxetanyl group, a pyridyl group, or a furyl group, which is optionally substituted by substituent(s) selected from the group consisting of an optionally substituted alkoxy-carbonyl group, an optionally substituted alkyl group, and an optionally substituted alkoxy group.

Examples of the substituent of the "optionally substituted $C_{1-3}$ alkylene group" for $L^e$ include substituent selected from the aforementioned substituent group B. Preferred is an oxo group.

Preferred as $L^e$ is an unsubstituted $C_{1-3}$ alkylene group.

As the "5-membered aromatic heterocycle" of the "5-membered aromatic heterocycle optionally further substituted" for ring $A^e$, among the aforementioned aromatic heterocycles, 5-membered one can be mentioned. The "aromatic heterocycle" is preferably a pyrazole ring, a triazole ring, a tetrazole ring, a furan ring or the like. It is preferably a pyrazole ring. Examples of the substituent of the "5-membered aromatic heterocycle" include those selected from the aforementioned substituent group A.

Preferred as ring $A^e$ is a pyrazole ring free of further substituent.

Examples of the "substituent" for $R^{2e}$ include those selected from the aforementioned substituent group A. Preferred is an optionally substituted $C_{6-14}$ aryl group (e.g., phenyl), and particularly preferred is unsubstituted phenyl.

Compound (1e) is preferably
(1)
a compound wherein
$R^{1e}$ is a $C_{1-6}$ alkoxy group;
$R^{3e}$ is an optionally substituted $C_{1-6}$ alkyl group, an optionally substituted $C_{3-7}$ cycloalkyl group, an optionally substituted tetrahydropyranyl group, an optionally substituted piperidyl group, an optionally substituted tetrahydrofuranyl group, an optionally substituted pyrrolidyl group, an optionally substituted morpholinyl group, an optionally substituted quinolinyl group, an optionally substituted isoquinolinyl group, an optionally substituted oxetanyl group, an optionally substituted phenyl group, an optionally substituted pyridyl group, or an optionally substituted furyl group;
$L^e$ is an optionally substituted $C_{1-3}$ alkylene group or a sulfonyl group;
ring $A^e$ is a pyrazole ring optionally further substituted; and
$R^{2e}$ is an optionally substituted phenyl group;
or a salt thereof, more preferably,
(2)
a compound wherein
$R^{1e}$ is a $C_{1-6}$ alkoxy group (e.g., methoxy);
$R^{3e}$ is an optionally substituted $C_{1-6}$ alkyl group (e.g., trifluoromethyl), a $C_{3-7}$ cycloalkyl group (e.g., cyclopropyl, cyclobutyl, cyclohexyl), a tetrahydropyranyl group, a piperidyl group, a tetrahydrofuranyl group, a pyrrolidyl group, a morpholinyl group, a quinolinyl group, an isoquinolinyl group, an optionally substituted oxetanyl group, an optionally substituted phenyl group, an optionally substituted pyridyl group, of an optionally substituted furyl group;

$L^e$ is an optionally substituted $C_{1-3}$ alkylene group or a sulfonyl group;
ring $A^e$ is a pyrazole ring; and
$R^{2e}$ is a phenyl group;
or a salt thereof, more preferably, (3)

a compound of the above-mentioned (2), wherein
$R^{3e}$ is (a) a $C_{1-6}$ alkyl group substituted by a halogen atom (e.g., trifluoromethyl),
(b) a $C_{3-7}$ cycloalkyl group (e.g., cyclopropyl, cyclobutyl, cyclohexyl),
(c) a tetrahydropyranyl group,
(d) a piperidyl group,
(e) a tetrahydrofuranyl group,
(f) a pyrrolidyl group,
(g) a morpholinyl group,
(h) a quinolinyl group,
(i) an isoquinolinyl group,
(j) an oxetanyl group substituted by a $C_{1-6}$ alkyl (e.g., methyloxetanyl),
(k) a phenyl group optionally substituted by 1 to 3 substituents selected from a $C_{1-6}$ alkyl group substituted by a halogen atom (e.g., trifluoromethyl), a $C_{1-6}$ alkoxy group (e.g., methoxy), a $C_{1-6}$ alkoxycarbonyl group (e.g., methoxycarbonyl), a cyano group, and a phenyl group,
(l) a pyridyl group optionally substituted by 1 to 3 substituents selected from a $C_{1-6}$ alkyl group (e.g., methyl), a $C_{1-6}$ alkoxycarbonyl group (e.g., methoxycarbonyl), and a $C_{1-6}$ alkoxy group substituted by a halogen atom (e.g., trifluoroethoxy), or
(m) a furyl group substituted by substituent(s) selected from $C_{1-6}$ alkyl substituted by a halogen atom (e.g., trifluoromethyl), and a $C_{1-6}$ alkoxycarbonyl group (e.g., ethoxycarbonyl); and
$L^e$ is a $C_{1-3}$ alkylene group optionally substituted by an oxo group (e.g., ethylene optionally substituted by an oxo group) or a sulfonyl group;
or a salt thereof.

[Compound (1f)]

Compound (1), which is a compound represented by the following formula (1f) or a salt thereof.

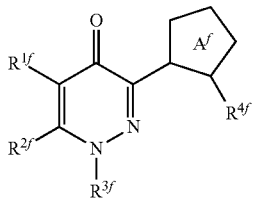

(1f)

wherein $R^{1f}$ is an optionally substituted $C_{1-6}$ alkoxy group; $R^{2f}$ is a hydrogen atom or a substituent; $R^{3f}$ is an optionally substituted $C_{1-6}$ alkyl group or an optionally substituted cyclic group; ring $A^f$ is a non-aromatic 5-membered heterocycle optionally further substituted; and $R^{4f}$ is an optionally substituted $C_{1-6}$ alkyl group or an optionally substituted cyclic group.

Examples of the substituent of the "optionally substituted $C_{1-6}$ alkoxy group" for $R^{1f}$ include substituent selected from the aforementioned substituent group B.

Preferred as $R^{1f}$ is an unsubstituted $C_{1-6}$ alkoxy group (e.g., methoxy group).

Examples of the "substituent" for $R^{2f}$ include those selected from the aforementioned substituent group A.

Preferred as $R^{2f}$ is a hydrogen atom.

Examples of the substituent of the "optionally substituted $C_{1-6}$ alkyl group" for $R^{3f}$ include substituent selected from the aforementioned substituent group B.

Examples of the "cyclic group" of the "optionally substituted cyclic group" for $R^{3f}$ include the aforementioned "heterocyclic group", "non-aromatic cyclic hydrocarbon group", and "aromatic cyclic hydrocarbon group".

The "cyclic group" is preferably a phenyl group, a pyridyl group, a piperidinyl group, a pyrazolyl group or the like. More preferred is a phenyl group.

Examples of the substituent of the "cyclic group" include those selected from the aforementioned substituent group A. Preferred is an optionally substituted alkyl group, and particularly preferred is an alkyl group optionally substituted by a halogen atom (e.g., trifluoromethyl).

$R^{3f}$ is preferable a phenyl group substituted by an alkyl group optionally substituted by a halogen atom (e.g., trifluoromethyl).

As the "non-aromatic 5-membered heterocycle" of the "non-aromatic 5-membered heterocycle optionally further substituted" for ring $A^f$, among the aforementioned non-aromatic heterocycles, 5-membered one can be mentioned. The "non-aromatic 5-membered heterocycle" is preferably a dihydroimidazole ring, a pyrrolidine ring, a tetrahydrofuran ring, a cyclopentane ring or the like. More preferred is a dihydroimidazole ring.

Examples of the substituent of the "non-aromatic heterocycle" include those selected from the aforementioned substituent group A. Preferred are an oxo group and an optionally substituted alkyl group (e.g., methyl).

Preferred as ring $A^f$ is a dihydroimidazole ring substituted by an oxo group and an optionally substituted alkyl group (e.g., methyl).

Examples of the substituent of the "optionally substituted $C_{1-6}$ alkyl group" for $R^{4f}$ include substituent selected from the aforementioned substituent group B.

Examples of the "optionally substituted cyclic group" for $R^{4f}$ include the aforementioned "heterocyclic group" and "hydrocarbon ring group". The "cyclic group" is preferably a phenyl group, a pyridyl group, a $C_{3-7}$ cycloalkyl group, a piperidinyl group or the like. Preferred is a phenyl group.

Examples of the substituent of the "cyclic group" include those selected from the aforementioned substituent group A.

$R^{4f}$ is preferably an unsubstituted phenyl group.

Compound (1f) is preferably (1)

a compound wherein
$R^{1f}$ is an optionally substituted $C_{1-6}$ alkoxy group;
$R^{2f}$ is a hydrogen atom or a substituent;
$R^{3f}$ is an optionally substituted $C_{1-6}$ alkyl group or an optionally substituted cyclic group;
ring $A^f$ is a non-aromatic 5-membered heterocycle optionally further substituted; and
$R^{4f}$ is an optionally substituted $C_{1-6}$ alkyl group or an optionally substituted cyclic group;
or a salt thereof, more preferably, (2)

a compound wherein
$R^{1f}$ is a $C_{1-6}$ alkoxy group (e.g., methoxy);
$R^{2f}$ is a hydrogen atom;
$R^{3f}$ is a phenyl group substituted by a $C_{1-6}$ alkyl group substituted by a halogen atom (e.g., trifluoromethylphenyl); ring $A^f$ is a dihydroimidazole ring further substituted by substituent(s) selected from an oxo group and a $C_{1-6}$ alkyl group; and
$R^{4f}$ is a phenyl group;
or a salt thereof.

Compound (1ˣ) or compound (1) is preferably the above-mentioned compounds (Ia)-compound (If), more preferably compound (Ia), (Ic), (Id) or (Ie), particularly preferably compound (Id) or (Ie).

When the compound (1ˣ) or compound (1) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, potassium salt, etc.) and alkali earth metal salts (e.g., calcium salts, magnesium salts, barium salts, etc.) and ammonium salts are preferable. In the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (1ˣ) or compound (1) includes isomers such as tautomers, optical isomers, stereoisomers, position isomers and rotational isomers, one of the other isomers or mixture are also included in the compound of the present invention. Further, if the compound (1ˣ) or compound (1) has an optical isomer, the optical isomer separated from the racemate is included in the compound (1ˣ) or compound (1).

The compound (1ˣ) or compound (1) can be obtained in the crystal form. Either single crystalline form or crystalline mixture can be included in the compound (1ˣ) or compound (1).

The compound (1ˣ) or compound (1) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method.

The compound (1ˣ) or compound (1) may be a solvate (e.g., hydrate) or a non-solvate and both are included in the compound (1ˣ) or compound (1).

Compounds labeled with or substituted by isotopes (e.g., $^2H$, $^3H$, $^{11}C$, $^{14}C$, $^{18}F$, $^{35}S$, $^{125}I$, etc.) are also included in compound (1ˣ) or compound (1). Compound (1ˣ) and compound (1) labeled with or substituted by isotopes can be used as, for example, a tracer used for Positron Emission Tomography (PET) (PET tracer), and are useful in the field of medical diagnosis and the like.

A prodrug of compound (1ˣ) or compound (1) means a compound which is converted to compound (1ˣ) or compound (1) by a reaction due to enzyme, gastric acid, etc. under the physiological conditions in the living body, that is, a compound which is converted to compound (1ˣ) or compound (1) by enzymatical oxidation, reduction, hydrolysis, etc. according to an enzyme; a compound which is converted to compound (1ˣ) or compound (1) by hydrolysis etc. due to gastric acid, etc.

A prodrug of compound (1ˣ) or compound (1) may be a compound obtained by subjecting an amino group in compound (1ˣ) or compound (1) to an acylation, alkylation or phosphorylation (e.g., a compound obtained by subjecting an amino group in compound (1) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (1ˣ) or compound (1) to an acylation, alkylation, phosphorylation or boration (e.g., a compound obtained by subjecting an hydroxy group in compound (1ˣ) or compound (1) to an acetylation, palmitoylation, propanoylation, pivaloylation, succinylation, fumarylation, alanylation, dimethylaminomethylcarbonylation, etc.); a compound obtained by subjecting a carboxyl group in compound (1ˣ) or compound (1) to an esterification or amidation (e.g., a compound obtained by subjecting a carboxyl group in compound (1) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (1ˣ) or compound (1) by a method known per se. A prodrug for compound (1ˣ) or compound (1) may also be one which is converted into compound (1ˣ) or compound (1) under a physiological condition, such as those described in IYAKUHIN no KAIHATSU (Development of Pharmaceuticals), Vol. 7, Design of Molecules, p. 163-198, Published by HIROKAWA SHOTEN (1990).

[Production Method]

The compound of the present invention and the compound as raw materials can be manufactured by the known means, for example, by the methods shown in the following schemes. Hereinafter, "room temperature" indicates a temperature generally ranging from 0 to 35° C. and "a low temperature" indicates a temperature generally from −78 to 0° C.

The symbols used for the compounds in the reaction schemes indicate the same meanings as mentioned above. In this specification, a methyl group ($CH_3$) is sometimes abbreviated as Me. The compounds in the schemes can include salts thereof in the cases when salts can be formed and such salts are similar to the salts of the compound (1). Further, the compound obtained in each process can be used directly in the form of a reaction mixture or as a crude product in the following reactions. However, it can be isolated from the reaction mixture according to the ordinary method. The product itself can be easily purified by the known means of isolation such as extraction, concentration, neutralization, filtration, distillation, recrystallization and chromatography. Alternatively, if the compound in the schemes is commercially available, a commercial product can be used directly and in addition, those which are manufactured by the known methods or by a comparable method can be used. If the compound as a raw material contains amino, carboxy, hydroxyl or heterocyclic group, the group can be protected by a protective group that is generally used in the peptide chemistry. In this case, after reacting, if desirable, target compound can be obtained by removing the protective group. The protective group can be introduced or removed by the known methods, for example, based on the methods described in "Protective Groups in Organic Synthesis, 3$^{rd}$ Edition" (by Theodora W. Greene, Peter G. M. Wuts, published in 1999 by Wiley-Interscience Corporation).

In these production methods, conversions of each substituents can be carried out according to a method known per se, for example, the method described in "Comprehensive Organic Transformations" (by Richard C. Larock, published in 1999 by Wiley-VCH).

The following respective processes can be carried out without a solvent or the compound as a raw material can be dissolved or suspended in an appropriate solvent prior to the reaction. In this case, one kind of solvent can be used independently or two or more solvents can be combined at an appropriate ratio. Specific examples of the solvents to be used in the production methods for the compound of the present invention are given as follows:

Alcohols: methanol, ethanol, 1-propanol, 2-propanol, tert-butyl alcohol, 2-methoxyethanol, etc.

Ethers: diethyl ether, diisopropyl ether, diphenyl ether, tetrahydrofuran, 1,4-dioxane, 1,2-dimethoxyethane, etc.

Aromatic hydrocarbons: benzene, chlorobenzene, toluene, xylene, etc.

Saturated hydrocarbons: cyclohexane, hexane, etc.

Amides: N,N-dimethylformamide, N,N-dimethylacetamide, hexamethylphosphoric triamide, etc.

Halogenated hydrocarbons: dichloromethane, chloroform, carbon tetrachloride, 1,2-dichloroethane, etc.

Nitriles: acetonitrile, propionitrile, etc.

Sulfoxides: dimethyl sulfoxide, etc.

Aromatic organic bases: pyridine, lutidine, etc.

Acid anhydrides: acetic anhydride, trifluoroacetic anhydride, etc.

Organic acids: formic acid, acetic acid, propionic acid, trifluoroacetic acid, methanesulfonic acid, etc.

Inorganic acids: hydrochloric acid, sulfuric acid, etc.

Esters: methyl acetate, ethyl acetate, butyl acetate, etc.

Ketones: acetone, methyl ethyl ketone, etc.

Specific examples of bases or deoxidizers that are used in the production methods for the compound of the present invention are given as follows:

Inorganic bases: sodium hydroxide, potassium hydroxide, lithium hydroxide, magnesium hydroxide, etc.

Basic salts: sodium carbonate, potassium carbonate, cesium carbonate, calcium carbonate, sodium hydrogen carbonate, sodium acetate, ammonium acetate, etc.

Organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, etc.

Metal alkoxides: sodium methoxide, sodium ethoxide, potassium tert-butoxide, etc.

Alkali metal hydrides: sodium hydride, potassium hydride, etc.

Metal amides: sodium amide, lithium diisopropylamide, lithium hexamethyldisilazide, etc.

Organolithium reagents: methyl lithium, n-butyl lithium, sec-butyl lithium, tert-butyl lithium, etc.

Specific examples of acids or acid catalysts that are used in the production methods for the compound of the present invention are given as follows:

Inorganic acids: hydrochloric acid, sulfuric acid, nitric acid, hydrobromic acid, phosphoric acid, etc.

Organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.

Lewis acids: trifluoroboron ether complex, zinc iodide, anhydrous aluminum chloride, anhydrous zinc chloride, anhydrous iron chloride, etc.

Compounds (1a), (1a'), (1b), (1c), (1d), (1d'), (1d"), (1e) and (1f) encompassed in compound (1) or compound (1$^x$) can be synthesized by, for example, production method A1, production method A2, production method B, production method C, production method D, production method E, production method F, production method G and the like explained below, or a method analogous to these production methods.

Unless otherwise specified, the symbols in each formula in the reaction schemes have the same meanings as those mentioned above.

[Production Method A1]

-continued

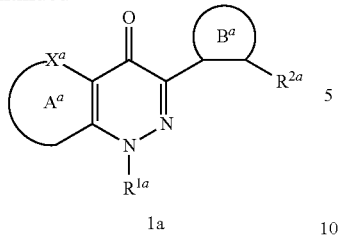

1a

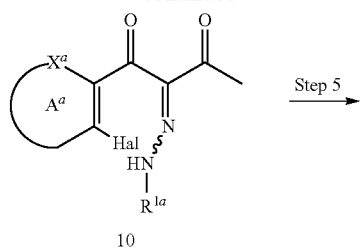

10 wherein ring $A^a$ is an optionally substituted 5- to 7-membered heterocycle; $X^a$ is an oxygen atom, a sulfur atom or —$NR^a$— ($R^a$ is a hydrogen atom or a substituent); $X^{a2}$ is a substituent; $R^{1a}$ is a substituent; ring $B^a$ is a nitrogen-containing heterocycle optionally further substituted; $R^{2a}$ is a substituent; and Hal is a halogen atom.

Examples of the "substituent" for $X^{a2}$ include those selected from the aforementioned substituent group A. The definition of each of other terms is as mentioned above.

The starting material of production method A1 can be produced by a method known per se or a method analogous thereto. In addition, a commercially available product may be used as a starting material.

Where necessary, ring $A^a$ of an intermediate or resulting product can be hydrogenized. To be specific, it is produced by reacting in the presence of a catalyst such as palladium on carbon and the like under a hydrogen atmosphere. The amount of the palladium on carbon to be used is about 0.01-1 equivalent, preferably 0.01-0.1 equivalent, relative to an intermediate or resulting product to be the reaction substrate.

While the solvent is not particularly limited as long as the reaction proceeds, for example, alcohols and acetic acid are preferable. It is desirable to carry out the reaction generally under ice-cooling, at room temperature or heating under reflux conditions, and 0° C.-150° C. is preferable. The reaction time is generally 0.5-48 hr, preferably 0.5-24 hr.

The starting material of production method A1 can be produced by a method known per se or a method analogous thereto. In addition, a commercially available product may be used as a starting material.

[Production Method A2]

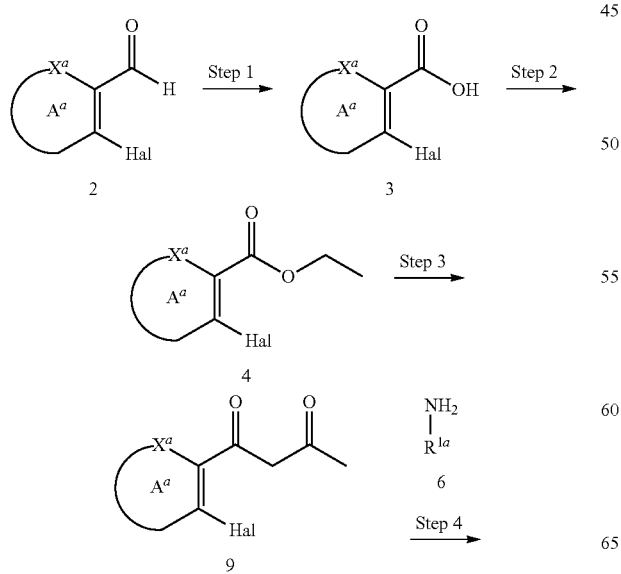

wherein $A^a$, $X^a$, $R^{1a}$, $R^{2a}$ and Hal are as defined in production method A1.

Production Method A2 is a production method of compound (1a') wherein a partial structural formula

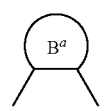

of compound (1a) is

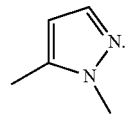

The starting material of production method A2 can be produced by a method known per se or a method analogous thereto. In addition, a commercially available product may be used as a starting material.

[Production Method B]

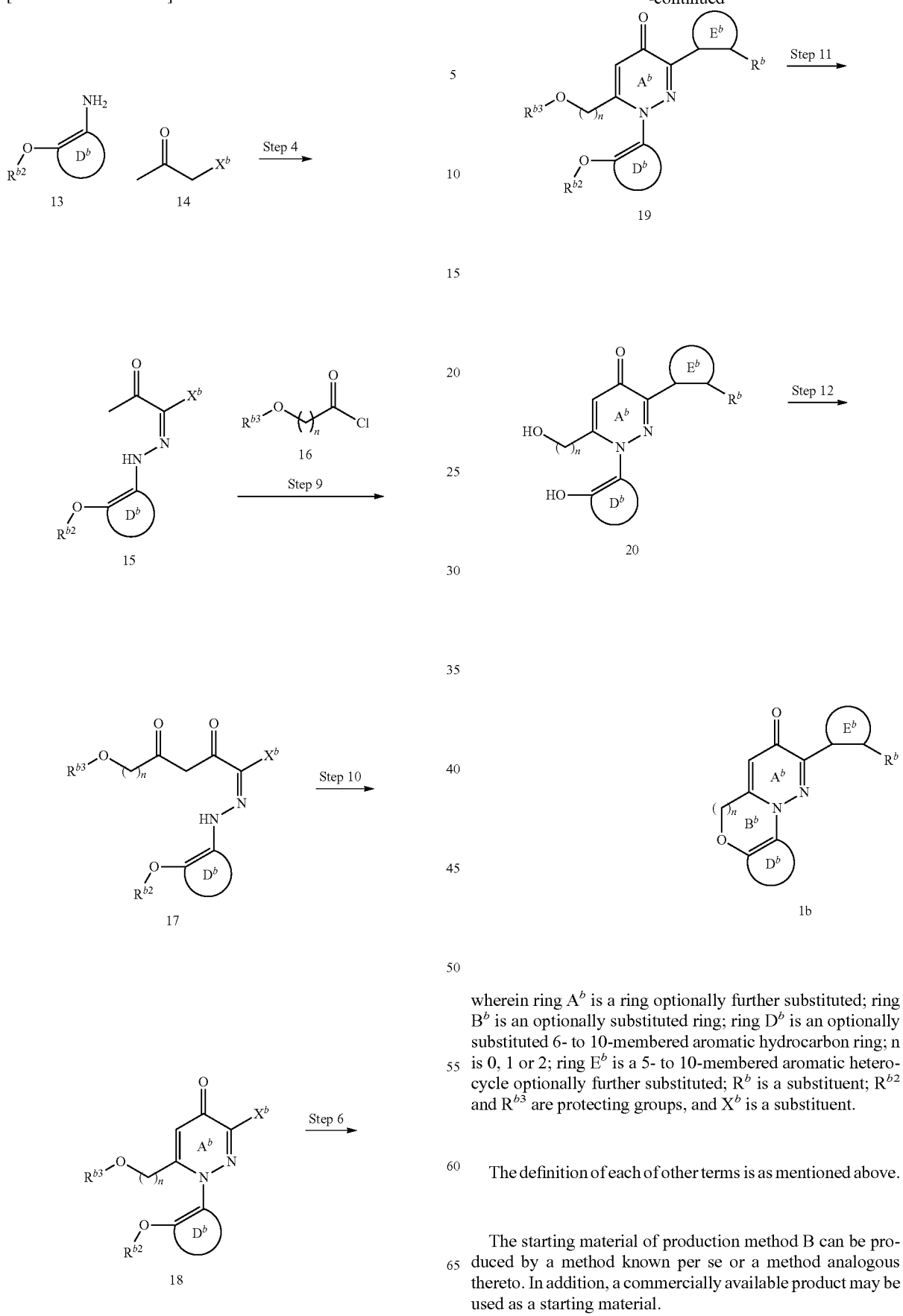

wherein ring $A^b$ is a ring optionally further substituted; ring $B^b$ is an optionally substituted ring; ring $D^b$ is an optionally substituted 6- to 10-membered aromatic hydrocarbon ring; n is 0, 1 or 2; ring $E^b$ is a 5- to 10-membered aromatic heterocycle optionally further substituted; $R^b$ is a substituent; $R^{b2}$ and $R^{b3}$ are protecting groups, and $X^b$ is a substituent.

The definition of each of other terms is as mentioned above.

The starting material of production method B can be produced by a method known per se or a method analogous thereto. In addition, a commercially available product may be used as a starting material.

[Production Method C]

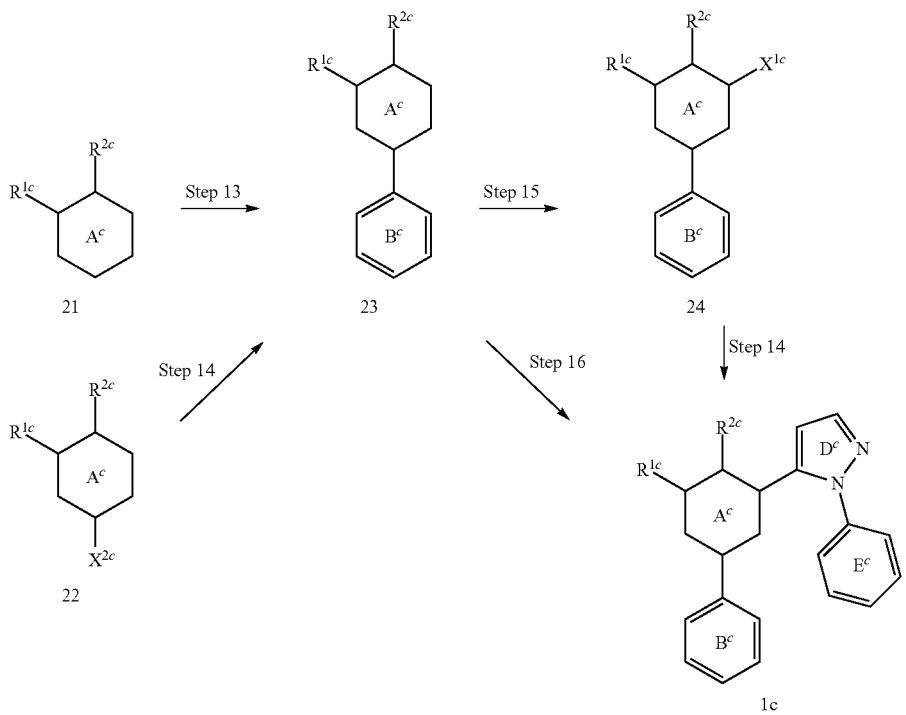

wherein ring $A^c$ is a 6-membered heterocycle optionally further substituted; ring $B^c$ is an optionally substituted 6-membered aromatic ring; $R^{1c}$ is a hydrogen atom or a substituent (excluding an aromatic ring group and —CO—Rx ($R^x$ is a substituent)); $R^{2c}$ is a hydrogen atom, a hydroxy group, an oxo group or an optionally substituted $C_{1-6}$ alkoxy group, ring $D^c$ is a pyrazole ring optionally further substituted; ring $E^c$ is an optionally substituted benzene ring, and $X^{1c}$ and $X^{2c}$ are halogen atoms or triflate groups.

The definition of each term is as mentioned above.

Compound (21) and compound (22), which are starting materials of production method C, can be produced by a method known per se or a method analogous thereto. In addition, compound (23) may be used as a starting material. Compound (23) can be produced by the method described in steps A)-B) of Example 12, step A) of Example 13, step A) of Example 15, steps A)-C) of Example 19, or step A) of Example 21, or a method analogous thereto. In addition, a commercially available product may be used as a starting material.

A compound wherein a partial structural formula

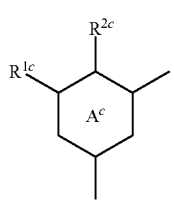

of compound (1c) is

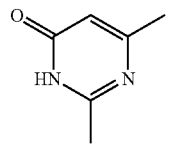

can be produced by the method described in Example 17 or a method analogous thereto.

A compound wherein a partial structural formula

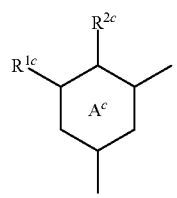

of compound (1c) is

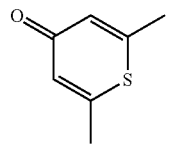

can be produced by the method described in Example 140 or a method analogous thereto.

A compound wherein a partial structural formula

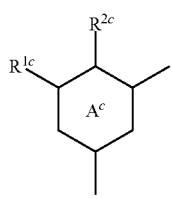

of compound (1c) is

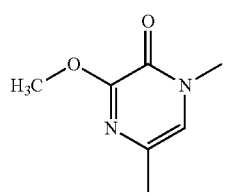

can be produced by the method described in Example 141 or a method analogous thereto.

[Production Method D]

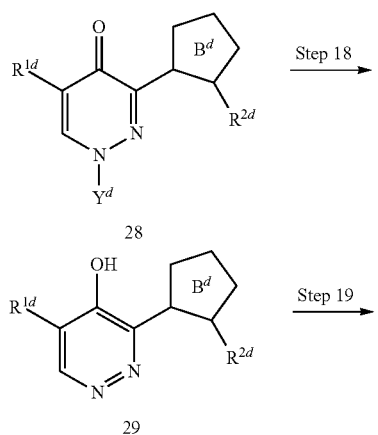

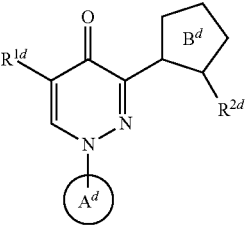
1d wherein ring $A^d$ is an optionally substituted 3- to 10-membered non-aromatic ring, ring $B^d$ is a 5-membered aromatic heterocycle optionally further substituted, $R^{1d}$ is a hydrogen atom or an alkoxy group, $R^{2d}$ is a substituent, $R^{3d}$ is a hydrogen atom or an optionally substituted hydrocarbon group (an alkyl group, an alkenyl group, an alkynyl group, a $C_{6-14}$ aryl group etc.), wherein two $R^{3d}$s may form a 4,4,5,5-tetramethyl-1,3,2-dioxaborolane ring and the like together with each adjacent oxygen atom, $X^d$ is a halogen atom (F, Cl, Br, I etc.), and $Y^d$ is a protecting group (a benzyl group etc.).

The definition of each term is as mentioned above.

The starting material of production method D can be produced by a method known per se or a method analogous thereto. In addition, a commercially available product may be used as a starting material.

[Production Method E]

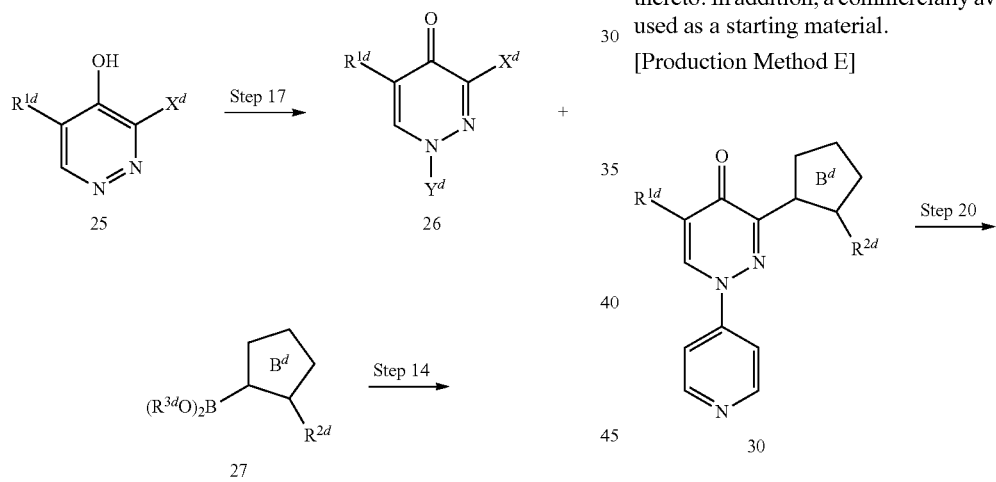

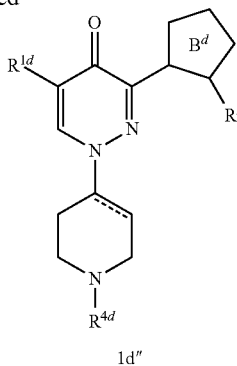

1d″ wherein $R^{4d}$ is a substituent, and other symbols are as defined in production method D.

Examples of the "substituent" for $R^{4d}$ include those selected from the aforementioned substituent group A. The definition of each of other terms is as mentioned above.

Of the compounds encompassed in compound (1d), a compound wherein ring $A^d$ is a piperidine ring or a tetrahydropyridine ring is indicated as compound (1d'), and a compound wherein nitrogen atom of the piperidine ring or tetrahydropyridine ring of compound (1d') is modified is indicated as compound (1d″). Compounds (1d') and (1d″) can be synthesized by production method D, and can also be synthesized by production method E. In addition, the regioisomer of piperidine can also be synthesized by production method D, production method E, or a method analogous thereto.

The starting material of production method E can be produced by a method known per se or a method analogous thereto.

[Production Method F]

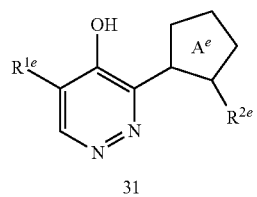

31

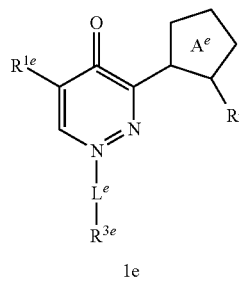

1e wherein ring $A^e$ is a 5-membered aromatic heterocycle optionally further substituted, $R^{1e}$ is a hydrogen atom or an alkoxy group, $R^{2e}$ is a substituent, $R^{3e}$ is an optionally substituted $C_{1-6}$ alkyl group, an optionally substituted 3- to 6-membered hydrocarbon ring group, or an optionally substituted 5- to 10-membered heterocyclic group, and $L^e$ is an optionally substituted $C_{1-3}$ alkylene group or a sulfonyl group.

The definition of each term is as mentioned above.

The starting material of production method F can be produced by a method known per se or a method analogous thereto, the synthesis method of compound (29) of production method D or a method analogous thereto. In addition, a commercially available product may be used as a starting material.

[Production Method G]

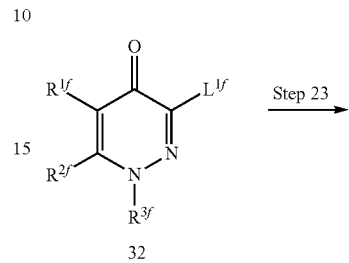

32

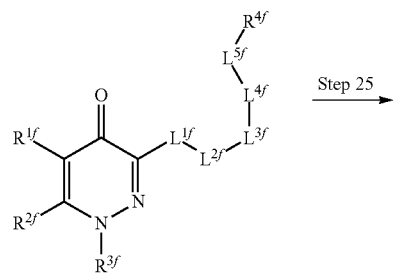

33

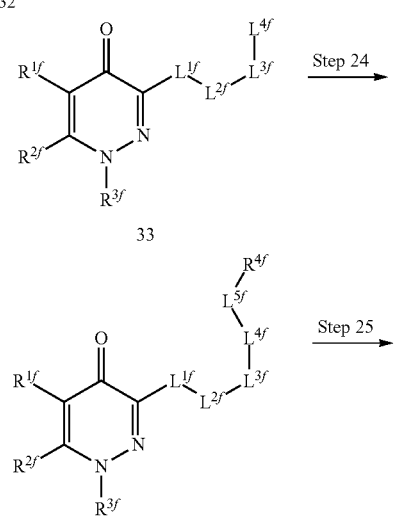

34

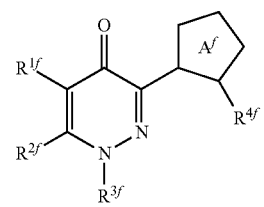

1f wherein $R^{1f}$ is an optionally substituted $C_{1-6}$ alkoxy group; $R^{2f}$ is a hydrogen atom or a substituent; $R^{3f}$ is an optionally substituted $C_{1-6}$ alkyl group or an optionally substituted cyclic group, ring $A^f$ is a non-aromatic 5-membered heterocycle optionally further substituted; $R^{4f}$ is an optionally substituted $C_{1-6}$ alkyl group or an optionally substituted cyclic group, and $L^{1f}$, $L^{2f}$, $L^{3f}$, $L^{4f}$ and $L^{5f}$ are optionally substituted one atom linkers.

Examples of the "optionally substituted one atom linker" for $L^{1f}$, $L^{2f}$, $L^{3f}$, $L^{4f}$ or $L^{5f}$ include —CO—, —NH—, —C(CH$_3$)$_2$— and the like.

The definition of each term is as mentioned above.

The starting material of production method G can be produced by a method known per se or a method analogous thereto.

In step 1, compound (3) is produced from compound (2), wherein an aqueous solution of sodium chlorite and sodium dihydrogen phosphate is added to compound (2) to allow reaction. The solvent to be used is not particularly limited as long as the reaction proceeds. For example, a mixed solvent of alcohols and water is desirable.

The amount of sodium chlorite to be used is about 1-10 mol, preferably 1-5 mol, relative to 1 mol of compound (2).

The amount of sodium dihydrogen phosphate to be used is about 1-10 mol, preferably 1-5 mol, relative to 1 mol of (2).

It is desirable to carry out the reaction generally under ice-cooling or room temperature conditions, preferably under ice-cooling.

The reaction time is generally 5-48 hr, preferably 10-24 hr.

In step 2, compound (4) is produced from compound (3).

Ethylation can be performed by using ethyl iodide and the like in the presence of a base. Examples of the base include inorganic bases, basic salts, alkali metal hydrides and the like. The solvent is not particularly limited as long as the reaction proceeds. For example, ethers, amides and ketones are desirable.

The amount of ethyl iodide to be used is about 1-10 mol, preferably 1-3 mol, relative to 1 mol of compound (3). The amount of the base to be used is about 1-10 mol, preferably 1-3 mol, relative to 1 mol of compound (3). It is desirable to carry out the reaction generally under ice-cooling or room temperature conditions, preferably under ice-cooling.

The reaction time is generally 1-5 hr, preferably 1-2 hr.

Where necessary, a $C_{1-6}$ alkyl group other than ethyl group may be used. In this case, a reaction similar to the above-mentioned only needs to be performed using the corresponding $C_{1-6}$ alkylhalide.

In step 3, compound (5) or compound (9) is produced from compound (4), wherein a reaction with acetone is performed under basic conditions.

It is advantageous to carry out the reaction in the absence of a solvent or using an inert solvent for the reaction. The solvent is not limited as long as the reaction proceeds but, for example, toluene is preferable.

The amount of the acetone to be used is about 1-10 mol, preferably 2-3 mol, relative to 1 mol of compound (4). Examples of the "base" include metal alkoxides, alkali metal hydrides and the like. The amount of the base to be used is about 1-10 mol, preferably 1-5 mol, relative to 1 mol of compound (4).

It is desirable to carry out the reaction generally at room temperature or under heated conditions, preferably at room temperature.

The reaction time is generally 1-48 hr, preferably 3-10 hr.

In step 4, compound (7), compound (10) or compound (15) is produced by reacting compound (6) or compound (13) with a diazotizing agent to give a diazonium salt, and placing the salt in co-presence with compound (5), compound (9) or compound (14). The starting compound (6) and compound (13) may be commercially available products.

This step can be performed by the method described in Tetrahedron Lett., 2008, 49(14), 2262-2264, or a method analogous thereto. Diazotization can be generally performed in the presence of an acid. The subsequent coupling reaction can be generally performed in the presence of a base.

Examples of the diazotizing agent include alkali metal nitrite such as sodium nitrite, and potassium nitrite and the like; alkyl nitrite ester having a carbon number of 2 to 6 such as t-butyl nitrite, isoamyl nitrite and the like; nitrosyl chloride, nitrosyl sulfuric acid, and nitric oxide and the like. Of these, sodium nitrite is preferable since it can be easily obtained at a low cost. Alkyl nitrite ester is preferable since it increases reactivity. Since alkali metal nitrite is solid at ambient temperature, it may be dissolved in water in advance and then used.

Examples of the "acid" include inorganic acids, organic acids and the like, and they may be used in a mixture.

The amount of the diazotizing agent to be used is about 1-5 mol, preferably 1-2 mol, relative to 1 mol of compound (6) or compound (13). It is desirable to carry out the reaction generally at room temperature or at a low temperature, preferably from −30° C. to 0° C.

The diazotization time is generally 1 min-3 hr, preferably 1 min-1 hr.

It is advantageous to carry out the diazotization reaction in the absence of a solvent or using an inert solvent for the reaction. The solvent to be used is not particularly limited as long as the reaction proceeds but, for example, water is desirable.

The amount of compound (5), compound (9) or compound (14) to be used in the coupling reaction is about 1-5 mol, preferably 1-2 mol, relative to 1 mol of compound (6) or compound (13).

Examples of the "base" include basic salts.

The amount of the "base" to be used generally is 1-10 mol, preferably 2-6 mol, relative to 1 mol of compound (6) or compound (13).

It is advantageous to carry out the coupling reaction in the absence of a solvent or the presence of an inert solvent for the reaction. The solvent to be used is not particularly limited as long as the reaction proceeds but, for example, a mixed solvent of alcohols and water is desirable.

It is desirable to carry out the coupling reaction generally at room temperature or at a low temperature while being cooled in an ice bath.

The reaction time is generally 5 sec-24 hr, preferably 5 sec-1 hr.

In step 5, compound (8) or compound (11) is produced from compound (7) or compound (10), wherein a reaction can be performed in the presence of a base.

As the base, basic salts, organic bases, metal alkoxides or metal amides and the like can be used and potassium carbonate or sodium methoxide is preferable. The amount of the base to be used is about 1-10 mol, preferably 1-3 mol, relative to 1 mol of compound (7) or compound (10). It is advantageous to carry out the reaction using an inert solvent for the reaction. The solvent to be used is not particularly limited as long as the reaction proceeds but, for example, ethers and amides are desirable. It is desirable to carry out the reaction generally at room temperature or heating under reflux conditions, preferably at room temperature.

The reaction time is generally 1-24 hr, preferably 2-4 hr.

In step 6, compound (1a) or compound (19) is produced from compound (8) or compound (18).

This step can be performed by the method described in Journal of Heterocyclic Chemistry, 1981, 18, 333-334, or a method analogous thereto.

For example, when ring $B^a$ or ring $E^b$ is a pyrazole ring, step 7 and step 8 to be explained later are performed without isolation of intermediate.

In step 7, compound (12) is produced from compound (11), wherein a reaction can be performed in the presence of N,N-dimethylformamide dimethyl acetal and the like as a solvent.

This step can be performed by the method described in Journal of Heterocyclic Chemistry, 1981, 18, 333-334, or a method analogous thereto.

It is desirable to carry out the reaction generally heating under reflux conditions, preferably 100° C.-150° C.

The reaction time is generally 1-10 hr, preferably 1-5 hr.

In step 8, compound (1a') is produced by placing compound (12) in co-presence with a hydrazine derivative.

The amount of the hydrazine derivative to be used is about 1-10 mol, preferably 1-3 mol, relative to 1 mol of compound (12).

It is advantageous to carry out the present reaction in the absence of a solvent or in the presence of an inert solvent for the reaction. The solvent to be used is not particularly limited as long as the reaction proceeds but, for example, alcohols, organic acids and a mixed solvent thereof are desirable.

It is desirable to carry out the reaction generally under ice-cooling, at room temperature or heating under reflux conditions, and 0° C.-150° C. is preferable.

The reaction time is generally 0.1-10 hr, preferably 0.5-5 hr.

This step can be performed by the method described in Journal of Heterocyclic Chemistry, 1981, 18, 333-334, or a method analogous thereto.

In step 9, compound (17) is produced by placing compound (15) in co-presence with compound (16) wherein a reaction can be performed under basic conditions.

This step can be performed by the method described in Indian J. Chem. Sect. B 1991, 30B, 932-935, or a method analogous thereto. It is advantageous to carry out the reaction using an inert solvent for the reaction. The solvent to be used is not particularly limited as long as the reaction proceeds but, for example, tetrahydrofuran and the like are desirable.

The amount of compound (16) to be used is about 1-10 mol, preferably 2-3 mol, relative to 1 mol of compound (15). Examples of the "base" include alkali metal hydrides and the like. The amount of the base to be used is about 1-10 mol, preferably 1-5 mol, relative to 1 mol of compound (15).

It is desirable to carry out the reaction generally under cooling or at room temperature condition, preferably 0° C.

The reaction time is generally 1-48 hr, preferably 3-16 hr.

In step 10, compound (18) is produced from compound (17), wherein a reaction can be performed in the presence of an organic base. This step can be performed by the method described in Indian J. Chem. Sect. B 1991, 30B, 932-935, or a method analogous thereto. It is advantageous to carry out the reaction using an inert solvent for the reaction. The solvent to be used is not particularly limited as long as the reaction proceeds but, for example, acetonitrile and the like are desirable.

Preferable examples of the organic base include triethylamine and the like. The amount of the base to be used is about 1-10 mol, preferably 1-5 mol, relative to 1 mol of compound (17).

It is desirable to carry out the reaction generally heating under reflux conditions, preferably 100° C.-150° C.

The reaction time is generally 1-10 hr, preferably 1-5 hr.

In step 11, compound (20) is produced by removing protecting groups $R^{b2}$ and $R^{b3}$ from compound (19). This reaction can be performed by a method known per se, for example, the method described in Wiley-Interscience, "Protective Groups in Organic Synthesis, $3^{rd}$ Ed." (Theodora W. Greene, Peter G. M. Wuts), 1999, and the like.

In step 12, compound (1b) is produced from compound (20) wherein a reaction with triphenylphosphine and diisopropyl azodicarboxylate and the like is performed. The amount of the triphenylphosphine and diisopropyl azodicarboxylate to be used is about 1-10 mol, preferably 2-5 mol, relative to 1 mol of compound (20). It is advantageous to carry out the reaction using an inert solvent for the reaction. The solvent to be used is not particularly limited as long as the reaction proceeds but, for example, solvents such as ethers, aromatic hydrocarbons and the like or a mixed solvent thereof and the like are desirable.

It is desirable to carry out the reaction generally under cooling or at room temperature condition, preferably 0° C.

The reaction time is generally 0.5-24 hr, preferably 2-10 hr.

In step 13, compound (23) is produced by placing compound (21) in co-presence with an arylhalide derivative in the presence of a base.

The amount of the arylhalide derivative to be used is about 1-10 mol, preferably 1-3 mol, relative to 1 mol of compound (21).

Examples of the base include basic salts, organic bases, metal alkoxides, metal amides and the like, potassium carbonate or sodium methoxide is preferable.

The amount of the base to be used is about 1-10 mol, preferably 1-3 mol, relative to 1 mol of compound (21). It is advantageous to carry out the reaction in the absence of a solvent or using an inert solvent for the reaction.

The solvent to be used is not particularly limited as long as the reaction proceeds but, for example, ethers and amides are desirable. It is desirable to carry out the reaction generally at room temperature or heating under reflux conditions, preferably at room temperature.

The reaction time is generally 1-24 hr, preferably 2-4 hr.

In step 14, compound (23) or compound (1c) is produced by placing compound (22) or compound (24) in co-presence with a "boronic acid derivative", or compound (28) is produced by the co-presence of compound (26) and compound (27).

As the "boronic acid derivative", 1-phenyl-5-(4,4,5,5-tetramethyl-1,3,2-dioxaborolan-2-yl)-1H-pyrazole and the like can be used. The amount of the "boronic acid derivative" to be used is about 1-10 mol, preferably 1-3 mol, relative to 1 mol of compound (22) or compound (24).

The amount of the compound (27) to be used is about 1-10 mol, preferably 1-3 mol, relative to 1 mol of compound (26).

It is desirable to carry out the reaction generally in the presence of a palladium catalyst and "base".

Examples of the "palladium catalyst" include tris(dibenzylideneacetone)dipalladium(0), tetrakistriphenylphosphinepalladium(0), palladium acetate(II), bis(di-tert-butyl(4-dimethylaminophenyl)phosphine)dichloropalladium(II) and the like. The "palladium catalyst" can be used in an amount of about 0.01-1 equivalent, preferably 0.05-0.2 equivalent, relative to the reaction substrate. The "palladium catalyst" can be used together with a phosphine ligand. When using a phosphine ligand, it is used in an amount of about 0.01-4 equivalents, preferably 0.05-1 equivalent, relative to the reaction substrate. As the "phosphine ligand", for example, triphenylphosphine, and 4,5-bis(diphenylphosphino)-9,9-dimethylxanthene are exemplified. As the "base", sodium tert-butoxide or potassium phosphate can be used and the amount is from about 1 to 10 mol, preferably from 1 to 3 mol, relative to 1 mol of the reaction substrate. It is advantageous to carry out the present reaction in the absence of a solvent or in the presence of an inert solvent for the reaction. The solvent to be used is not particularly limited as long as the reaction proceeds but, for example, ethers, nitriles and the like are desirable. It is desirable to carry out the reaction generally at room temperature or heating under reflux conditions, preferably heating under reflux conditions. The reaction time generally is from 0.5 to 48 hours, preferably from 1 to 24 hours.

This coupling reaction can be carried out by the methods described in "Cross-Coupling Reactions: A Practical Guide (Topics in Current Chemistry)" (Springer) "Experimental Organic Metallic Chemistry for Synthesizing Chemists"

(Kodansha) and "Organic Synthesis using Transition Metals" (Kagaku Dojin) or by a comparable method.

In step 15, compound (24) is produced from compound (23).

Compound (24) can be produced by reacting compound (23) with N-bromosuccinimide and the like.

The amount of the N-bromosuccinimide to be used is about 1-10 mol, preferably 1-3 mol, relative to 1 mol of compound (23).

It is advantageous to carry out the reaction using an inert solvent for the reaction. The solvent to be used is not particularly limited as long as the reaction proceeds but, for example, amides and the like are desirable.

It is desirable to carry out the reaction generally at 0° C.-100° C., preferably 0° C.-room temperature.

The reaction time is generally 1-24 hr, preferably 2-10 hr.

In addition, compound (24) can be produced by reacting compound (23) with both or any one of phosphorus oxychloride and phosphorus pentachloride.

The amount of the phosphorus oxychloride to be used is about 10-50 mol, preferably 15-30 mol, relative to 1 mol of compound (23).

The amount of the phosphorus pentachloride to be used is about 5-30 mol, preferably 10-20 mol, relative to 1 mol of compound (23).

It is advantageous to carry out the reaction in the absence of a solvent or using an inert solvent for the reaction, preferably in the absence of a solvent.

It is desirable to carry out the reaction generally performed at room temperature or heating under reflux conditions, preferably heating under reflux conditions.

The reaction time is generally 10-48 hr, preferably 16-24 hr.

In addition, compound (24) can be produced by reacting compound (23) with N-phenylbis(trifluoromethanesulfoneimide) and the like in the presence of organic bases.

As the organic bases, triethylamine and the like are preferable.

The amount of the N-phenylbis(trifluoromethanesulfoneimide) to be used is about 1-10 mol, preferably 1-3 mol, relative to 1 mol of compound (23).

The amount of the organic bases to be used is about 1-10 mol, preferably 2-5 mol, relative to 1 mol of compound (23).

It is advantageous to carry out the reaction in the absence of a solvent or using an inert solvent for the reaction. The solvent is not limited as long as the reaction proceeds but, for example, ethers are desirable.

It is desirable to carry out the reaction generally at 0° C.-100° C., preferably 0° C.-room temperature.

The reaction time is generally 1-48 hr, preferably 16-24 hr.

In step 16, compound (1c) is produced from compound (23).

Compound (1c) can be produced by reacting compound (23) with the "boronic acid derivative" in the presence of a copper reagent.

As the copper reagent, copper acetate and the like can be used. The amount of the copper reagent to be used is about 1-20 mol, preferably 5-10 mol, relative to 1 mol of compound (23).

As the "boronic acid derivative", 1-phenyl-5-(4,4,5,5-tetramethyl-1,3,2-dioxaborolan-2-yl)-1H-pyrazole and the like can be used. The amount of the "boronic acid derivative" to be used is about 1-20 mol, preferably 5-10 mol, relative to 1 mol of compound (23).

It is advantageous to carry out the reaction in the absence of a solvent or using an inert solvent for the reaction. The solvent is not limited as long as the reaction proceeds but, for example, aromatic organic bases and the like are desirable.

It is desirable to carry out the reaction generally at room temperature or heating under reflux conditions, preferably heating under reflux conditions.

The reaction time is generally 24-96 hr, preferably 48-72 hr.

In addition, compound (1c) can be produced by reacting compound (23) with an iodopyrazole derivative in the presence of inorganic bases and copper powder.

As the inorganic base, potassium carbonate and the like are preferable.

The amount of the copper powder to be used is about 0.5-5 equivalents, preferably 1-2 equivalents, relative to 1 mol of compound (23).

The amount of the inorganic bases to be used is about 2-10 mol, preferably 3-5 mol, relative to 1 mol of compound (23).

It is advantageous to carry out the reaction using an inert solvent for the reaction. The solvent to be used is not particularly limited as long as the reaction proceeds but, for example, aromatic organic bases and the like are desirable.

It is desirable to carry out the reaction generally at room temperature or heating under reflux conditions, preferably heating under reflux conditions.

The reaction time is generally 10-48 hr, preferably 24 hr.

In addition, compound (1c) can also be produced from compound (23) by the reaction of step 6 mentioned earlier.

In step 17, compound (26) is produced from compound (25), wherein a reaction with benzyl bromide and the like is performed in the presence of alkali metal hydride.

The alkali metal hydrides are used in an amount of about 1-10 mol, preferably 1-3 mol, relative to 1 mol of compound (25). In addition, the benzyl bromide is used in an amount of about 1-10 mol, preferably 1-3 mol, relative to 1 mol of compound (25).

To promote the reaction, additives such as tetrabutylammoniumiodide and the like may also be added. The amount of the tetrabutylammoniumiodide to be used is about 0.1-3 equivalents, preferably 0.1-1 equivalent, relative to 1% mol of compound (25).

It is advantageous to carry out the reaction in the presence of an inert solvent for the reaction. The solvent to be used is not particularly limited as long as the reaction proceeds but, for example, amides, ethers or a mixed solvent thereof are desirable.

It is desirable to carry out the reaction generally at room temperature or at a low temperature, preferably 0° C.-room temperature.

The reaction time is generally 0.5 hr-48 hr, preferably 1 hr-24 hr.

In step 18, compound (29) is produced from compound (28), wherein a hydrogenation reaction is performed in the presence of a catalyst such as palladium on carbon and the like.

This reaction can be performed by a method known per se, for example, the method described in Wiley-Interscience, "Protective Groups in Organic Synthesis, $3^{rd}$ Ed." (Theodora W. Greene, Peter G. M. Wuts), 1999, and the like.

In step 19, compound (1d) is produced from compound (29), wherein a reaction is performed in the co-presence of triphenylphosphine and diisopropyl azodicarboxylate and the like, in the presence of an alcohol derivative.

The amount of the alcohol derivative to be used is about 1-5 mol, preferably 2-5 mol, relative to 1 mol of compound (29).

The amount of the triphenylphosphine to be used is about 1-10 mol, preferably 2-10 mol, relative to 1 mol of compound (29).

The amount of the diisopropyl azodicarboxylate and the like to be used is about 1-10 mol, preferably 2-10 mol, relative to 1 mol of compound (29).

It is advantageous to carry out the reaction using an inert solvent for the reaction. The solvent to be used is not particularly limited as long as the reaction proceeds but, for example, toluene and the like are desirable.

It is desirable to carry out the reaction generally at room temperature or heating under reflux conditions, preferably at room temperature-100° C.

The reaction time is generally 0.5-10 hr, preferably 1-3 hr.

In addition, compound (1d) can also be produced by placing compound (29) in the co-presence of a compound having a halogen or leaving group in the presence of a base.

Examples of the base include inorganic bases.

The amount of the base to be used is about 1-10 mol, preferably 2-5 mol, relative to 1 mol of compound (29).

The amount of the compound having a halogen or leaving group to be used is about 1-10 mol, preferably 2-5 mol, relative to 1 mol of compound (29).

It is advantageous to carry out the reaction using an inert solvent for the reaction. The solvent to be used is not particularly limited as long as the reaction proceeds but, for example, ethers, amides and the like are preferable.

It is desirable to carry out the reaction generally at room temperature or under heating conditions, preferably at room temperature-100° C.

The reaction time is generally 1-48 hr, preferably 3-24 hr.

In addition, compound (29) can be used as a starting material when producing compound (1e).

In step 20, compound (1d') is produced from compound (30), wherein a reaction is performed in the co-presence of a transition metal catalyst under a hydrogen atmosphere.

It is advantageous to carry out the reaction using an inert solvent for the reaction. The solvent to be used is not particularly limited as long as the reaction proceeds but, for example, acetic acid and alcohols are desirable.

The hydrogen pressure is generally 1-10 atm, preferably 1-5 atm. Examples of the "transition metal catalyst" include palladium on carbon and rhodium on carbon. The amount of the transition metal catalyst to be used is about 0.01-1 equivalent, preferably 0.05-0.1 equivalent, relative to 1 mol of compound (30).

It is desirable to carry out the reaction generally at room temperature or under heating conditions, preferably 40-100° C.

The reaction time is generally 1-5 days, preferably 3-5 days.

It is also possible to produce compound (1d') by a method including synthesizing a pyridinium salt from compound (30), reducing the salt with borohydride sodium and the like and further subjecting same to deprotection.

The reaction to synthesize a pyridinium salt from compound (30) can be performed in the co-presence of compound (30) and benzylbromide or allylbromide and the like.

The amount of the benzyl bromide or allylbromide to be used is about 1-5 mol, preferably 2-5 mol, relative to 1 mol of compound (30).

It is advantageous to carry out the reaction using an inert solvent for the reaction. The solvent to be used is not particularly limited as long as the reaction proceeds but, for example, acetonitrile and the like are desirable.

It is desirable to carry out the reaction generally at room temperature or heating under reflux conditions, preferably heating under reflux conditions.

The reaction time is generally 5-24 hr, preferably 10-16 hr.

In the reaction to reduce the pyridinium salt with borohydride sodium and the like, the borohydride sodium is used in an amount of about 5-30 mol, preferably 5-10 mol, relative to 1 mol of the reaction substrate.

It is advantageous to carry out the reaction using an inert solvent for the reaction. The solvent to be used is not particularly limited as long as the reaction proceeds but, for example, alcohols are desirable.

It is desirable to carry out the reaction generally at room temperature or at a low temperature, preferably 0° C.-room temperature.

The reaction time is generally 5-24 hr, preferably 10-16 hr.

The reaction to produce compound (1d') by deprotection of the compound obtained by the above-mentioned reaction can be performed under a hydrogen atmosphere in the co-presence of a transition metal catalyst.

It is advantageous to carry out the reaction using an inert solvent for the reaction. The solvent to be used is not particularly limited as long as the reaction proceeds but, for example, acetic acid and alcohols are desirable.

The hydrogen pressure is generally 1-10 atm, preferably 1-5 atm. Examples of the "transition metal catalyst" include palladium hydroxide on carbon and the like. The amount of the transition metal catalyst to be used is about 0.01-1 equivalent, preferably 0.01-0.1 equivalent, relative to the reaction substrate.

It is desirable to carry out the reaction generally at room temperature or under heating conditions, preferably 40-100° C.

The reaction time is generally 1-24 hr, preferably 3-10 hr.

As a method for the reaction to produce compound (1d') by deprotection of the compound obtained by the above-mentioned reaction, a method including reacting 1,3-dimethylbarbituric acid in the presence of a palladium catalyst can also be used.

Examples of the palladium catalyst include tetrakis(triphenylphosphine)palladium(0) and the like.

The amount of the palladium catalyst to be used is about 0.01-1 equivalent, preferably 0.05-0.1 equivalent, relative to the reaction substrate.

The amount of the 1,3-dimethylbarbituric acid to be used is about 1-10, preferably 2-5 mol relative to the reaction substrate.

It is advantageous to carry out the reaction using an inert solvent for the reaction. The solvent to be used is not particularly limited as long as the reaction proceeds but, for example, dichloromethane and the like are desirable.

It is desirable to carry out the reaction generally at room temperature or heating under reflux conditions, preferably heating under reflux conditions.

The reaction time is generally 2-48 hr, preferably 16-24 hr.

In step 21, compound (1d") is produced from compound (1d').

Compound (1d") can be produced by reducing iminium ion developed from ketone or aldehyde and compound (1d') with a reducing agent.

The amount of ketone or aldehyde to be used is about 1-10 mol, preferably 2-5 mol, relative to 1 mol of compound (1d').

As the reducing agent to be used, sodium triacetoxyborohydride and the like are preferable, and used in an amount of about 1-10 mol, preferably 2-5 mol, relative to 1 mol of compound (1d').

It is advantageous to carry out the reaction using an inert solvent for the reaction. The solvent to be used is not particularly limited as long as the reaction proceeds but, for example, a mixed solvent of tetrahydrofuran and acetic acid and the like are desirable.

It is desirable to carry out the reaction generally at room temperature or heating under reflux conditions, preferably at room temperature-100° C.

The reaction time is generally 1-120 hr, preferably 10-24 hr.

In addition, compound (1d") can also be produced by reacting compound (1d') with halogenated aryl in the presence of a palladium catalyst, a phosphine ligand and a base.

As the halogenated aryls, iodobenzene and the like are preferable. The halogenated aryls are used in an amount of about 1-10 mol, preferably 2-5 mol, relative to 1 mol of compound (1d').

As the palladium catalyst, tris(dibenzylideneacetone)dipalladium(0) and the like are preferable, as the phosphine ligand, 4,5-bis(diphenylphosphino)-9,9-dimethylxanthene and the like are preferable, and as the base, sodium tert-butoxide and the like are preferable.

The palladium catalyst is used in an amount of about 0.1-1 equivalent, preferably 0.1-0.5 equivalent, relative to compound (1d'). The phosphine ligand is used in an amount of about 0.1-1 equivalent, preferably 0.1-0.5 equivalent, relative to compound (1d').

The base is used in an amount of about 1-10 mol, preferably 2-5 mol, relative to 1 mol of compound (1d').

It is advantageous to carry out the reaction in the absence of a solvent or using an inert solvent for the reaction. The solvent is not limited as long as the reaction proceeds but, for example, 1,4-dioxane and the like are preferable.

It is desirable to carry out the reaction generally at room temperature or heating under reflux conditions, preferably at room temperature-150° C.

The reaction time is generally 1-24 hr, preferably 1-10 hr.

In addition, compound (1d") can also be produced by reacting compound (1d') with acid halide in the presence of a base.

As the acid halide, acetyl chloride and the like are preferable. The acid halide is used in an amount of about 1-10 mol, preferably 2-5 mol, relative to 1 mol of compound (1d').

The solvent to be used is not particularly limited as long as the reaction proceeds but, for example, ethers and amides are desirable. As the base, for example, triethylamine and the like are preferable.

The base is used in an amount of about 1-10 mol, preferably 1-3 mol, relative to 1 mol of compound (1d'). It is desirable to carry out the reaction generally at room temperature or heating under reflux conditions, preferably at room temperature.

The reaction time is generally 1-24 hr, preferably 1-16 hr.

In addition, compound (1d") can also be produced by reacting compound (1d') with an isocyanate derivative.

As the isocyanate derivative, phenylisocyanate and the like are preferable. The isocyanate derivative is used in an amount of about 1-10 mol, preferably 2-5 mol, relative to 1 mol of compound (1d').

The solvent to be used is not particularly limited as long as the reaction proceeds but, for example, ethers and amides are desirable.

It is desirable to carry out the reaction generally at room temperature or heating under reflux conditions, preferably at room temperature.

The reaction time is generally 1-24 hr, preferably 1-5 hr.

In step 22, compound (1e) is produced from compound (31).

It can be produced by reacting with alkyl halide and the like in the presence of alkali metal hydride.

The alkali metal hydrides are used in an amount of about 1-10 mol, preferably 1-3 mol, relative to 1 mol of compound (31). In addition, the alkyl halide is used in an amount of about 1-10 mol, preferably 1-3 mol, relative to 1 mol of compound (31).

To promote the reaction, additives such as tetrabutylammoniumiodide and the like may also be added. The amount of the tetrabutylammoniumiodide to be used is about 0.1-3 equivalents, preferably 0.1-1 equivalent, relative to 1 mol of compound (31).

It is advantageous to carry out the reaction without solvent or in the presence of an inert solvent for the reaction. The solvent to be used is not particularly limited as long as the reaction proceeds but, for example, amides, ethers and a mixed solvent thereof are desirable.

It is desirable to carry out the reaction generally at room temperature or at a low temperature, preferably 0° C.-room temperature.

The reaction time is generally 0.5 hr-48 hr, preferably 1 hr-24 hr.

In addition, compound (1e) may be produced by reacting compound (31) with a sulfonylchloride derivative.

As the sulfonylchloride derivative, benzenesulfonylchloride and the like are preferable. The sulfonylchloride derivative is used in an amount of about 1-10 mol, preferably 1-3 mol, relative to 1 mol of compound (31).

It is advantageous to carry out the present reaction without solvent or in the presence of an inert solvent for the reaction. The solvent to be used is not particularly limited as long as the reaction proceeds but, for example, aromatic organic bases are desirable.

It is desirable to carry out the reaction generally at room temperature or under heated conditions, preferably at room temperature.

The reaction time is generally 3 hr-48 hr, preferably 5 hr-24 hr.

In step 23, compound (33) is produced from compound (32).

It can be produced using amines and a condensing agent in the presence of an organic base, 1-hydroxy-1H-benzotriazole and the like.

As the amines, methyl 2-methylalaninate can be used.

Examples of the condensing agent include 1-ethyl-3-(3-dimethylaminopropyl)-carbodiimide hydrochloride.

It is advantageous to carry out the reaction in the absence of a solvent or using an inert solvent for the reaction. The solvent is not limited as long as the reaction proceeds but, for example, nitriles, ethers and amides are desirable.

The amount of the amines to be used is about 1-5 mol, preferably 1-3 mol, relative to 1 mol of compound (32).

The amount of the condensing agent to be used is about 1-5 mol, preferably 1-3 mol, relative to 1 mol of compound (32).

The amount of the 1-hydroxy-1H-benzotriazole to be used is about 1-5 mol, preferably 1-3 mol, relative to 1 mol of compound (32).

The amount of the organic bases to be used is about 1-10 mol, preferably 2-3 mol, relative to 1 mol of compound (32).

It is desirable to carry out the reaction generally at room temperature or under heated conditions, preferably at room temperature.

The reaction time is generally 1-48 hr, preferably 5-10 hr.

In step 24, compound (34) is produced from compound (33), wherein production of carboxylic acid by ester hydrolysis and condensation of the obtained carboxylic acid and amine are continuously performed.

The step of producing carboxylic acid by ester hydrolysis can be performed by a reaction under acidic or basic conditions. It is advantageous to carry out this reaction without using a solvent or using an inert solvent for the reaction. The solvent to be used is not particularly limited as long as the reaction proceeds but, for example, it is desirable to use alcohols, a solvent mixed with water and ethers.

As the acid, for example, inorganic acids can be used.

Examples of the base include inorganic bases.

The amount of the acid or the base to be used is about 1-10 mol, preferably 1-5 mol, relative to 1 mol of the compound (33).

It is desirable to carry out the reaction generally at room temperature or under heated conditions, preferably at room temperature.

The reaction time generally is 1-48 hours, preferably 3-10 hours.

The subsequent step of condensation with amine can be performed using a condensing agent by a reaction in the presence of an organic base and 1-hydroxy-1H-benzotriazole.

As the amines, aniline can be used.

Examples of the condensing agent include 1-ethyl-3-(3-dimethylaminopropyl)-carbodiimide hydrochloride.

It is advantageous to carry out the reaction in the absence of a solvent or using an inert solvent for the reaction. The solvent is not limited as long as the reaction proceeds but, for example, nitriles, ethers and amides are preferable.

The amount of the amines to be used is about 1-5 mol, preferably 1-3 mol, relative to 1 mol of compound (33).

The amount of the condensing agent to be used is about 1-5 mol, preferably 1-3 mol, relative to 1 mol of compound (33).

The amount of the 1-hydroxy-1H-benzotriazole to be used is about 1-5 mol, preferably 1-3 mol, relative to 1 mol of compound (33).

The amount of the organic bases to be used is about 1-10 mol, preferably 2-3 mol, relative to 1 mol of compound (33).

It is desirable to carry out the reaction generally at room temperature or under heated conditions, preferably at room temperature.

The reaction time is generally 5-48 hr, preferably 10-24 hr.

In step 25, compound (1f) is produced from compound (34), wherein it can be performed in the presence of sodium acetate and the like.

The amount of the sodium acetate to be used is about 1-5 mol, preferably 1-3 mol, relative to 1 mol of compound (34).

This reaction is preferably carried out without solvent or using an inert solvent for the reaction. While such solvent is not particularly limited as long as the reaction proceeds, for example, acetic acid and the like are preferable. Further, it is generally desirable to carry out the reaction heating under reflux conditions, or it is possible to be heated under microwave conditions. The reaction temperature when heating under microwave conditions generally is from 50° C. to 150° C., preferably at a temperature ranging from 100° C. to 130° C. The reaction time generally is from 30 to 180 min., preferably from 60 to 120 min.

The compound of the present invention obtained by the aforementioned methods can be isolated or purified by the ordinary separation means such as recrystallization, distillation, chromatography and the like. If the compound (1$^x$) or compound (1) is obtained in a free form, they can be converted to their salts by the known methods or by a comparable method (e.g., neutralization, etc.), or in reverse, if they are obtained in the salt form, they can be converted to a free form or other salts by the known methods or by a comparable method.

When the compound of the present invention is present as a configuration isomer, a diastereomer, a conformer and the like, they can be respectively isolated when desired by the above-mentioned separation and purification means. If the compound of the present invention is a racemate, it can be separated into a d-form and l-form by the ordinary optical resolution means.

The starting compound used for the production of the compound of the present invention may be a salt as long as the reaction is not impaired. Examples of such salt include salts similar to those of compound (1$^x$) or compound (1).

In any of the above mentioned production methods or processes, if desired, a compound (1$^x$) or compound (1) can be synthesized by further applying one or combination of known reactions such as protection/deprotection reactions, acylation reactions, alkylation reactions, hydrogenation reactions, oxidation reactions, reduction reactions, carbon chain extension reactions, substituent exchanging reactions, and so on.

The compound of the present invention has an excellent PDE10A inhibitory activity, and for example, is useful as a medicament for preventing or treating the following diseases and symptoms.

psychotic disorder (e.g., brief psychotic disorder, induced delusional disorder);

psychotic diseases induced by alcohol, amphetamine, cannabinoid, cocaine, hallucinogens, obesity, opioids, phencyclidine and the like;

delusional disorder;

anxiety disorder;

movement disorder;

mood disorder;

major depression;

depression overlapping with psychotic disorders including delusional disorder or schizophrenia;

major depressive episode of mild, moderate or severe type;

manic or mixed episode;

hypomanic episode;

depressive episode with atypical features;

depressive episode with melancholic features;

depressive episode with catatonic features;

mood episode with postpartum onset;

post-stroke depression;

dysthymic disorder;

minor depression;

autism;

drug addiction;

neurodegenerative disease;

neurodegeneration associated with brain trauma;

neurodegeneration associated with cerebral stroke;

neurodegeneration associated with cerebral infarction;

hypoglycemia-induced neurodegeneration;

neurodegeneration associated with epilepsy seizure;

neurodegeneration associated with neurotoxin;

multiple-system atrophy;

Alzheimer's disease;

dementia;

multi-infarct dementia;

alcoholic dementia or other drug-related dementia;

dementia associated with intracranial tumor or cerebrum trauma;

dementia associated with Huntington's disease or Parkinson's disease;

AIDS-related dementia syndrome;

fronto temperal dementia;

delirium;

amnestic disorder;

post-traumatic stress disorder;

mental retardation (hypophrenia);

learning disorder (e.g., dyslexia, dyscalculia, agraphia);
attention-deficit hyperactivity disorder;
age-related cognitive decline;
premenstrual dysphoric disorder;
bipolar disorder including bipolar I disorder or bipolar II disorder;
cyclothymic disorder;
Parkinson's disease;
Huntington's disease;
delusion;
schizophrenia (e.g., paranoid schizophrenia, disorganized schizophrenia, catatonic schizophrenia, undifferentiated schizophrenia, residual schizophrenia);
schizoaffective disorder;
schizoaffective disorder of the delusional type or the depressive type;
personality disorder of the paranoid type;
personality disorder of the schizoid type;
obesity;
metabolic syndrome;
non-insulin dependent diabetes;
glucose intolerance.

In particular, the compound of the present invention is useful for preventing or treating schizophrenia.

Since the compound of the present invention demonstrates excellent metabolic stability, superior therapeutic effects on the aforementioned diseases are expected even at a low dosage.

Since the compound of the present invention has low toxicity (e.g., more superior as medicament in terms of acute toxicity, chronic toxicity, genetic toxicity, reproductive toxicity, cardiotoxicity, drug interaction, carcinogenicity and the like), it can be safely administered as it is as a medicament, or as a pharmaceutical composition obtained by mixing with a pharmaceutically acceptable carrier etc., orally or parenterally to a mammal (e.g., human, monkey, bovine, horse, swine, mouse, rat, hamster, rabbit, cat, dog, sheep, goat etc.).

The compound of the present invention can be used singly as a medicament according to a method known per se (e.g., the method described in the Japanese Pharmacopoeia etc.) as a production method of a pharmaceutical preparation. In addition, the compound of the present invention can be used as a pharmaceutical composition by mixing with a pharmacologically acceptable carrier.

A medicament containing the compound of the present invention can be safely administered as, for example, tablets (inclusive of sugar-coated tablet, film-coated tablet, sublingual tablet, orally disintegrable tablet, buccal, etc.), pills, powders, granules, capsules (inclusive of soft capsule, and microcapsule), troches, syrups, liquids, emulsions, suspensions, controlled-release preparations (e.g., quick-release preparation, sustained-release preparation, sustained-release microcapsule), aerosols, films (e.g., orally disintegrable film, oral mucosal adhesive film), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, and directly to lesion).

As a pharmaceutical acceptable carrier, common organic or inorganic carrier substances are used as formulation raw materials. Carriers are added as vehicles, lubricants, binders and disintegrants in the solid formulations; and as solvents, solubilizing agents, suspending agents, isotonization agents, buffers, soothing agents etc. in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light anhydrous silicic acid, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropyl cellulose, hydroxypropyl methyl cellulose and polyvinyl pyrrolidone.

Favorable examples of the disintegrants are as follows: lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose, etc.; polysorbates, and polyoxyethylene hydrogenated castor oil.

Favorable examples of the isotonization agents include sodium chloride, glycerin, D-mannitol, D-sorbitol and glucose.

Favorable examples of the buffers include buffer solutions of phosphates, acetates, carbonates and citrates, etc.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2, etc.); water insoluble lake dyes (e.g., aluminum salts of the aforementioned water soluble edible tar dyes), natural dyes (e.g., β-carotene, chlorophyll, ferric oxide red).

Favorable examples of the sweeteners include sodium saccharin, dipotassium glycyrrhizinate, aspartame and stevia.

The pharmaceutical compositions of the present invention can be manufactured by the common methods in the field of formulation technology, for example, methods listed in the Japanese pharmacopoeia, etc. Specific production methods for formulations are described in detail below.

The content of the compound of the present invention in the pharmaceutical compositions of the present invention varies based on the dosage forms, dosages of the compound of the present invention, etc. For example, the content approximately ranges from about 0.01 to 100 wt % and preferably from 0.1 to 95 wt % relative to the entire amount of the composition.

The dosage of the compound of the present invention depends upon administration subjects, administration routes, target diseases, symptoms, etc. For example, in the case of oral administration in patients with schizophrenia (adults, bodyweight of about 60 kg), generally a single dose ranges from about 0.1 to about 20 mg/kg bodyweight, preferably from about 0.2 to about 10 mg/kg bodyweight, further preferably from about 0.5 to about 10 mg/kg bodyweight, and this dosage is preferably administered once daily or several times daily (e.g., 3 times).

The compound of the present invention may be used in combination with other active ingredients. Examples of the drug that can be used in combination or concomitantly with the compound of the present invention (hereinafter sometimes to be abbreviated as concomitant drug) include the following.

A therapeutic drug for mental diseases, particularly schizophrenia, or bipolar disorder, obsessive disorder, major depression, Parkinson's disease, Huntington's disease, Alzheimer's disease, cognitive dysfunction and memory disorders [atypical antipsychotic agents (e.g., clozapine, olanzapine, risperidone, aripiprazole, blonanserin, iloperidone, asenapine, ziprasidone, quetiapine, zotepine etc.), typical antipsychotic agents (e.g., haloperidol, chlorpromazine etc.), selective serotonin reuptake inhibitor (e.g., paroxetine, sertraline, fluvoxamine, fluoxetine etc.), selective serotonin•noradrenaline reuptake inhibitor (e.g., milnacipran, venlafaxine etc.), selective noradrenaline•dopamine reuptake inhibitor (e.g., bupropion etc.), tetracyclic antidepressant (e.g., amoxapine, clomipramine etc.), tricyclic antidepressant (e.g., imipramine, amitriptyline etc.), other antidepressant (e.g., NS-2359, Lu AA21004, DOV21947 etc.), $\alpha_7$ nicotine receptor agonist, $\alpha_7$ nicotine receptor activity regulator, $\alpha_7$ nicotine receptor partial regulator (e.g., SSR-180711, PNU-120596 etc.), PDE1 inhibitor, PDE2 inhibitor, PDE4 inhibitor, PDE5 inhibitor, PDE7 inhibitor, PDE9 inhibitor, other PDE inhibitor, calcium channel inhibitor, NK2 antagonist, NK3 antagonist, muscarine type M1 acetylcholine receptor activity regulator, muscarine type M2 acetylcholine receptor activity regulator, adenosine receptor regulator, muscarine type M4 acetylcholine receptor activity regulator, muscarine type M5 acetylcholine receptor activity regulator, adenosine receptor regulator, glycine transporter type 1 inhibitor (e.g., ALX5407, SSR504734 etc.), glutamate enhancer (e.g., ampakine), NMDA-type glutamate receptor regulator, metabolic glutamate receptor regulator (e.g., CDPPB, MPEP etc.), antianxiety drug (benzodiazepine (e.g., diazepam, etizolam etc.), serotonin 5-$HT_{1A}$ agonist (e.g., tandospirone etc.)), hypnotic pills (benzodiazepine (e.g., estazolam, triazolam etc.), non-benzodiazepine (e.g., zolpidem etc.), melatonin receptor agonist (e.g., ramelteon etc.)), β amyloid vaccine, β amyloid degrading enzyme etc., brain function activator (e.g., aniracetam, nicergoline etc.), cannabinoid regulator, cholinesterase inhibitor (e.g., donepezil, rivastigmine, galanthamine), therapeutic drug for Parkinson's disease (e.g., dopamine receptor agonist (L-DOPA, bromocriptine, pergolide, talipexole, pramipexole, cabergoline, amantadine etc.), monoamine oxidase inhibitor (deprenyl, selegiline, remacemide, riluzole etc.), anticholinergic agent (e.g., trihexyphenidyl, biperiden etc.), COMT inhibitor (e.g., entacapone etc.), a therapeutic drug for amyotrophic lateral sclerosis (e.g., riluzole etc., neurotrophic factor etc.), apoptosis inhibitor (e.g., CPI-1189, IDN-6556, CEP-1347 etc.), neuronal differentiation•regeneration promoter (e.g., leteprinim, xaliproden (SR-57746-A), SB-216763 etc.)], and a therapeutic drug for diseases easily developed with schizophrenia[therapeutic drug for diabetes (PPAR acting drug (e.g., agonist, inhibitor, pioglitazone, rosiglitazone, troglitazone), insulin secretagogue (e.g., sulfonylurea drugs, non-sulfonylurea drugs), a glucosidase inhibitor (e.g., acarbose), insulin sensitizer (e.g., PPAR-γ acting drug, PTP-1B inhibitor, DPP-4 inhibitor, 11β-HSD inhibitor), liver gluconeogenesis inhibitor (e.g., glucagon antagonist, metformin), insulin, insulin derivative), antiobesity drug (β-3 agonist, CB1 agonist, neuropeptide Y5 inhibitor, anorexigenic agent (e.g., sibutramine), lipase inhibitor (e.g., orlistat)), a therapeutic drug for hyperlipidemia such as a cholesterol lowering agent and the like (statin (e.g., pravastatin sodium, atrovastatin, simvastatin, rosuvastatin etc.), fibrate (e.g., clofibrate etc.), squalene synthase inhibitor), antihypertensive agent, non-steroidal anti-inflammatory agent (e.g., meloxicam, teoxicam, indomethacin, ibuprofen, celecoxib, rofecoxib, aspirin, indomethacin etc.), disease-modified anti-rheumatic drug (DMARDs), anticytokine agent (TNF inhibitor, MAP kinase inhibitor and the like), steroid drug (e.g., dexamethasone, hexestrol, cortisone acetate etc.), sex hormone or a derivative thereof (e.g., progesterone, estradiol, estradiol benzoate etc.), parathyroid hormone (PTH), calcium receptor antagonist etc.]

The dosage form of concomitant drugs with the compound of the present invention is not particularly limited and is acceptable as long as the compound of the present invention is combined with concomitant drugs at the time of administration. Examples of such dosage forms are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order). These dosage forms are summarized below and abbreviated as a combination drug of the present invention.

When administering the combination drug of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, dosage forms and methods of administration. For example, when a concomitant drug is administered first, the compound of the present invention can be administered within 1 min. to 3 days, preferably within 10 min. to 1 day and more preferably within 15 min. to 1 hour after the concomitant drug is administered. However, if the compound of the present invention is administered first, a concomitant drug can be administered within 1 min. to 1 day, preferably within 10 min. to 6 hours and more preferably within 15 min. to 1 hour after the compound of the present invention is administered.

If there are no problems with side effects of the concomitant drugs, any dosages can be set. A daily dosage as a concomitant drug depends upon administration subjects, administration routes, target diseases, symptoms, etc. For example, in the case of oral administration in patients with schizophrenia (adults, bodyweight of about 60 kg), a normal once dosage ranges from about 0.1 to about 20 mg/kg bodyweight, preferably from about 0.2 to about 10 mg/kg bodyweight and more preferably from about 0.5 to about 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or (and) the aforementioned concomitant drug can be combined with a pharmaceutically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or parenterally.

The pharmaceutically acceptable carriers that may be used for production the combination drug of the present invention can be the same as those used in the pharmaceutical composition of the present invention as mentioned above.

A combination ratio between the compound of the present invention and a concomitant drug in the combination drug of the present invention can be selected appropriately based on the administration subjects, administration routes and diseases, etc.

The aforementioned concomitant drugs can be used in combination at an appropriate proportion if two or more drugs are combined. A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug may be used in an amount ranging from 0.01 to 100 parts by weight relative to 1 part by weight of the compound of the present invention.

For example, the content of the compound of the present invention in the combination drug of the present invention varies with the form of formulations. Generally, it is present in a range from about 0.01 to 99.9 wt %, preferably from about 0.1 to about 50 wt % and more preferably from about 0.5 to about 20 wt % relative to the entire formula.

The content of a concomitant drug in the combination drug of the present invention varies with the drug form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the drug form of formulations. Generally it is present in a range from about 1 to 99.99 wt % and preferably from about 10 to about 90 wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLES

The present invention is explained in detail in the following by referring to Examples, Experimental Examples and Preparation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In the following Examples, the following abbreviations are used.
THF: tetrahydrofuran
DMF: N,N-dimethylformamide
DMSO: dimethyl sulfoxide
ESI: electrospray ionization method
API: atmospheric chemical ionization method
[M+H]$^+$: molecular ion peak
TFA: trifluoroacetic acid
M: molar concentration
N: normal concentration
WSC: N-(3-dimethylaminopropyl)-N'-ethylcarbodiimide hydrochloride
HOBt: 1-hydroxybenzotriazole monohydrate
HPLC: high performance liquid chromatography
DIAD: isopropyl azodicarboxylate
Pd$_2$(dba)$_3$: tris(dibenzylideneacetone)dipalladium(0)
Xantphos: 4,5-bis(diphenylphosphino)-9,9-dimethylxanthene
X-phos: 2-dicyclohexylphosphino-2',4',6'-triisopropylbiphenyl
NaH: sodium hydride
PdCl$_2$(PPh$_3$)$_2$: bis(triphenylphosphine)palladium(II)dichloride
DMAP: N,N-dimethyl-4-aminopyridine $^1$H NMR (proton nuclear magnetic resonance spectrum) was measured by Fourier-transform type NMR. For the analysis, ACD/SpecManager (trade name) and the like were used. Very mild peaks showing protons of hydroxyl group, amino group and the like are not described.

MS (mass spectrum) was measured by LC/MS (liquid chromatography mass spectrometer).

As the ionization method, ESI (ElectroSpray Ionization) method, or APCI (Atmospheric Pressure Chemical Ionization) method was used. The data shows Found. Generally, molecular ion peak are observed. When a compound having a tert-butoxycarbonyl group (-Boc) is used, a peak free of a tert-butoxycarbonyl group or tert-butyl group may be observed as a fragment ion. In addition, when a compound having a hydroxyl group (—OH) is used, a peak free of H$_2$O may be observed as a fragment ion. In the case of a salt, generally, a molecular ion peak or a fragment ion peak of a free form is observed.

Example 1

3-(1-phenyl-1H-pyrazol-5-yl)-1-[3-(trifluoromethyl)phenyl]furo[3,2-c]pyridazin-4(1H)-one A) 3-bromofuran-2-carboxylic acid To a solution of 3-bromofuran-2-carbaldehyde (25.0 g) and 2-methyl-2-butene (45.4 mL) in tert-butanol (250 mL) was added dropwise a solution of 80% sodium chlorite (40.5 g) and sodium dihydrogen phosphate (51.5 g) in water (350 mL) at room temperature, and the mixture was stirred overnight. To the reaction mixture was added 1M hydrochloric acid (300 ml), and the mixture was extracted with ethyl acetate. The extract was washed with saturated brine, dried over anhydrous magnesium sulfate, and concentrated under reduced pressure. The residue was washed with hexane/ethyl acetate (5/1) and recrystallized from hexane/ethyl acetate to give the title compound (20.3 g). $^1$H NMR (300 MHz, CDCl$_3$) δ 6.66 (1H, d, J=1.9 Hz), 7.58 (1H, d, J=1.9 Hz).

B) ethyl 3-bromofuran-2-carboxylate

A suspension of 3-bromofuran-2-carboxylic acid (23.5 g), iodoethane (11.8 mL) and potassium carbonate (25.6 g) in DMF (200 mL) was stirred at 60° C. overnight. The reaction mixture was poured into water, and the mixture was extracted with diethylether. The extract was washed with water and saturated brine, dried over anhydrous magnesium sulfate, and concentrated under reduced pressure. The residue was dissolved in hexane, passed through a silica gel (NH) layer, and the eluate was concentrated under reduced pressure to give the title compound (23.0 g).
$^1$H NMR (300 MHz, CDCl$_3$) δ 1.41 (3H, t, J=7.2 Hz), 4.40 (2H, q, J=7.2 Hz), 6.60 (1H, d, J=1.9 Hz), 7.50 (1H, d, J=1.9 Hz).

C) 1-(3-bromofuran-2-yl)butane-1,3-dione

To a solution of ethyl 3-bromofuran-2-carboxylate (16.2 g) and acetone (5.14 mL) in toluene (250 mL) was added potassium tert-butoxide (15.7 g) at 0° C. portionwise. The reaction mixture was stirred at room temperature for 2 hr, and acetic acid (8.01 mL) and water (250 mL) were added. The organic layer was separated, washed with saturated brine, dried over anhydrous magnesium sulfate, and concentrated under reduced pressure. The residue was purified by silica gel column chromatography (hexane/ethyl acetate) and recrystallized from hexane/ethyl acetate to give the title compound (10.9 g, enol/diketone=88/12).
$^1$H NMR (300 MHz, CDCl$_3$) enol form δ 2.15 (3H, s), 6.23 (1H, s), 6.62 (1H, d, J=1.9 Hz), 7.50 (1H, d, J=1.9 Hz), 15.58 (1H, brs); diketone form δ 2.31 (3H, s), 4.03 (2H, s), 6.66 (1H, d, J=1.9 Hz), 7.51 (1H, d, J=1.9 Hz).

D) 1-(3-bromofuran-2-yl)-2-{[3-(trifluoromethyl)phenyl]hydrazono}butane-1,3-dione To a mixture of 3-(trifluoromethyl)aniline (0.500 mL) and 6M hydrochloric acid (4 mL) was added dropwise a solution of sodium nitrite (0.345 g) in water (1 mL) at 0° C., and the mixture was stirred for 15 min. The obtained aqueous solution was added to a suspension, which was cooled to 0° C., of 1-(3-bromofuran-2-yl)butane-1,3-dione (0.924 g) and sodium acetate (1.97 g) in methanol (10 mL). The reaction mixture was poured into water, and the mixture was extracted with ethyl acetate. The extract was washed with saturated aqueous sodium hydrogen carbonate solution and saturated brine, dried over anhydrous magnesium sulfate, and concentrated under reduced pressure to give the title compound (1.59 g).
$^1$H NMR (300 MHz, CDCl$_3$) δ 2.586 (3H×0.22, s), 2.593 (3H×0.78, s), 6.66 (1H×0.78, d, J=1.9 Hz), 6.69 (1H×0.22, d, J=1.9 Hz), 7.37-7.65 (5H, m), 12.42 (1H×0.78, s), 14.62 (1H×0.22, s).

E) 3-acetyl-1-[3-(trifluoromethyl)phenyl]furo[3,2-c]pyridazin-4(1H)-one

A suspension of 1-(3-bromofuran-2-yl)-2-{[3-(trifluoromethyl)phenyl]hydrazono}butane-1,3-dione (1.59 g) and potassium carbonate (0.817 g) in DMF (10 mL) was stirred at 90° C. for 4 hr. The reaction mixture was poured into water, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate) and recrystallized from hexane/ethyl acetate to give the title compound (683 mg).
$^1$H NMR (300 MHz, CDCl$_3$) δ 2.73 (3H, s), 6.73 (1H, d, J=2.3 Hz), 7.73-7.88 (4H, m), 7.91 (1H, s).

F) 3-(1-phenyl-1H-pyrazol-5-yl)-1-[3-(trifluoromethyl)phenyl]furo[3,2-c]pyridazin-4(1H)-one A solution of 3-acetyl-1-[3-(trifluoromethyl)phenyl]furo[3,2-c]pyridazin-4(1H)-one (757 mg) in N,N-dimethylformamide dimethyl acetal (7.5 mL) was heated under reflux for 1.5 hr. After cooling to room temperature, the reaction mixture was concentrated under reduced pressure.
A solution of the obtained residue and phenylhydrazine (0.462 mL) in acetic acid (7.5 mL) was heated under reflux for 1.5 hr. The reaction mixture was concentrated under reduced pressure, and the residue was dissolved in ethyl acetate. The obtained solution was washed with 1M hydrochloric acid, 1M aqueous sodium hydroxide solution and saturated brine, dried over anhydrous magnesium sulfate, and concentrated under reduced pressure. The residue was fractionated by HPLC (C18, mobile phase: water/acetonitrile (containing 0.1% TFA)), and the obtained fraction was concentrated under reduced pressure. The residue was recrystallized from hexane/ethyl acetate to give the title compound (219 mg).
$^1$H NMR (300 MHz, CDCl$_3$) δ 6.71 (1H, d, J=2.3 Hz), 7.13 (1H, dd, J=8.3, 1.9 Hz), 7.21 (1H, s), 7.35-7.45 (6H, m), 7.51 (1H, t, J=7.9 Hz), 7.64 (1H, d, J=7.9 Hz), 7.82 (1H, d, J=1.9 Hz), 7.86 (1H, d, J=2.3 Hz).

Example 2

3-(1-phenyl-1H-pyrazol-5-yl)-1-[3-(trifluoromethyl)phenyl]-6,7-dihydrofuro[3,2-c]pyridazin-4(1H)-one A) 3-(1-hydroxyethyl)-1-[3-(trifluoromethyl)phenyl]-6,7-dihydrofuro[3,2-c]pyridazin-4(1H)-one A suspension of 3-acetyl-1-[3-(trifluoromethyl)phenyl]furo[3,2-c]pyridazin-4(1H)-one (806 mg) and 10% palladium on carbon (containing water (50%), 400% mg) in methanol (25 mL) was stirred at room temperature for 24 hr under a hydrogen atmosphere. Palladium on carbon was removed by filtration, and the filtrate was concentrated under reduced pressure. The residue was purified by silica gel column chromatography (ethyl acetate) and crystallized from hexane/ethyl acetate to give the title compound (686 mg).

$^1$H NMR (300 MHz, CDCl$_3$) δ 1.58 (3H, d, J=6.8 Hz), 3.42 (2H, t, J=9.0 Hz), 4.56 (1H, d, J=6.8 Hz), 4.70 (2H, t, J=9.0 Hz), 5.06-5.15 (1H, m), 7.65-7.80 (4H, m).

B) 3-acetyl-1-[3-(trifluoromethyl)phenyl]-6,7-dihydrofuro[3,2-c]pyridazin-4(1H)-one To a solution of 3-(1-hydroxyethyl)-1-[3-(trifluoromethyl) phenyl]-6,7-dihydrofuro[3,2-c]pyridazin-4(1H)-one (0.858 g) in acetonitrile (20 mL) was added Dess-Martin Periodinane (1.23 g) portionwise, and the mixture was stirred at room temperature for 1 hr. The reaction mixture was poured into 1M aqueous sodium hydroxide solution, and the mixture was extracted with ethyl acetate. The extract was washed with saturated brine, dried over anhydrous magnesium sulfate, and concentrated under reduced pressure. The residue was purified by silica gel column chromatography (ethyl acetate/ methanol) and recrystallized from ethyl acetate to give the title compound (0.739 g).

$^1$H NMR (300 MHz, CDCl$_3$) δ 2.67 (3H, s), 3.43 (2H, t, J=9.2 Hz), 4.74 (2H, t, J=9.2 Hz), 7.69-7.82 (4H, m).

C) 3-(1-phenyl-1H-pyrazol-5-yl)-1-[3-(trifluoromethyl)phenyl]-6,7-dihydrofuro[3,2-c]pyridazin-4(1H)-one The title compound was obtained in the same manner as in step F of Example 1.

$^1$H NMR (300 MHz, CDCl$_3$) δ 3.42 (2H, t, J=9.0 Hz), 4.72 (2H, t, J=9.0 Hz), 7.00 (1H, dd, J=7.9, 1.9 Hz), 7.10 (1H, s), 7.30 (1H, d, J=1.9 Hz), 7.34-7.49 (6H, m), 7.63 (1H, t, J=7.9 Hz), 7.88 (1H, d, J=7.9 Hz).

Example 3

1-[2-fluoro-4-(1H-pyrazol-1-yl)phenyl]-3-(1-phenyl-1H-pyrazol-5-yl)furo[3,2-c]pyridazin-4(1H)-one

A) 1-(3-bromofuran-2-yl)-2-{[2-fluoro-4-(1H-pyrazol-1-yl)phenyl]hydrazono}butane-1,3-dione To a mixture of 2-fluoro-4-(1H-pyrazol-1-yl)aniline (2.3 g) and 6M hydrochloric acid (13 mL) was added dropwise a solution of sodium nitrite (1.0 g) in water (3 mL) at 0° C., and the mixture was stirred for 15 min. The obtained aqueous solution was added to a suspension, which was cooled to 0° C., of 1-(3-bromofuran-2-yl)butane-1,3-dione (3 g) and sodium acetate (6.4 g) in methanol (30 mL). The reaction mixture was poured into water, and the mixture was extracted with ethyl acetate. The extract was washed with saturated aqueous sodium hydrogen carbonate solution and saturated brine, dried over anhydrous magnesium sulfate, and concentrated under reduced pressure to give the title compound (5.3 g).

$^1$H NMR (300 MHz, DMSO-d$_6$) δ 6.34-6.77 (1H, m), 7.01 (1H, d, J=1.9 Hz), 7.52-8.06 (4H, m), 8.02-8.24 (1H, m), 8.38-8.65 (1H, m), 11.16-14.80 (1H, m).

B) 3-acetyl-1-[2-fluoro-4-(1H-pyrazol-1-yl)phenyl]furo[3,2-c]pyridazin-4(1H)-one A suspension of 1-(3-bromofuran-2-yl)-2-{[2-fluoro-4-(1H-pyrazol-1-yl)phenyl]hydrazono}butane-1,3-dione (5.3 g) and potassium carbonate (3.5 g) in DMF (40 mL) was stirred at 90° C. for 4 hr. The reaction mixture was poured into water, and the mixture was extracted with ethyl acetate. The extract was washed with water and saturated brine, dried over anhydrous magnesium sulfate, and concentrated under reduced pressure. The residue was suspended in diisopropylether, and the precipitate was collected by filtration to give the title compound (2.56 g).

MS (ESI+): [M+H]$^+$ 339.2

C) 1-[2-fluoro-4-(1H-pyrazol-1-yl)phenyl]-3-(1-phenyl-1H-pyrazol-5-yl)furo[3,2-c]pyridazin-4(1H)-one A solution of 3-acetyl-1-[2-fluoro-4-(1H-pyrazol-1-yl) phenyl]furo[3,2-c]pyridazin-4(1H)-one (500 mg), N,N-dimethylformamide dimethyl acetal (2.5 mL) and acetonitrile (2.5 mL) was heated under reflux for 1.5 hr. After cooling to room temperature, the reaction mixture was concentrated under reduced pressure.

A solution of the obtained residue and phenylhydrazine (168 mg) in TFA/ethanol (5/95, 20 mL) was stirred at room temperature for 3 days. The reaction mixture was filtered. To the filtrate was added saturated aqueous sodium hydrogen carbonate solution. The mixture was extracted with ethyl acetate. The extract was washed with water and saturated brine, dried over anhydrous magnesium sulfate, and concentrated under reduced pressure. The residue was purified by silica gel column chromatography (ethyl acetate/hexane) to give the title compound (250 mg).

MS (ESI+): [M+H]$^+$ 439.3

Example 4

1-[2-fluoro-4-(1H-pyrazol-1-yl)phenyl]-3-(1-phenyl-1H-pyrazol-5-yl)-6,7-dihydrofuro[3,2-c]pyridazin-4(1H)-one A suspension of 1-[2-fluoro-4-(1H-pyrazol-1-yl)phenyl]-3-(1-phenyl-1H-pyrazol-5-yl)furo[3,2-c]pyridazin-4(1H)-one (100 mg) and 10% palladium on carbon (100 mg) in ethanol/THF (3/1, 40 mL) was stirred at 50° C. for 12 hr under a hydrogen atmosphere. Palladium on carbon was removed by filtration, and the filtrate was concentrated under reduced pressure. The residue was purified by silica gel column chromatography (ethyl acetate/methanol) and crystallized from hexane/ethyl acetate to give the title compound (74 mg).

MS (ESI+): [M+H]$^+$ 441.2

Example 5

3-(1-phenyl-1H-pyrazol-5-yl)-1-[4-(1H-pyrazol-1-yl)-2-(2,2,2-trifluoroethoxy)phenyl]furo[3,2-c]pyridazin-4(1H)-one To a solution of 2,2,2-trifluoroethanol (48 mg) in DMF (1 mL) was added 60% NaH (19.2 mg) under ice-cooling. The reaction mixture was stirred at room temperature for 30 min, and 1-[2-fluoro-4-(1H-pyrazol-1-yl)phenyl]-3-(1-phenyl-1H-pyrazol-5-yl)furo[3,2-c]pyridazin-4(1H)-one (70 mg) was added. The reaction mixture was stirred at 100° C. for 6 hr, and saturated aqueous sodium hydrogen carbonate solution was added. The reaction mixture was extracted with ethyl acetate, the extract was dried over anhydrous magnesium sulfate, and the solvent was evaporated under reduced pressure. The residue was purified by silica gel column chromatography (methanol/ethyl acetate) to give the title compound (45 mg).
MS (ESI+): [M+H]+ 519.1

Example 6

3-(1-phenyl-1H-pyrazol-5-yl)-1-[4-(1H-pyrazol-1-yl)-2-(2,2,2-trifluoroethoxy)phenyl]-6,7-dihydrofuro[3,2-c]pyridazin-4(1H)-one A solution of 3-(1-phenyl-1H-pyrazol-5-yl)-1-[4-(1H-pyrazol-1-yl)-2-(2,2,2-trifluoroethoxy)phenyl]furo[3,2-c]pyridazin-4(1H)-one (35 mg) and 10% palladium on carbon (50 mg) in ethanol (5 mL) was stirred at 50° C. for 12 hr under a hydrogen atmosphere. Palladium on carbon was removed by filtration, and the filtrate was concentrated under reduced pressure. The residue was purified by silica gel column chromatography (ethyl acetate/methanol) to give the title compound (7 mg).
MS (ESI+): [M+H]+ 521.3

Example 7

1-(4-iodophenyl)-3-(1-phenyl-1H-pyrazol-5-yl)furo[3,2-c]pyridazin-4(1H)-one

The title compound (750 mg) was obtained in the same manner as in Example 3.
MS (ESI+): [M+H]+ 480.8

Example 8

3-(1-phenyl-1H-pyrazol-5-yl)-1-[4-(1H-pyrazol-1-yl)phenyl]-6,7-dihydrofuro[3,2-c]pyridazin-4(1H)-one A) 3-(1-phenyl-1H-pyrazol-5-yl)-1-[4-(1H-pyrazol-1-yl)phenyl]furo[3,2-c]pyridazin-4(1H)-one A suspension of 1-(4-iodophenyl)-3-(1-phenyl-1H-pyrazol-5-yl)furo[3,2-c]pyridazin-4(1H)-one (200 mg), pyrazole (57 mg), copper oxide (6 mg), 2-hydroxybenzaldehydeoxime (23 mg) and cesium carbonate (271 mg) in DMF (5 mL) was stirred at 50° C. for 12 hr, and water was added. The reaction mixture was extracted with ethyl acetate, the extract was washed with saturated brine, and the solvent was evaporated under reduced pressure. The residue was purified by silica gel column chromatography (methanol/ethyl acetate) to give the title compound (64 mg).
MS (ESI+): [M+H]+ 421.3

B) 3-(1-phenyl-1H-pyrazol-5-yl)-1-[4-(1H-pyrazol-1-yl)phenyl]-6,7-dihydrofuro[3,2-c]pyridazin-4(1H)-one A solution of 3-(1-phenyl-1H-pyrazol-5-yl)-1-[4-(1H-pyrazol-1-yl)phenyl]furo[3,2-c]pyridazin-4(1H)-one (64 mg) and 10% palladium on carbon (100 mg) in ethanol (80 mL) was stirred at 50° C. for 12 hr under a hydrogen atmosphere. Palladium on carbon was removed by filtration, and the filtrate was concentrated under reduced pressure. The residue was purified by silica gel column chromatography (ethyl acetate/methanol) to give the title compound (21 mg).
MS (ESI+): [M+H]+ 423.4

Example 9

1-[4-iodo-3-(trifluoromethoxy)phenyl]-3-(1-phenyl-1H-pyrazol-5-yl)furo[3,2-c]pyridazin-4(1H)-one A) 1-(3-bromofuran-2-yl)-2-{[4-iodo-3-(trifluoromethoxy)phenyl]hydrazono}butane-1,3-dione To a solution of 3-(trifluoromethoxy)aniline (2 g) in acetonitrile (20 mL) was added N-iodosuccinimide (2.5 g) under ice-cooling. The reaction mixture was stirred at 0° C. for 3 hr, water was added, and the mixture was extracted with ethyl acetate. The extract was washed with saturated brine, dried over anhydrous magnesium sulfate, and concentrated under reduced pressure to give an oily compound (4.0 g). To a mixture of the obtained oily compound (2.6 g) and 6M hydrochloric acid (8.7 mL) was added dropwise a solution of sodium nitrite (0.89 g) in water (2 mL) at 0° C., and the mixture was stirred for 15 min. The obtained aqueous solution was added to a suspension, which was cooled to 0° C., of 1-(3-bromofuran-2-yl)butane-1,3-dione (2 g) and sodium acetate (4.3 g) in methanol (20 mL). The reaction mixture was poured into water, and the mixture was extracted with ethyl acetate. The extract was washed with saturated aqueous sodium hydrogen carbonate solution and saturated brine, dried over anhydrous magnesium sulfate, and concentrated under reduced pressure. The residue was washed with diisopropyl ether to give the title compound (3.9 g).
$^1$H NMR (300 MHz, DMSO-$d_6$) δ 2.46 (3H, s), 7.01-7.09 (1H, m), 7.18-7.26 (1H, m), 7.39 (1H, s), 7.83-7.96 (1H, m), 8.13-8.18 (1H, m), 11.39 (1H, s).

B) 3-acetyl-1-[4-iodo-3-(trifluoromethoxy)phenyl]furo[3,2-c]pyridazin-4(1H)-one

The title compound (0.75 g) was obtained in the same manner as in step B of Example 3.
MS (ESI+): [M+H]+ 465.1

C) 1-[4-iodo-3-(trifluoromethoxy)phenyl]-3-(1-phenyl-1H-pyrazol-5-yl)furo[3,2-c]pyridazin-4(1H)-one The title compound (0.35 g) was obtained in the same manner as in step C of Example 3.
MS (ESI+): [M+H]+ 565.1

Example 10

3-(1-phenyl-1H-pyrazol-5-yl)-1-[3-(trifluoromethoxy)phenyl]furo[3,2-c]pyridazin-4(1H)-one A suspension of 1-[4-iodo-3-(trifluoromethoxy)phenyl]-3-(1-phenyl-1H-pyrazol-5-yl)furo[3,2-c]pyridazin-4(1H)-one (300 mg), pyrazole (72 mg), copper oxide(I) (7.6 mg), 2-hydroxybenzaldehydeoxime (29 mg) and cesium carbonate (346 mg) in DMF (5 mL) was stirred at 50° C. for 12 hr, and water was added. The reaction mixture was extracted with ethyl acetate, the extract was dried over anhydrous magnesium sulfate, and the solvent was evaporated under reduced pressure. The residue was purified by silica gel column chromatography (methanol/ethyl acetate) to give the title compound (25 mg).
MS (ESI+): [M+H]+ 439.3

Example 11

2-(1-phenyl-1H-pyrazol-5-yl)pyridazino[6,1-c][1,4]benzoxazin-3(5H)-one

A) 2-tert-butoxy aniline

To a solution of 1-tert-butoxy-2-nitrobenzene (Journal of Organic Chemistry, 1998, 63, 25, 9495-9496.) (15.0 g) in methanol (300 mL) was added 10% palladium on carbon (1.67 g), and the mixture was stirred at room temperature for 30 hr under a hydrogen atmosphere. Palladium on carbon was removed by filtration, and the filtrate was concentrated under reduced pressure. The residue was purified by silica gel column chromatography (hexane/ethyl acetate) to give the title compound (12.4 g).

$^1$H NMR (300 MHz, DMSO-$d_6$) δ 1.30 (8H, s), 4.66 (2H, s), 6.44 (1H, dd, J=15.1, 1.9 Hz), 6.55-6.71 (1H, m), 6.71-6.95 (2H, m).

B) 3-[(2-tert-butoxyphenyl)hydrazono]pentane-2,4-dione

The title compound (7.75 g) was obtained in the same manner as in step D of Example 1.

$^1$H NMR (300 MHz, DMSO-$d_6$) δ 1.43 (9H, s), 2.43 (3H, s), 2.50 (3H, s), 7.02-7.29 (3H, m), 7.76 (1H, dd, J=7.54, 1.88 Hz), 14.59 (1H, s)

C) 1-(benzyloxy)-5-[(2-tert-butoxyphenyl)hydrazono]heptane-2,4,6-trione

NaH (4.28 g) was suspended in THF (30 mL), and a solution of 3-[(2-tert-butoxyphenyl)hydrazono]pentane-2,4-dione (7.47 g) in THF (100 mL) was added dropwise at 0° C. The reaction mixture was stirred at 0° C. for 40 min, a solution of (benzyloxy)acetylchloride (5.55 mL) in THF (20 mL) was added at 0° C., and the mixture was stirred at 0° C. for 5 hr. The reaction mixture was poured into water, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (5.58 g).

MS (API−): [M−H]⁻ 423.4

D) 3-acetyl-6-[(benzyloxy)methyl]-1-(2-tert-butoxyphenyl)pyridazin-4(1H)-one A solution of 1-(benzyloxy)-5-[(2-tert-butoxyphenyl)hydrazono]heptane-2,4,6-trione (5.58 g) and triethylamine (9.61 g) in acetonitrile (55 mL) was heated under reflux for 1 hr. After cooling, the solvent was evaporated under reduced pressure, and the residue was purified by silica gel column chromatography (hexane/ethyl acetate) to give the title compound (3.52 g).

MS (API+): [M+H]⁺ 407.0

E) 6-[(benzyloxy)methyl]-1-(2-tert-butoxyphenyl)-3-(1-phenyl-1H-pyrazol-5-yl)pyridazin-4(1H)-one The title compound (4.44 g) was obtained in the same manner as in step F of Example 1.

MS (API+): [M+H]⁺ 507.2

F) 6-(hydroxymethyl)-1-(2-hydroxyphenyl)-3-(1-phenyl-1H-pyrazol-5-yl)pyridazin-4(1H)-one A solution of 6-[(benzyloxy)methyl]-1-(2-tert-butoxyphenyl)-3-(1-phenyl-1H-pyrazol-5-yl)pyridazin-4(1H)-one (0.89 g) in TFA (9 mL) was heated under reflux for 4 hr. After cooling, the solvent was evaporated under reduced pressure, and the residue was purified by silica gel column chromatography (ethyl acetate/methanol) to give the title compound (0.19 g).

MS (ESI+): [M+H]⁺ 361.4

G) 2-(1-phenyl-1H-pyrazol-5-yl)pyridazino[6,1-c][1,4]benzoxazin-3(5H)-one 6-(Hydroxymethyl)-1-(2-hydroxyphenyl)-3-(1-phenyl-1H-pyrazol-5-yl)pyridazin-4(1H)-one (190 mg) was dissolved in toluene (2 mL) and THF (3 mL), triphenylphosphine (202 mg) and 1.9M DIAD toluene solution (410 μL) were added at 0° C., and the reaction mixture was stirred at room temperature for 1 hr. To the reaction mixture was added saturated aqueous sodium hydrogen carbonate solution, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (130 mg).

MS (ESI+): [M+H]⁺ 343.1

Example 12

3-methoxy-6-phenyl-2-(1-phenyl-1H-pyrazol-5-yl)-4H-pyran-4-one

A) 1-phenylheptane-1,3,4,6-tetrone

To a mixture of diethyl ethanedioate (7.0 mL), acetone (3.8 mL) and benzene (70 mL) was added sodium (1.2 g) at room temperature, and the mixture was stirred at room temperature for 1 hr. The resulting solid was collected by filtration, and benzene (70 mL) and acetophenone (6.0 mL) were added thereto. Sodium (1.2 g) was added, and the mixture was stirred with heating at 100° C. for 2 hr. After cooling to room temperature, the resulting solid was collected by filtration. The obtained solid was acidified with 6N hydrochloric acid, and the mixture was extracted with ethyl acetate. The extract was dried over anhydrous sodium sulfate, and concentrated under reduced pressure. The residue was purified by silica gel column chromatography (ethyl acetate/hexane) to give the title compound (3.6 g).

$^1$H NMR (400 MHz, CDCl$_3$) δ 2.28 (3H, s), 6.43 (1H, s), 7.06 (1H, s), 7.51 (2H, t, J=7.6 Hz), 7.60 (1H, t, J=7.6 Hz), 8.01 (2H, d, J=7.6 Hz).

B) 2-acetyl-3-hydroxy-6-phenyl-4H-pyran-4-one

A mixture of 1-phenylheptane-1,3,4,6-tetrone (2.3 g), iodobenzene diacetate (6.7 g) and acetic acid (80 mL) was stirred at room temperature for 16 hr, the reaction mixture was diluted with water, and the mixture was extracted with ethyl acetate. The extract was dried over anhydrous magnesium sulfate and concentrated under reduced pressure. The residue was purified by silica gel column chromatography (ethyl acetate/hexane) to give the title compound (0.32 g).

$^1$H NMR (400 MHz, CDCl$_3$) δ 2.72 (3H, s), 6.95 (1H, s), 7.52-7.58 (4H, m), 7.82 (2H, dd, J=1.6, 8.0 Hz).

C) 2-acetyl-3-methoxy-6-phenyl-4H-pyran-4-one

A mixture of 2-acetyl-3-hydroxy-6-phenyl-4H-pyran-4-one (200 mg), potassium carbonate (150 mg), iodomethane (0.0600 mL) and DMF (5.0 mL) was stirred at room temperature overnight. The reaction mixture was diluted with water and the mixture was extracted with ethyl acetate. The extract was dried over anhydrous sodium sulfate, and concentrated under reduced pressure. The residue was purified by silica gel column chromatography (ethyl acetate/hexane) to give the title compound (90.0 mg).
$^1$H NMR (400 MHz, CDCl$_3$) δ 2.68 (3H, s), 4.14 (3H, s), 6.91 (1H, s), 7.48-7.56 (3H, m), 7.84 (2H, d, J=8.0 Hz).

D) 3-methoxy-6-phenyl-2-(1-phenyl-1H-pyrazol-5-yl)-4H-pyran-4-one

The title compound was obtained in the same manner as in step F of Example 1.
MS (ESI+), found: 345.3

Example 13

5-phenyl-3-(1-phenyl-1H-pyrazol-5-yl)pyrazin-2(1H)-one

A) 5-phenylpyrazin-2(1H)-one

To a mixture of glycine amide hydrochloride (0.73 g), methanol (6.0 mL) and water (1.5 mL) were added a 12.5M aqueous sodium hydroxide solution (0.80 mL) and a solution of sodium hydroxide (0.26 g) in methanol (3.0 mL) at −30° C. Then, a solution of oxo(phenyl)acetaldehyde (1.0 g) in methanol (5.0 mL) was added, and the mixture was stirred at −20° C. for 2 hr and at room temperature for 1 hr. The reaction mixture was neutralized with acetic acid, and the resulting solid was collected by filtration and washed with water to give the title compound (0.86 g).
$^1$H NMR (400 MHz, DMSO-d$_6$) δ 7.29-7.33 (1H, m), 7.40-7.44 (2H, m), 7.86-7.88 (2H, m), 8.09 (1H, d, J=1.2 Hz), 8.11 (1H, d, J=1.6 Hz), 12.55 (1H, brs).

B) 3-bromo-5-phenylpyrazin-2(1H)-one

A mixture of 5-phenylpyrazin-2(1H)-one (0.86 g), N-bromosuccinimide (0.89 g) and DMF (16 mL) was stirred at room temperature for 2 hr. The reaction mixture was diluted with water, and the mixture was extracted with ethyl acetate. The extract was dried over anhydrous sodium sulfate, and concentrated under reduced pressure. The residue was washed with hexane to give the title compound (0.18 g).
$^1$H NMR (400 MHz, DMSO-d$_6$) δ 7.33-7.35 (1H, m), 7.41-7.45 (2H, m), 7.81-7.83 (2H, m), 8.12 (1H, s), 13.03 (1H, brs).

C) 2-(benzyloxy)-3-bromo-5-phenylpyrazine

A mixture of 3-bromo-5-phenylpyrazin-2(1H)-one (0.16 g), silver carbonate (0.18 g), benzyl bromide (0.080 mL) and toluene (6.0 mL) was heated under reflux for 3 hr. The reaction mixture was cooled to room temperature, filtered through celite, and the filtrate was concentrated under reduced pressure. The residue was purified by silica gel column chromatography (ethyl acetate/hexane) to give the title compound (0.21 g).
$^1$H NMR (400 MHz, CDCl$_3$) δ 5.51 (2H, s), 7.33-7.37 (1H, m), 7.39-7.43 (3H, m), 7.44-7.53 (4H, m), 7.90-7.93 (2H, m), 8.45 (1H, s).

D) (1-phenyl-1H-pyrazol-5-yl)boronic acid

To a solution of 1-phenyl-1H-pyrazole (20.0 g) in THF (700 mL) was added dropwise n-butyllithium (2.5 M hexane solution, 58.3 mL) at −78° C. under a nitrogen atmosphere, and the mixture was stirred at the same temperature for 30 min. To the reaction mixture was added triisopropyl borate (52.2 g) at −78° C., and the mixture was stirred at the same temperature for 1 hr, gradually warmed to room temperature, and stirred at room temperature for 20 hr. The reaction mixture was adjusted to pH 5 with acetic acid (20 mL) and concentrated to give the title compound (25.0 g).
MS (ESI+): [M+H]$^+$189.0.

E) 1-phenyl-5-(4,4,5,5-tetramethyl-1,3,2-dioxaborolan-2-yl)-1H-pyrazole (1-Phenyl-1H-pyrazol-5-yl)boronic acid (25.0 g) was dissolved in toluene (700 mL), pinacol (18.0 g) was added at room temperature, and the mixture was stirred at 40° C. for 2 days. The reaction mixture was diluted with dichloromethane, washed with water and saturated brine, dried over anhydrous sodium sulfate, filtered and concentrated. The resulting solid was collected by filtration and washed with hexane to give the title compound (19.8 g).
$^1$H NMR (400 MHz, CDCl$_3$) δ 1.27 (12H, s), 6.89 (1H, d, J=1.6 Hz), 7.33-7.43 (3H, m), 7.52-7.55 (2H, m), 7.72 (1H, d, J=1.6 Hz).

F) 2-(benzyloxy)-5-phenyl-3-(1-phenyl-1H-pyrazol-5-yl)pyrazine

A mixture of 2-(benzyloxy)-3-bromo-5-phenylpyrazine (0.17 g), 1-phenyl-5-(4,4,5,5-tetramethyl-1,3,2-dioxaborolan-2-yl)-1H-pyrazole (0.20 g), X-phos (24 mg), Pd$_2$(dba)$_3$ (11 mg), 2M aqueous cesium carbonate solution (0.62 mL) and 1,2-dimethoxyethane (5.0 mL) was stirred at 110° C. for 1 hr under microwave irradiation. The reaction mixture was cooled to room temperature, filtered through celite, and the filtrate was concentrated under reduced pressure. The residue was purified by silica gel column chromatography (ethyl acetate/hexane) to give the title compound (0.21 g).
$^1$H NMR (400 MHz, CDCl$_3$) δ 5.44 (2H, s), 7.06 (1H, d, J=2.0 Hz), 7.28-7.40 (15H, m), 7.77 (1H, d, J=2.0 Hz), 8.47 (1H, s).

G) 5-phenyl-3-(1-phenyl-1H-pyrazol-5-yl)pyrazin-2(1H)-one

The title compound was obtained in the same manner as in step A of Example 2.
MS (ESI+), found: 315.3

Example 14

3-hydroxy-6-phenyl-2-(1-phenyl-1H-pyrazol-5-yl)-4H-pyran-4-one

A) 2-acetyl-3-(benzyloxy)-6-phenyl-4H-pyran-4-one

A mixture of 2-acetyl-3-hydroxy-6-phenyl-4H-pyran-4-one (0.53 g), potassium carbonate (0.40 g), benzyl bromide (0.27 mL) and DMF (10 mL) was stirred at room temperature for 2 hr. The reaction mixture was diluted with water, and extracted with ethyl acetate. The extract was dried over anhydrous sodium sulfate, and concentrated under reduced pressure. The residue was purified by silica gel column chromatography (ethyl acetate/hexane) to give the title compound (0.18 g).
$^1$H NMR (400 MHz, CDCl$_3$) δ 2.51 (3H, s), 5.49 (2H, s), 6.92 (1H, s), 7.34-7.38 (3H, m), 7.45-7.53 (5H, m), 7.82-7.85 (2H, m).

B) 3-(benzyloxy)-6-phenyl-2-(1-phenyl-1H-pyrazol-5-yl)-4H-pyran-4-one

The title compound was obtained in the same manner as in step F of Example 1.
$^1$H NMR (400 MHz, CDCl$_3$) δ 5.39 (2H, s), 6.84 (2H, d, J=8.0 Hz), 6.95 (3H, d, J=8.8 Hz), 6.99 (1H, d, J=1.6 Hz), 7.19 (2H, t, J=7.8 Hz), 7.25 (5H, s), 7.29 (3H, d, J=7.2 Hz), 7.33-7.37 (1H, m), 7.82 (1H, d, J=1.6 Hz).

C) 3-hydroxy-6-phenyl-2-(1-phenyl-1H-pyrazol-5-yl)-4H-pyran-4-one

The title compound was obtained in the same manner as in step A of Example 2.
MS (ESI+), found: 331.3

Example 15

6-phenyl-4-(1-phenyl-1H-pyrazol-5-yl)pyridazin-3(2H)-one

A) 2-benzyl-6-phenyl-4,5-dihydropyridazin-3(2H)-one

To a solution of 4-oxo-4-phenylbutanoic acid (1.0 g) in ethanol (28 mL) were added benzylhydrazine hydrochloride (1.1 g) and sodium acetate (4.2 g) at room temperature, and the mixture was heated under reflux overnight. The solvent was evaporated under reduced pressure, saturated aqueous sodium hydrogen carbonate solution was added, and the mixture was extracted with ethyl acetate. The extract was dried over anhydrous sodium sulfate and concentrated under reduced pressure to give the title compound (0.18 g).
$^1$H NMR (400 MHz, CDCl$_3$) δ 2.63 (2H, t, J=8.0 Hz), 2.96 (2H, t, J=8.2 Hz), 5.03 (2H, s), 7.24-7.27 (2H, m), 7.30-7.34 (2H, m), 7.37-7.42 (4H, m), 7.72-7.74 (2H, m).

B) 3,4-dichloro-6-phenylpyridazine

To a solution of 2-benzyl-6-phenyl-4,5-dihydropyridazin-3(2H)-one (1.4 g) in phosphorus oxychloride (3.0 mL) was added phosphorus pentachloride (7.1 g) at room temperature, and the mixture was heated under reflux overnight. The solvent was evaporated under reduced pressure, and ice water was added. The resulting solid was collected by filtration, washed with water, and the obtained solid was recrystallized from ethanol to give the title compound (0.53 g).
$^1$H NMR (400 MHz, CDCl$_3$) δ 7.54-7.55 (3H, m), 7.96 (1H, s), 8.03-8.05 (2H, m).

C) 4-chloro-6-phenylpyridazin-3(2H)-one

A mixture of 3,4-dichloro-6-phenylpyridazine (0.53 g) and acetic acid (2.6 mL) was heated under reflux for 5 hr, and the solvent was evaporated under reduced pressure. The residue was neutralized with saturated aqueous sodium hydrogen carbonate solution. The obtained solid was collected by filtration and recrystallized from ethanol to give the title compound (0.20 g).
$^1$H NMR (400 MHz, DMSO-d$_3$) δ 7.44-7.51 (3H, m), 7.80-7.90 (2H, m), 8.45 (1H, s), 13.65 (1H, s).

D) 3-(benzyloxy)-4-chloro-6-phenylpyridazine

The title compound was obtained in the same manner as in step C of Example 13.
$^1$H NMR (400 MHz, CDCl$_3$) δ 5.72 (2H, s), 7.28-7.44 (3H, m), 7.48-7.53 (3H, m), 7.54-7.58 (2H, m), 7.89 (1H, s), 7.97-8.00 (2H, m).

E) 3-(benzyloxy)-6-phenyl-4-(1-phenyl-1H-pyrazol-5-yl)pyridazine

The title compound was obtained in the same manner as in step F of Example 13.
$^1$H NMR (400 MHz, CDCl$_3$) δ 5.49 (2H, s), 6.81 (1H, d, J=2.0 Hz), 7.27-7.29 (4H, m), 7.33-7.36 (6H, m), 7.44-7.47 (3H, m), 7.56 (1H, d, J=2.0 Hz), 7.79-7.82 (3H, m).

F) 6-phenyl-4-(1-phenyl-1H-pyrazol-5-yl)pyridazin-3(2H)-one

The title compound was obtained in the same manner as in step A of Example 2.
MS (ESI+), found: 315.3

Example 16

5-phenyl-3-(1-phenyl-1H-pyrazol-5-yl)pyridin-2(1H)-one

A) 5-phenylpyridin-2(1H)-one

A mixture of 5-bromopyridin-2(1H)-one (500 mg), phenylboronic acid (385 mg), tetrakis(triphenylphosphine)palladium(0) (498 mg), 2M aqueous sodium carbonate solution (2.87 mL) and toluene (7.0 mL) was stirred at 100° C. for 1 hr under microwave irradiation. The reaction mixture was cooled to room temperature, and filtered through celite. To the filtrate was added saturated aqueous sodium hydrogen carbonate solution, and the mixture was extracted with ethyl acetate. The extract was dried over anhydrous sodium sulfate and concentrated under reduced pressure. The residue was purified by silica gel column chromatography (ethyl acetate/hexane) to give the title compound (100 mg).
$^1$H NMR (400 MHz, CDCl$_3$) δ 6.71 (1H, d, J=9.2 Hz), 7.31-7.36 (1H, m), 7.42-7.43 (4H, m), 7.65 (1H, d, J=2.4 Hz), 7.80 (1H, dd, J=9.4, 2.6 Hz), 13.62 (1H, brs).

B) 3-bromo-5-phenylpyridin-2(1H)-one

The title compound was obtained in the same manner as in step B of Example 13.
$^1$H NMR (400 MHz, CDCl$_3$) δ 7.31 (1H, t, J=7.2 Hz), 7.41 (2H, t, J=7.8 Hz), 7.60 (2H, d, J=7.2 Hz), 7.79 (1H, d, J=2.4 Hz), 8.32 (1H, d, J=2.4 Hz), 12.40 (1H, s).

C) 2-(benzyloxy)-3-bromo-5-phenylpyridine

The title compound was obtained in the same manner as in step C of Example 13.

¹H NMR (400 MHz, CDCl₃) δ 5.51 (2H, s), 7.30-7.41 (5H, m), 7.43-7.46 (2H, m), 7.49-7.53 (3H, m), 8.05 (1H, d, J=2.4 Hz), 8.31 (1H, d, J=2.4 Hz).

D) 2-(benzyloxy)-5-phenyl-3-(1-phenyl-1H-pyrazol-5-yl)pyridine

The title compound was obtained in the same manner as in step F of Example 13.
¹H NMR (400 MHz, CDCl₃) δ 5.22 (2H, s), 6.62 (1H, d, J=2.0 Hz), 7.16-7.18 (3H, m), 7.28-7.29 (7H, m), 7.30-7.45 (5H, m), 7.71 (1H, d, J=2.4 Hz), 7.76 (1H, d, J=2.0 Hz), 8.39 (1H, d, J=2.4 Hz).

E) 5-phenyl-3-(1-phenyl-1H-pyrazol-5-yl)pyridin-2(1H)-one

The title compound was obtained in the same manner as in step A of Example 2.
MS (ESI+), found: 314.3

Example 17

2-phenyl-6-(1-phenyl-1H-pyrazol-5-yl)pyrimidin-4(3H)-one

A) 1-(1-phenyl-1H-pyrazol-5-yl)ethanone

To a mixture of 2-(phenylhydrazono)ethanal (3.10 g) (Journal of Chemical Society, Perkin Trans. 1, 1981, 503-513.), potassium carbonate (4.40 g) and dioxane (20.0 mL) was added 1-chloropropan-2-one (2.10 g) at room temperature, and the mixture was heated under reflux for 5 hr. The reaction mixture was concentrated under reduced pressure and extracted with dichloromethane. The extract was washed with saturated brine, dried over anhydrous sodium sulfate, and the solvent was evaporated under reduced pressure. The residue was purified by silica gel column chromatography (dichloromethane/methanol) to give the title compound (1.35 g).
¹H-NMR (400 MHz, CDCl₃) δ 2.50 (3H, s), 6.99 (1H, d, J=2.0 Hz), 7.36-7.38 (2H, m), 7.43-7.460 (3H, m), 7.69 (1H, d, J=2.4 Hz).

B) ethyl 3-oxo-3-(1-phenyl-1H-pyrazol-5-yl)propanoate

To a mixture of diethyl carbonate (20.0 mL) and 60% NaH (0.34 g) was added 1-(1-phenyl-1H-pyrazol-5-yl)ethanone (1.30 g) at room temperature, and the mixture was heated under reflux for 2 hr. To the reaction mixture was added water, and the mixture was extracted with dichloromethane. The extract was washed with saturated brine, dried over anhydrous sodium sulfate, and the solvent was evaporated under reduced pressure. The residue was purified by silica gel column chromatography (petroleum ether/ethyl acetate) to give the title compound (1.10 g).
¹H-NMR (400 MHz, CDCl₃) δ 1.25 (3H, t, J=7.2 Hz), 3.83 (2H, s), 4.19 (2H, q, J=7.2 Hz), 6.76 (1H, d, J=2.0 Hz), 7.39-7.48 (5H, m), 7.71 (1H, d, J=2.0 Hz).

C) 2-phenyl-6-(1-phenyl-1H-pyrazol-5-yl)pyrimidin-4(3H)-one

To a solution of ethyl 3-oxo-3-(1-phenyl-1H-pyrazol-5-yl)propanoate (300 mg) in DMF (10.0 mL) was added benzenecarboximidamide (139 mg) at room temperature. The reaction mixture was heated using a microwave reactor at 140° C. for 30 min. The reaction mixture was extracted with dichloromethane. The extract was washed with saturated brine, dried over anhydrous sodium sulfate, and the solvent was evaporated under reduced pressure. The residue was purified by silica gel column chromatography (dichloromethane/methanol) to give the title compound (100 mg).
MS (ESI+): [M+H]⁺ 315.1

Example 18

3-(1-phenyl-1H-pyrazol-5-yl)-1-[3-(trifluoromethyl)phenyl]pyridin-4(1H)-one

A) 3-chloro-1-[3-(trifluoromethyl)phenyl]pyridin-4(1H)-one

3-Chloropyridin-4-ol (0.259 g), 1-fluoro-3-(trifluoromethyl)benzene (0.126 mL) and potassium carbonate (0.276 g) were suspended in N-methyl-2-pyrrolidone (1.2 mL), and the suspension was stirred at 150° C. for 2 hr. The reaction mixture was cooled to room temperature, diluted with water, extracted with ethyl acetate, dried over anhydrous magnesium sulfate, filtered, concentrated, and purified by silica gel column chromatography (ethyl acetate/hexane→methanol/ethyl acetate) to give the title compound (28.1 mg).
MS (ESI+): [M+H]⁺ 274.3 and 276.2.

B) 3-(1-phenyl-1H-pyrazol-5-yl)-1-[3-(trifluoromethyl)phenyl]pyridin-4(1H)-one

3-Chloro-1-[3-(trifluoromethyl)phenyl]pyridin-4(1H)-one (0.0247 g), 1-phenyl-5-(4,4,5,5-tetramethyl-1,3,2-dioxaborolan-2-yl)-1H-pyrazole (0.0365 g), potassium carbonate (0.0249 g) and bis(di-tert-butyl(4-dimethylaminophenyl)phosphine)dichloropalladium(II) (0.0032 g) were suspended in toluene (1 mL) and water (0.1 mL), and the suspension was heated under reflux for 22 hr under an argon atmosphere. To the reaction mixture were added 1-phenyl-5-(4,4,5,5-tetramethyl-1,3,2-dioxaborolan-2-yl)-1H-pyrazole (0.0365 g) and potassium carbonate (0.0249 g) at room temperature, and the mixture was heated under reflux for 1 day under an argon atmosphere. The reaction mixture was cooled to room temperature, diluted with aqueous sodium hydrogen carbonate solution, extracted with ethyl acetate, dried over anhydrous sodium sulfate, filtered, concentrated, and purified by NH silica gel column chromatography (ethyl acetate/hexane) to give the title compound (1.2 mg).
MS (ESI+): [M+H]⁺ 382.3.

Example 19

5-(1-phenyl-1H-pyrazol-5-yl)-1-[3-(trifluoromethyl)phenyl]pyridazin-4(1H)-one

A) 3-bromo-5-methoxy-1-[3-(trifluoromethyl)phenyl]pyridazin-4(1H)-one

Isoamyl nitrite (4.95 mL) and copper(II) bromide (3.83 g) were suspended in DMF (41 mL), and a solution of 3-amino-5-methoxy-1-[3-(trifluoromethyl)phenyl]pyridazin-4(1H)-one (4.09 g) in DMF (20 mL) was added at 0° C. The reaction mixture was stirred at 0° C. for 1 hr and further at 60° C. for 3 hr. The reaction mixture was diluted with brine, extracted with ethyl acetate, dried over anhydrous magnesium sulfate, filtered, concentrated, purified by silica gel column chromatography (ethyl acetate/hexane), and solidified in ethyl acetate/hexane to give the title compound (3.69 g).
MS (ESI+): [M+H]$^+$ 349.1 and 351.2.

B) 5-methoxy-1-[3-(trifluoromethyl)phenyl]pyridazin-4(1H)-one

3-Bromo-5-methoxy-1-[3-(trifluoromethyl)phenyl]pyridazin-4(1H)-one (0.800 g) and palladium on carbon (0.24 g, palladium 10%, 50% water moistened product) were suspended in THF (14 mL), and the suspension was stirred at room temperature for 2.5 days under a hydrogen atmosphere. The reaction mixture was filtered through celite, and the filtrate was concentrated and purified by silica gel column chromatography (ethyl acetate/hexane→methanol/ethyl acetate) to give the title compound (0.185 g).
MS (ESI+): [M+H]$^+$ 271.0.

C) 5-hydroxy-1-[3-(trifluoromethyl)phenyl]pyridazin-4(1H)-one

To a solution of sodium iodide (0.513 g) in acetonitrile (4 mL) was added chlorotrimethylsilane (0.434 mL) at room temperature. The reaction mixture was stirred at room temperature for 30 min, a solution of 5-methoxy-1-[3-(trifluoromethyl)phenyl]pyridazin-4(1H)-one (0.185 g) in acetonitrile (6 mL) was added at room temperature. The reaction mixture was heated under reflux for 3 hr, cooled to room temperature, diluted with water, extracted with ethyl acetate, washed with saturated brine, dried over anhydrous sodium sulfate, filtered, concentrated, and purified by silica gel column chromatography (ethyl acetate/hexane-methanol/ethyl acetate) to give the title compound (0.317 g).
$^1$H NMR (300 MHz, DMSO-d$_6$) δ 7.75-7.87 (2H, m), 8.03 (1H, s), 8.06-8.19 (2H, m), 8.80 (1H, s).

D) 5-oxo-2-[3-(trifluoromethyl)phenyl]-2,5-dihydropyridazin-4-yl trifluoromethanesulfonate 5-Hydroxy-1-[3-(trifluoromethyl)phenyl]pyridazin-4(1H)-one (0.317 g), triethylamine (0.143 mL) and N-phenyl-bis(trifluoromethanesulfonimide) (0.294 g) was stirred in THF (8 mL) at 0° C. for 5 min, and further at room temperature for 1 day. The reaction mixture was diluted with water, extracted with ethyl acetate, washed with saturated brine, dried over anhydrous magnesium sulfate, filtered, concentrated, and purified by silica gel column chromatography (ethyl acetate/hexane) to give the title compound (0.208 g).
MS (ESI+): [M+H]$^+$ 388.8.

E) 5-(1-phenyl-1H-pyrazol-5-yl)-1-[3-(trifluoromethyl)phenyl]pyridazin-4(1H)-one 5-oxo-2-[3-(trifluoromethyl)phenyl]-2,5-dihydropyridazin-4-yl trifluoromethanesulfonate (0.100 g), 1-phenyl-5-(4,4,5,5-tetramethyl-1,3,2-dioxaborolan-2-yl)-1H-pyrazole (0.139 g), sodium carbonate (0.109 g) and tetrakis(triphenylphosphine)palladium(0) (0.0298 g) were suspended in a mixed solvent of toluene (2.06 mL), ethanol (0.52 mL) and water (0.52 mL), and the suspension was stirred at 100° C. for 6 hr under an argon atmosphere. The reaction mixture was cooled to room temperature, diluted with water, extracted with ethyl acetate, washed with aqueous sodium hydrogen carbonate solution and saturated brine, dried over anhydrous magnesium sulfate, filtered, concentrated, purified by NH silica gel column chromatography (ethyl acetate/hexane) and recrystallized from ethyl acetate/hexane to give the title compound (0.0087 g).
MS (ESI+): [M+H]$^+$ 383.3.

Example 20

5-(2-fluorophenyl)-1-(1-phenyl-1H-pyrazol-5-yl)pyridin-2(1H)-one

A) 5-(2-fluorophenyl)pyridin-2(1H)-one

5-Bromopyridin-2(1H)-one (1.04 g), (2-fluorophenyl)boronic acid (0.924 g), sodium carbonate (1.40 g), lithium chloride (0.560 g) and tetrakis(triphenylphosphine)palladium(0) (0.347 g) were suspended in a mixed solvent of toluene (26.4 mL), ethanol (6.6 mL) and water (6.6 mL), and the suspension was stirred at 100° C. for 17 hr under an argon atmosphere. The reaction mixture was cooled to room temperature, diluted with brine, extracted with ethyl acetate, diluted with THF, dried over anhydrous sodium sulfate, filtered, concentrated, and purified by silica gel column chromatography (ethyl acetate/hexane→ethyl acetate/methanol) to give the title compound (0.0563 g).
MS (ESI+): [M+H]$^+$ 190.0.

B) 5-(2-fluorophenyl)-1-(1-phenyl-1H-pyrazol-5-yl)pyridin-2(1H)-one 5-(2-Fluorophenyl)pyridin-2(1H)-one (0.0281 g), 1-phenyl-5-(4,4,5,5-tetramethyl-1,3,2-dioxaborolan-2-yl)-1H-pyrazole (0.0802 g) and copper(II) acetate (0.0539 g) were suspended in pyridine (1.48 mL), and the suspension was stirred at room temperature for 12 hr and further at 90° C. for 6 hr. To the reaction mixture were added 1-phenyl-5-(4,4,5,5-tetramethyl-1,3,2-dioxaborolan-2-yl)-1H-pyrazole (0.0802 g) and copper(II) acetate (0.0539 g) at room temperature, and the mixture was heated under reflux for 1.5 days. The reaction mixture was cooled to room temperature, purified by NH silica gel column chromatography (ethyl acetate/hexane) and recrystallized from ethyl acetate/hexane to give the title compound (0.0007 g).
MS (ESI+): [M+H]$^+$ 332.2.

Example 21

2-(1-phenyl-1H-pyrazol-5-yl)-6-[3-(trifluoromethyl)phenyl]pyridazin-3(2H)-one

A) 6-[3-(trifluoromethyl)phenyl]pyridazin-3(2H)-one

A mixture of 3'-(trifluoromethyl)acetophenone (9.14 mL) and glyoxylic acid monohydrate (1.84 g) was stirred at 100° C. for 2 hr. After cooling to room temperature, water (20 mL) and 25% aqueous ammonia (5 mL) were added, and the mixture was washed with ethyl acetate. To the aqueous layer was added hydrazine monohydrate (1.94 mL), and the mixture was heated under reflux for 2 hr. After cooling to room temperature, the precipitate was collected by filtration and washed with water to give the title compound (2.07 g).
$^1$H NMR (300 MHz, CDCl$_3$) δ 7.13 (1H, d, J=9.8 Hz), 7.61 (1H, t, J=7.9 Hz), 7.71 (1H, d, J=7.9 Hz), 7.80 (1H, d, J=9.8 Hz), 7.99 (1H, d, J=7.9 Hz), 8.08 (1H, s), 11.93 (1H, brs).

B) 2-(1-phenyl-1H-pyrazol-5-yl)-6-[3-(trifluoromethyl)phenyl]pyridazin-3(2H)-one A suspension of 6-[3-(trifluoromethyl)phenyl]pyridazin-3(2H)-one (240 mg), 5-iodo-1-phenyl-1H-pyrazole (540 mg), copper powder (64 mg) and potassium carbonate (415 mg) in pyridine (5 mL) was heated under reflux for 24 hr. The reaction mixture was poured into 1M hydrochloric acid, and the mixture was extracted with ethyl acetate. The extract was washed with saturated brine, dried over anhydrous magnesium sulfate, and concentrated under reduced pressure. The residue was purified by silica gel column chromatography (hexane/ethyl acetate) and recrystallized from hexane/ethyl acetate to give the title compound (56.5 mg).

$^1$H NMR (300 MHz, CDCl$_3$) δ 6.70 (1H, d, J=1.9 Hz), 7.09 (1H, d, J=10.2 Hz), 7.28-7.42 (5H, m), 7.51-7.56 (1H, m), 7.66-7.73 (4H, m), 7.82 (1H, d, J=2.3 Hz).

Example 22

1-(1-benzylpiperidin-3-yl)-3-(1-phenyl-1H-pyrazol-5-yl)pyridazin-4(1H)-one

To a solution of 3-(1-phenyl-1H-pyrazol-5-yl)-1-pyridin-3-ylpyridazin-4(1H)-one (500 mg) in acetonitrile (5 mL) was added benzylbromide (0.19 mL) at room temperature, and the mixture was heated under reflux for 5 hr. The reaction mixture was concentrated under reduced pressure, and the residue was diluted with ethyl acetate. The obtained solution was washed with water and saturated brine, dried over anhydrous sodium sulfate, and the solvent was evaporated under reduced pressure. The obtained residue was dissolved in methanol (10 mL), and platinum dioxide (54 mg) was added. The reaction mixture was stirred at room temperature for 24 hr under a hydrogen atmosphere (3 atm) and filtered through celite. The filtrate was concentrated under reduced pressure, and the obtained residue was diluted with ethyl acetate. The obtained solution was washed with water and saturated brine, dried over anhydrous sodium sulfate, and the solvent was evaporated under reduced pressure. The obtained residue was purified by silica gel column chromatography (methanol/ethyl acetate) to give the title compound (270 mg).

MS (ESI+), found: 412.3

Example 23

1-benzyl-5-methoxy-3-(1-phenyl-1H-pyrazol-5-yl)pyridazin-4(1H)-one

A) 3-chloro-5-methoxypyridazin-4-ol

3-Chloro-4,5-dimethoxypyridazine (17.0 g) and morpholine (59.0 mL) were stirred at 100° C. for 2 hr and the mixture was cooled to 0° C. To the reaction mixture was added phenyl isocyanate (73.8 mL) at 0° C., and the mixture was stirred at the same temperature for 30 min and diluted with ethyl acetate. The resulting N-phenylmorpholine-4-carboxamide was removed by filtration. The filtrate was concentrated and purified by silica gel column chromatography (ethyl acetate/hexane→methanol/ethyl acetate) to give the title compound (9.61 g).

$^1$H NMR (400 MHz, CD$_3$OD) δ 3.88 (3H, s), 8.26 (1H, s).

B) 1-benzyl-3-chloro-5-methoxypyridazin-4(1H)-one

3-Chloro-5-methoxypyridazin-4-ol (10.0 g) was dissolved in DMF (300 mL), NaH (3.26 g, 55 wt %) and tetrabutylammoniumiodide (4.60 g) were added at 0° C., and the mixture was stirred at the same temperature for 10 min. To the reaction mixture was added benzylbromide (12.3 g) at 0° C., and the mixture was stirred at room temperature for 20 hr. The reaction mixture was diluted with water, extracted with dichloromethane, washed with water and saturated brine, dried over anhydrous sodium sulfate, filtered, concentrated, and recrystallized from ethyl acetate/hexane to give the title compound (19.8 g).

$^1$H NMR (400 MHz, CDCl$_3$) δ 3.82 (3H, s), 5.31 (2H, s), 7.34-7.42 (5H, m), 7.89 (1H, s).

C) 1-benzyl-5-methoxy-3-(1-phenyl-1H-pyrazol-5-yl)pyridazin-4(1H)-one

1-Benzyl-3-chloro-5-methoxypyridazin-4(1H)-one (13.6 g), 1-phenyl-5-(4,4,5,5-tetramethyl-1,3,2-dioxaborolan-2-yl)-1H-pyrazole (22.0 g), potassium carbonate (51.0 g) and bis(di-tert-butyl(4-dimethylaminophenyl)phosphine)dichloropalladium(II) (1.92 g) were suspended in toluene (330 mL) and water (33.0 mL), and the mixture was heated under reflux for 24 hr under a nitrogen atmosphere. The reaction mixture was cooled to room temperature, diluted with water and saturated aqueous sodium hydrogen carbonate solution, extracted with ethyl acetate, dried over anhydrous sodium sulfate, filtered, concentrated, and recrystallized from ethyl acetate/hexane to give the title compound (15.1 g).

$^1$H NMR (400 MHz, DMSO-d$_6$) δ 3.81 (3H, s), 5.10 (2H, s), 6.95 (1H, d, J=1.6 Hz), 7.05-7.07 (2H, m), 7.24-7.38 (8H, m), 7.74 (1H, d, J=1.6 Hz), 8.33 (1H, s).

Example 24

3-(1-phenyl-1H-pyrazol-5-yl)-1-piperidin-3-ylpyridazin-4(1H)-one hydrochloride

A) tert-butyl 3-[4-oxo-3-(1-phenyl-1H-pyrazol-5-yl)pyridazin-1(4H)-yl]piperidine-1-carboxylate To a solution of 3-(1-phenyl-1H-pyrazol-5-yl)-1-pyridin-3-ylpyridazin-4(1H)-one (15.0 g) in acetic acid (95 mL) was added rhodium on carbon (0.73 g). The reaction mixture was stirred at 50° C. for 3 days under a hydrogen atmosphere (3 atm). The reaction mixture was filtered through celite, the filtrate was concentrated under reduced pressure, and the obtained residue was diluted with ethyl acetate. The obtained solution was washed with water and saturated brine, dried over anhydrous sodium sulfate, and the solvent was evaporated under reduced pressure. The obtained residue was dissolved in dichloromethane (95 mL), triethylamine (8.0 mL) and di-tert-butyl dicarbonate (11.0 mL) were added at 0° C., and the mixture was stirred at room temperature for 3 hr. The reaction mixture was concentrated under reduced pressure, and the residue was diluted with ethyl acetate. The obtained solution was washed with water and saturated brine, dried over anhydrous sodium sulfate, and the solvent was evaporated under reduced pressure. The obtained residue was purified by silica gel column chromatography (methanol/ethyl acetate) to give the title compound (15.9 g).

$^1$H NMR (400 MHz, CDCl$_3$) δ 1.18-1.22 (1H, m), 1.37-1.40 (1H, m), 1.45 (9H, s), 1.57-1.61 (1H, m), 1.68-1.71 (1H, m), 2.28-2.31 (1H, m), 2.42 (1H, brs), 3.60-3.65 (1H, m), 3.91 (2H, brs), 6.57 (1H, d, J=8.0 Hz), 7.32-7.37 (3H, m), 7.41-7.45 (3H, m), 7.67 (1H, d, J=7.6 Hz), 7.77-7.78 (1H, m).

B) 3-(1-phenyl-1H-pyrazol-5-yl)-1-piperidin-3-ylpyridazin-4(1H)-one hydrochloride To a solution of tert-butyl 3-[4-oxo-3-(1-phenyl-1H-pyrazol-5-yl)pyridazin-1(4H)-yl]piperidine-1-carboxylate (15.9 g) in dichloromethane (76 mL) was added 4M hydrogen

Example 25

1-(1-benzyl-1,2,3,6-tetrahydropyridin-4-yl)-5-methoxy-3-(1-phenyl-1H-pyrazol-5-yl)pyridazin-4(1H)-one

A) 1-benzyl-4-[4-oxo-3-(1-phenyl-1H-pyrazol-5-yl)pyridazin-1(4H)-yl]pyridinium bromide 5-Methoxy-3-(1-phenyl-1H-pyrazol-5-yl)-1-pyridin-4-ylpyridazin-4(1H)-one (0.49 g) and benzylbromide (0.25 mL) were dissolved in acetonitrile (30 mL), and the mixture was heated under reflux overnight. The solvent was evaporated under reduced pressure, and the obtained crystals were washed with ethyl acetate to give the title compound (0.73 g).

$^1$H NMR (300 MHz, DMSO-$d_6$) δ 3.90 (3H, s), 5.76 (2H, s), 7.26 (1H, d, J=1.9 Hz), 7.37-7.52 (10H, m), 7.79 (2H, d, J=7.4 Hz), 7.86 (1H, d, J=1.9 Hz), 8.72 (1H, s), 9.15 (2H, d, J=7.4 Hz).

B) 1-(1-benzyl-1,2,3,6-tetrahydropyridin-4-yl)-5-methoxy-3-(1-phenyl-1H-pyrazol-5-yl)pyridazin-4(1H)-one To a solution of 1-benzyl-4-[4-oxo-3-(1-phenyl-1H-pyrazol-5-yl)pyridazin-1(4H)-yl]pyridinium bromide (0.73 g) in methanol (30 mL) was added sodium borohydride (0.21 g) at 0° C., and the mixture was stirred at room temperature overnight. To the reaction mixture was added water, and the mixture was extracted with ethyl acetate. The extract was washed with saturated brine, dried over anhydrous magnesium sulfate, and concentrated under reduced pressure. The obtained crystals were washed with ethyl acetate and recrystallized from ethyl acetate to give the title compound (0.15 g).

MS (ESI+), found: 440.2

Example 26

3-(1-phenyl-1H-pyrazol-5-yl)-1-(1-prop-2-en-1-yl-1,2,3,6-tetrahydropyridin-4-yl)pyridazin-4(1H)-one The title compound was obtained in the same manner as in Example 25.

MS (ESI+), found: 360.2

Example 27

5-methoxy-3-(1-phenyl-1H-pyrazol-5-yl)-1-(1-prop-2-en-1-yl-1,2,3,6-tetrahydropyridin-4-yl)pyridazin-4(1H)-one The title compound was obtained in the same manner as in Example 25.

MS (ESI+), found: 390.2 chloride in 1,4-dioxane solution (9.4 mL) at 0° C., and the mixture was stirred at room temperature for 24 hr. The solvent was evaporated under reduced pressure to give the title compound (12.1 g).

MS (ESI+), found: 322.2

Example 28

1-(1-benzylpiperidin-4-yl)-3-(1-phenyl-1H-pyrazol-5-yl)pyridazin-4(1H)-one

The title compound was obtained in the same manner as in Example 22.

MS (ESI+), found: 412.1

Example 29

3-(1-phenyl-1H-pyrazol-5-yl)-1-piperidin-4-ylpyridazin-4(1H)-one

To a solution of 1-(1-benzylpiperidin-4-yl)-3-(1-phenyl-1H-pyrazol-5-yl)pyridazin-4(1H)-one (2.6 g) in methanol (30 mL) was added palladium hydroxide on carbon (10% wet, 0.30 g). The reaction mixture was stirred at 50° C. for 4 hr under a hydrogen atmosphere. The reaction mixture was filtered through celite, the filtrate was concentrated under reduced pressure, and the obtained crystals were recrystallized from methanol/ethyl acetate to give the title compound (0.75 g).

MS (ESI+), found: 322.1

Example 30

1-[1-(1-methylethyl)piperidin-4-yl]-3-(1-phenyl-1H-pyrazol-5-yl)pyridazin-4(1H)-one 3-(1-Phenyl-1H-pyrazol-5-yl)-1-piperidin-4-ylpyridazin-4(1H)-one (0.20 g), acetone (0.23 mL) and acetic acid (1.0 mL) were dissolved in THF (10 mL), sodium triacetoxyborohydride (0.66 g) was added, and the mixture was stirred at room temperature overnight. The reaction mixture was concentrated under reduced pressure, and neutralized with saturated sodium hydrogen carbonate. Sodium chloride was added to saturation, and the mixture was extracted with ethyl acetate/THF. The extract was dried over anhydrous magnesium sulfate and concentrated under reduced pressure. The residue was purified by silica gel column chromatography (NH, THF) and recrystallized from ethyl acetate/hexane to give the title compound (0.15 g).

MS (ESI+), found: 364.3

Example 31

1-(1-phenylpiperidin-4-yl)-3-(1-phenyl-1H-pyrazol-5-yl)pyridazin-4(1H)-one

A suspension of 3-(1-phenyl-1H-pyrazol-5-yl)-1-piperidin-4-ylpyridazin-4(1H)-one (0.14 g), iodobenzene (0.13 g), Pd$_2$(dba)$_3$ (10 mg), Xantphos (25 mg) and sodium tert-butoxide (63 mg) in 1,4-dioxane (5 mL) was stirred at 100° C. for 3 hr under an argon atmosphere. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, ethyl acetate/hexane) and recrystallized from ethyl acetate/hexane to give the title compound (33 mg).

MS (ESI+), found: 398.2

Example 32 tert-butyl 4-[4-oxo-3-(1-phenyl-1H-pyrazol-5-yl)pyridazin-1(4H)-yl]piperidine-1-carboxylate 3-(1-Phenyl-1H-pyrazol-5-yl)-1-piperidin-4-ylpyridazin-4(1H)-one (0.58 g) and di-tert-butyl dicarbonate (0.63 mL) were dissolved in THF (20 mL), the mixture was stirred at room temperature for 2 hr. The reaction mixture was concentrated under reduced pressure. The obtained residue was purified by silica gel column chromatography (ethyl acetate/hexane) and recrystallized from ethyl acetate/hexane to give the title compound (0.25 g).
MS (ESI+), found: 422.2

Example 33

1-(1-methylpiperidin-4-yl)-3-(1-phenyl-1H-pyrazol-5-yl)pyridazin-4(1H)-one

The title compound was obtained in the same manner as in Example 30.
MS (ESI+), found: 336.2

Example 34

1-[1-(4-fluorophenyl)piperidin-4-yl]-3-(1-phenyl-1H-pyrazol-5-yl)pyridazin-4(1H)-one A suspension of 3-(1-phenyl-1H-pyrazol-5-yl)-1-piperidin-4-ylpyridazin-4(1H)-one (0.30 g), 1-bromo-4-fluorobenzene (0.21 mL), $Pd_2(dba)_3$ (43 mg), X-phos (45 mg) and sodium tert-butoxide (135 mg) in toluene (10 mL) was stirred at 120° C. for 5 hr under an argon atmosphere. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane) and recrystallized from ethyl acetate/hexane to give the title compound (0.32 g).
MS (ESI+), found: 416.2

Example 35

5-methoxy-3-(1-phenyl-1H-pyrazol-5-yl)-1-piperidin-4-ylpyridazin-4(1H)-one

The title compound was obtained in the same manner as in Example 29.
MS (ESI+), found: 352.1

Example 36

3-(1-phenyl-1H-pyrazol-5-yl)-1-{1-[4-(trifluoromethoxy)phenyl]piperidin-4-yl}pyridazin-4(1H)-one The title compound was obtained in the same manner as in Example 34.
MS (ESI+), found: 482.2

Example 37

3-(1-phenyl-1H-pyrazol-5-yl)-1-{1-[4-(trifluoromethyl)phenyl]piperidin-4-yl}pyridazin-4(1H)-one The title compound was obtained in the same manner as in Example 34.
MS (ESI+), found: 466.1

Example 38

1-{1-[4-(pentafluoro-$\lambda^6$-sulfanyl)phenyl]piperidin-4-yl}-3-(1-phenyl-1H-pyrazol-5-yl)pyridazin-4(1H)-one The title compound was obtained in the same manner as in Example 34.
MS (ESI+), found: 524.1

Example 39

1-[1-(4-methoxybenzyl)-1,2,3,6-tetrahydropyridin-4-yl]-3-(1-phenyl-1H-pyrazol-5-yl)pyridazin-4(1H)-one The title compound was obtained in the same manner as in Example 25.
MS (ESI+), found: 440.2

Example 40

1-(1-acetylpiperidin-4-yl)-3-(1-phenyl-1H-pyrazol-5-yl)pyridazin-4(1H)-one 3-(1-Phenyl-1H-pyrazol-5-yl)-1-piperidin-4-ylpyridazin-4(1H)-one (0.30 g) and triethylamine (0.26 mL) were dissolved in THF (20 mL), acetylchloride (0.066 mL) was added, and the mixture was stirred at room temperature overnight. The reaction mixture was diluted with ethyl acetate, washed with saturated aqueous sodium hydrogen carbonate solution and saturated brine, dried over anhydrous magnesium sulfate, and concentrated under reduced pressure. The obtained residue was recrystallized from 2-propanol/diethylether to give the title compound (0.15 g).
MS (ESI+), found: 364.1

Example 41

1-[1-(4-fluorophenyl)piperidin-4-yl]-5-methoxy-3-(1-phenyl-1H-pyrazol-5-yl)pyridazin-4(1H)-one The title compound was obtained in the same manner as in Example 34.
MS (ESI+), found: 446.2

Example 42

1-(1-methyl-1,2,3,6-tetrahydropyridin-4-yl)-3-(1-phenyl-1H-pyrazol-5-yl)pyridazin-4(1H)-one The title compound was obtained in the same manner as in Example 25.
MS (ESI+), found: 334.1

Example 43

1-(1-acetylpiperidin-3-yl)-3-(1-phenyl-1H-pyrazol-5-yl)pyridazin-4(1H)-one

The title compound was obtained in the same manner as in Example 40.
MS (ESI+), found: 364.1

Example 44

1-[1-(phenylcarbonyl)piperidin-3-yl]-3-(1-phenyl-1H-pyrazol-5-yl)pyridazin-4(1H)-one The title compound was obtained in the same manner as in Example 40.
MS (ESI+), found: 426.2

Example 45

1-{1-[(4-fluorophenyl)carbonyl]piperidin-3-yl}-3-(1-phenyl-1H-pyrazol-5-yl)pyridazin-4(1H)-one The title compound was obtained in the same manner as in Example 40
MS (ESI+), found: 444.2

Example 46

1-(1-phenylpiperidin-3-yl)-3-(1-phenyl-1H-pyrazol-5-yl)pyridazin-4(1H)-one

The title compound was obtained in the same manner as in Example 34.
MS (ESI+), found: 398.2

Example 47

3-(1-phenyl-1H-pyrazol-5-yl)-1-(1,2,3,6-tetrahydropyridin-4-yl)pyridazin-4(1H)-one A suspension of 3-(1-phenyl-1H-pyrazol-5-yl)-1-(1-prop-2-en-1-yl-1,2,3,6-tetrahydropyridin-4-yl)pyridazin-4(1H)-one (0.10 g), tetrakis(triphenylphosphine)palladium(0) (50 mg), 1,3-dimethylbarbituric acid (0.13 g) and dichloromethane (5 mL) was heated under reflux for 2 hr under a nitrogen atmosphere, and the mixture was stirred at room temperature overnight. The reaction mixture was concentrated under reduced pressure, and the residue was purified by silica gel column chromatography (NH, methanol/ethyl acetate) and recrystallized from 2-propanol/ethyl acetate to give the title compound (32 mg).
MS (ESI+), found: 320.1

Example 48

3-(1-phenyl-1H-pyrazol-5-yl)-1-(1-pyridin-2-ylpiperidin-4-yl)pyridazin-4(1H)-one The title compound was obtained in the same manner as in Example 34.
MS (ESI+), found: 399.2

Example 49

1-[1-(phenylcarbonyl)piperidin-4-yl]-3-(1-phenyl-1H-pyrazol-5-yl)pyridazin-4(1H)-one The title compound was obtained in the same manner as in Example 40.
MS (ESI+), found: 425.9

Example 50

2-{4-[5-methoxy-4-oxo-3-(1-phenyl-1H-pyrazol-5-yl)pyridazin-1(4H)-yl]piperidin-1-yl}benzonitrile The title compound was obtained in the same manner as in Example 34.
MS (ESI+), found: 453.2

Example 51

5-methoxy-3-(1-phenyl-1H-pyrazol-5-yl)-1-(1,2,3,6-tetrahydropyridin-4-yl)pyridazin-4(1H)-one The title compound was obtained in the same manner as in Example 47.
MS (ESI+), found: 350.2

Example 52

1-[1-(2,3-difluorophenyl)piperidin-4-yl]-5-methoxy-3-(1-phenyl-1H-pyrazol-5-yl)pyridazin-4(1H)-one The title compound was obtained in the same manner as in Example 34.
MS (ESI+), found: 464.2

Example 53

5-methoxy-3-(1-phenyl-1H-pyrazol-5-yl)-1-[1-(1,3-thiazol-2-yl)piperidin-4-yl]pyridazin-4(1H)-one The title compound was obtained in the same manner as in Example 34.
MS (ESI+), found: 435.1

Example 54

4-[4-oxo-3-(1-phenyl-1H-pyrazol-5-yl)pyridazin-1(4H)-yl]-N-phenylpiperidine-1-carboxamide To a solution of 3-(1-phenyl-1H-pyrazol-5-yl)-1-piperidin-4-ylpyridazin-4(1H)-one (0.10 g) in THF (10 mL) was added phenyl isocyanate (0.041 mL), and the mixture was stirred at room temperature for 2 hr. The reaction mixture was concentrated under reduced pressure, and the obtained residue was recrystallized from 2-propanol/n-heptane to give the title compound (0.13 g).
MS (ESI+), found: 441.2

Example 55

1-[1-(3-chloropyridin-2-yl)piperidin-4-yl]-5-methoxy-3-(1-phenyl-1H-pyrazol-5-yl)pyridazin-4(1H)-one The title compound was obtained in the same manner as in Example 34.
MS (ESI+), found: 463.1

Example 56

2-{4-[5-methoxy-4-oxo-3-(1-phenyl-1H-pyrazol-5-yl)pyridazin-1(4H)-yl]piperidin-1-yl}pyridine-3-carbonitrile The title compound was obtained in the same manner as in Example 34.
MS (ESI+), found: 454.1

Example 57

1-(3'-chloro-3,6-dihydro-2H-1,2'-bipyridin-4-yl)-5-methoxy-3-(1-phenyl-1H-pyrazol-5-yl)pyridazin-4(1H)-one The title compound was obtained in the same manner as in Example 34.
MS (ESI+), found: 461.0

Example 58

5-methoxy-3-(1-phenyl-1H-pyrazol-5-yl)-1-(1,2,3,4-tetrahydronaphthalen-2-yl)pyridazin-4(1H)-one To a mixture of 5-methoxy-3-(1-phenyl-1H-pyrazol-5-yl)pyridazin-4-ol (0.10 g), 1,2,3,4-tetrahydronaphthalen-2-ol (0.17 g), triphenylphosphine (0.29 g) and toluene was added DIAD toluene solution (1.9M, 0.59 mL) at 50° C., and the mixture was stirred at 50° C. for 1 hr and at room temperature overnight. The solvent was evaporated under reduced pressure, and the obtained residue was purified by silica gel column chromatography (methanol/ethyl acetate) and recrystallized from ethyl acetate/n-heptane to give the title compound (27 mg).
MS (ESI+), found: 399.2

Example 59

1-(cyclopropylmethyl)-5-methoxy-3-(1-phenyl-1H-pyrazol-5-yl)pyridazin-4(1H)-one

A) 3-chloro-1-(cyclopropylmethyl)-5-methoxypyridazin-4(1H)-one

3-Chloro-5-methoxypyridazin-4-ol (0.20 g) was dissolved in DMF (3.1 mL), NaH (0.0595 g, 60%, in oil) and tetrabutylammoniumiodide (0.0916 g) were added at 0° C., and the mixture was stirred at the same temperature for 30 min. To the reaction mixture was added (bromomethyl)cyclopropane (0.138 mL) at 0° C., and the mixture was stirred at 0° C. for 2.5 hr, at room temperature for 1 day and at 40° C. for 20 hr. The reaction mixture was diluted with water, extracted with ethyl acetate, washed with saturated aqueous sodium hydrogen carbonate solution and saturated brine, dried over anhydrous sodium sulfate, filtered, concentrated, and purified by silica gel column chromatography (ethyl acetate/hexane→methanol/ethyl acetate) to give the title compound (0.136 g).
MS (ESI+): [M+H]$^+$ 215.3.

B) 1-(cyclopropylmethyl)-5-methoxy-3-(1-phenyl-1H-pyrazol-5-yl)pyridazin-4(1H)-one 3-Chloro-1-(cyclopropylmethyl)-5-methoxypyridazin-4(1H)-one (0.133 g), 1-phenyl-5-(4,4,5,5-tetramethyl-1,3,2-dioxaborolan-2-yl)-1H-pyrazole (0.200 g), potassium carbonate (0.171 g) and bis(di-tert-butyl(4-dimethylaminophenyl)phosphine)dichloropalladium(II) (0.0219 g) were suspended in toluene (3.09 mL) and water (0.309 mL), and the suspension was heated under reflux for 20 hr under an argon atmosphere. The reaction mixture was cooled to room temperature, diluted with water, saturated aqueous sodium hydrogen carbonate solution and saturated brine, extracted with ethyl acetate, dried over anhydrous sodium sulfate, filtered, concentrated, purified by NH silica gel column chromatography (ethyl acetate/hexane→methanol/ethyl acetate) and recrystallized from ethyl acetate/hexane to give the title compound (0.119 g).
MS (ESI+): [M+H]$^+$ 323.3.

Example 60

5-methoxy-3-(1-phenyl-1H-pyrazol-5-yl)-1-(phenylsulfonyl)pyridazin-4(1H)-one

A) 5-methoxy-3-(1-phenyl-1H-pyrazol-5-yl)pyridazin-4-ol

1-Benzyl-5-methoxy-3-(1-phenyl-1H-pyrazol-5-yl)pyridazin-4(1H)-one (15.0 g) and palladium hydroxide on carbon (5.88 g, palladium 20%, 50% water moistened product) were suspended in THF (500 mL) and methanol (300 mL), and the suspension was stirred at room temperature for 2 days under a hydrogen atmosphere. The reaction mixture was filtered through celite, and the filtrate was concentrated and solidified with ethanol/hexane to give the title compound (9.10 g).
MS (ESI+): [M+H]$^+$ 269.2.

B) 5-methoxy-3-(1-phenyl-1H-pyrazol-5-yl)-1-(phenylsulfonyl)pyridazin-4(1H)-one A solution of 5-methoxy-3-(1-phenyl-1H-pyrazol-5-yl)pyridazin-4-ol (100 mg) and benzenesulfonylchloride (79 mg) in pyridine (4.00 mL) was stirred at room temperature overnight. The reaction mixture was diluted with ethyl acetate, washed with water, dried over anhydrous sodium sulfate, filtered and concentrated. The resulting solid was washed with ethyl acetate and diethyl ether, and dried to give the title compound (120 mg).
MS (ESI+): [M+H]$^+$ 409.0.

Example 61

1-(biphenyl-3-ylmethyl)-5-methoxy-3-(1-phenyl-1H-pyrazol-5-yl)pyridazin-4(1H)-one 5-Methoxy-3-(1-phenyl-1H-pyrazol-5-yl)pyridazin-4-ol (0.0478 g) was dissolved in DMF (3.6 mL), NaH (0.0078 g, 60%, in oil) and tetrabutylammoniumiodide (0.0131 g) were added at 0° C., and the mixture was stirred at the same temperature for 20 min. To the reaction mixture was added 3-(bromomethyl)biphenyl (0.0462 g) at 0° C., and the mixture was stirred at room temperature for 2.5 days. The reaction mixture was diluted with water, extracted with ethyl acetate, washed with brine, dried over anhydrous sodium sulfate, filtered, concentrated, and purified by silica gel column chromatography (ethyl acetate/hexane→methanol/ethyl acetate) to give the title compound (0.0385 g).
MS (ESI+): [M+H]$^+$ 435.2.

Example 62

1-(biphenyl-4-ylmethyl)-5-methoxy-3-(1-phenyl-1H-pyrazol-5-yl)pyridazin-4(1H)-one The title compound (0.0490 g) was obtained from 5-methoxy-3-(1-phenyl-1H-pyrazol-5-yl)pyridazin-4-ol (0.0500 g) and 4-(bromomethyl)biphenyl (0.0482 g) in the same manner as in Example 61.
MS (ESI+): [M+H]$^+$ 435.2.

Example 63

1-(biphenyl-2-ylmethyl)-5-methoxy-3-(1-phenyl-1H-pyrazol-5-yl)pyridazin-4(1H)-one The title compound (0.0399 g) was obtained from 5-methoxy-3-(1-phenyl-1H-pyrazol-5-yl)pyridazin-4-ol (0.0500 g) and 2-(bromomethyl)biphenyl (0.0356 mL) in the same manner as in Example 61.

MS (ESI+): [M+H]$^+$ 435.4.

Example 64

3-(1-phenyl-1H-pyrazol-5-yl)-1-{1-[2-(trifluoromethyl)phenyl]piperidin-4-yl}pyridazin-4(1H)-one A mixture of 3-(1-phenyl-1H-pyrazol-5-yl)-1-piperidin-4-ylpyridazin-4(1H)-one (25.7 mg), 2-bromobenzotrifluoride (27 mg), Pd$_2$(dba)$_3$ (1.8 mg), sodium tert-butoxide (8.8 mg), X-phos (1.9 mg) and toluene (1.0 mL) was heated using a microwave reactor (Synthos3000) at 120° C. for 10 min. To the reaction mixture was added 5% sodium hydrogen carbonate solution, and the mixture was extracted with ethyl acetate (the extract was separated by an organic layer-separation filter). The extract was distilled by blowing air at 60° C., and the residue was dissolved in DMSO. The solution was purified by preparative HPLC (column: Hydrosphere, solvent: 10 mM NH$_4$HCO$_3$/MeCN). The obtained eluate containing the title compound was concentrated by blowing air at 60° C. to give the title compound (4.2 mg).

MS (ESI+): [M+H]$^+$ 465.2

The structures and the like of the compounds of Examples 1-64 are shown in the following Tables.

TABLE 1-1

| Ex. No. | IUPAC name | structure | salt | MS |
|---|---|---|---|---|
| 1 | 3-(1-phenyl-1H-pyrazol-5-yl)-1-[3-(trifluoromethyl)phenyl]furo[3,2-c]pyridazin-4(1H)-one | 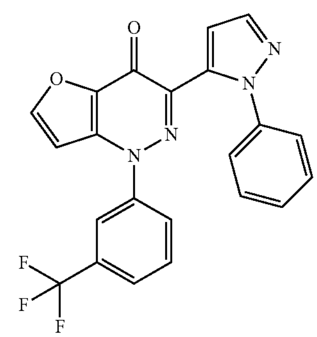 [SMILES: O=c1c(-c2ccnn2-c2ccccc2)nn(-c2cccc(C(F)(F)F)c2)c2ccoc12] | — | |

$^1$H NMR (300 MHz, CDCl$_3$) δ 6.71 (1H, d, J = 2.3 Hz), 7.13 (1H, dd, J = 8.3, 1.9 Hz), 7.21 (1H, s), 7.35-7.45 (6H, m), 7.51 (1H, t, J = 7.9 Hz), 7.64 (1H, d, J = 7.9 Hz), 7.82 (1H, d, J = 1.9 Hz), 7.86 (1H, d, J = 2.3 Hz).

| 2 | 3-(1-phenyl-1H-pyrazol-5-yl)-1-[3-(trifluoromethyl)phenyl]-6,7-dihydrofuro[3,2-c]pyridazin-4(1H)-one | | — | |

$^1$H NMR (300 MHz, CDCl$_3$) δ 3.42 (2H, t, J = 9.0 Hz), 4.72 (2H, t, J = 9.0 Hz), 7.00 (1H, dd, J = 7.9, 1.9 Hz), 7.10 (1H, s), 7.30 (1H, d, J = 1.9 Hz), 7.34-7.49 (6H, m), 7.63 (1H, t, J = 7.9 Hz), 7.88 (1H, d, J = 7.9 Hz).

TABLE 1-1-continued

| Ex. No. | IUPAC name | structure | salt | MS |
|---|---|---|---|---|
| 3 | 1-[2-fluoro-4-(1H-pyrazol-1-yl)phenyl]-3-(1-phenyl-1H-pyrazol-5-yl)furo[3,2-c]pyridazin-4(1H)-one | 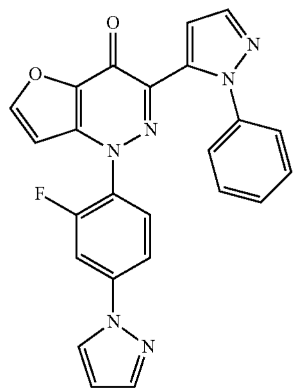 [SMILES: O=c1c(-c2ccnn2-c2ccccc2)nn(-c2ccc(-n3cccn3)cc2F)c2ccoc12] | — | 439.3 |

TABLE 1-2

| Ex. No. | IUPAC name | structure | salt | MS |
|---|---|---|---|---|
| 4 | 1-[2-fluoro-4-(1H-pyrazol-1-yl)phenyl]-3-(1-phenyl-1H-pyrazol-5-yl)-6,7-dihydrofuro[3,2-c]pyridazin-4(1H)-one | 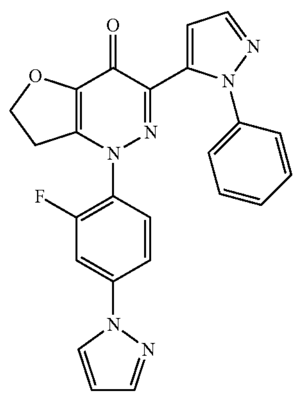 [SMILES: O=c1c(-c2ccnn2-c2ccccc2)nn(-c2ccc(-n3cccn3)cc2F)c2c1OCC2] | — | 441.2 |
| 5 | 3-(1-phenyl-1H-pyrazol-5-yl)-1-[4-(1H-pyrazol-1-yl)-2-(2,2,2-trifluoroethoxy)phenyl]furo[3,2-c]pyridazin-4(1H)-one | 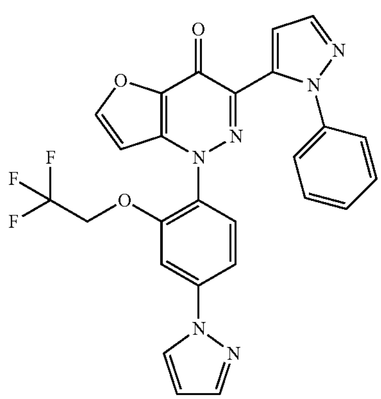 [SMILES: O=c1c(-c2ccnn2-c2ccccc2)nn(-c2ccc(-n3cccn3)cc2OCC(F)(F)F)c2ccoc12] | — | 519.1 |

TABLE 1-2-continued
| Ex. No. | IUPAC name | structure | salt | MS |
|---|---|---|---|---|
| 6 | 3-(1-phenyl-1H-pyrazol-5-yl)-1-[4-(1H-pyrazol-1-yl)-2-(2,2,2-trifluoroethoxy)phenyl]-6,7-dihydrofuro[3,2-c]pyridazin-4(1H)-one | 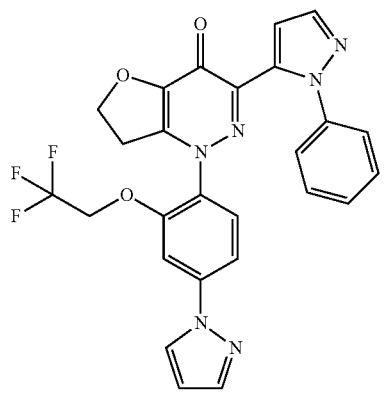 [SMILES: O=c1c(-c2ccnn2-c2ccccc2)nn(-c2ccc(-n3cccn3)cc2OCC(F)(F)F)c2c1OCC2] | — | 521.3 |
| 7 | 1-(4-iodophenyl)-3-(1-phenyl-1H-pyrazol-5-yl)furo[3,2-c]pyridazin-4(1H)-one | 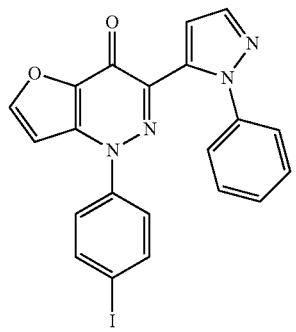 [SMILES: O=c1c(-c2ccnn2-c2ccccc2)nn(-c2ccc(I)cc2)c2ccoc12] | — | 480.8 |
| 8 | 3-(1-phenyl-1H-pyrazol-5-yl)-1-[4-(1H-pyrazol-1-yl)phenyl]-6,7-dihydrofuro[3,2-c]pyridazin-4(1H)-one | 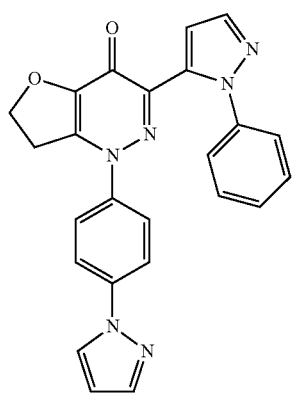 [SMILES: O=c1c(-c2ccnn2-c2ccccc2)nn(-c2ccc(-n3cccn3)cc2)c2c1OCC2] | — | 423.4 |

TABLE 1-3

| Ex. No. | IUPAC name | structure | salt | MS |
|---|---|---|---|---|
| 9 | 1-[4-iodo-3-(trifluoromethoxy)phenyl]-3-(1-phenyl-1H-pyrazol-5-yl)furo[3,2-c]pyridazin-4(1H)-one | 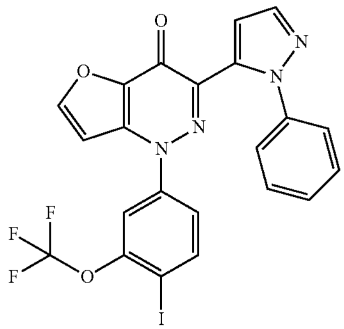 [SMILES: O=c1c(-c2ccnn2-c2ccccc2)nn(-c2ccc(I)c(OC(F)(F)F)c2)c2ccoc12] | — | 565.1 |
| 10 | 3-(1-phenyl-1H-pyrazol-5-yl)-1-[3-(trifluoromethoxy)phenyl]furo[3,2-c]pyridazin-4(1H)-one | 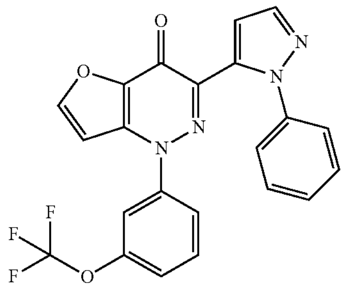 [SMILES: O=c1c(-c2ccnn2-c2ccccc2)nn(-c2cccc(OC(F)(F)F)c2)c2ccoc12] | — | 439.3 |
| 11 | 2-(1-phenyl-1H-pyrazol-5-yl)pyridazino[6,1-c][1,4]benzoxazin-3(5H)-one | 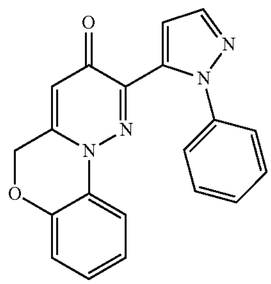 [SMILES: O=c1cc2n(nc1-c1ccnn1-c1ccccc1)-c1ccccc1OC2] | — | 343.1 |
| 12 | 3-methoxy-6-phenyl-2-(1-phenyl-1H-pyrazol-5-yl)-4H-pyran-4-one | 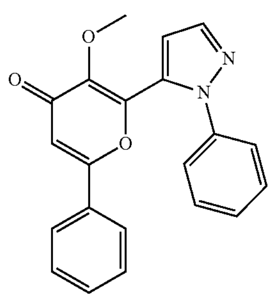 [SMILES: COc1c(-c2ccnn2-c2ccccc2)oc(-c2ccccc2)cc1=O] | — | 345.3 |
| 13 | 5-phenyl-3-(1-phenyl-1H-pyrazol-5-yl)pyrazin-2(1H)-one | 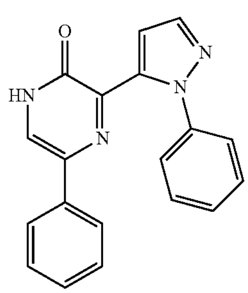 [SMILES: O=c1[nH]cc(-c2ccccc2)nc1-c1ccnn1-c1ccccc1] | — | 315.3 |

TABLE 1-4

| Ex. No. | IUPAC name | structure | salt | MS |
|---|---|---|---|---|
| 14 | 3-hydroxy-6-phenyl-2-(1-phenyl-1H-pyrazol-5-yl)-4H-pyran-4-one | 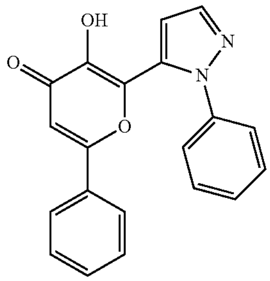 [SMILES: O=c1cc(-c2ccccc2)oc(-c2ccnn2-c2ccccc2)c1O] | — | 331.3 |
| 15 | 6-phenyl-4-(1-phenyl-1H-pyrazol-5-yl)-pyridazin-3(2H)-one | 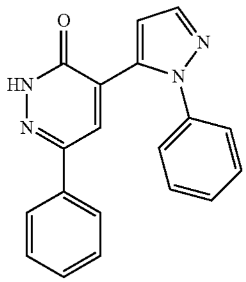 [SMILES: O=c1[nH]nc(-c2ccccc2)cc1-c1ccnn1-c1ccccc1] | — | 315.3 |
| 16 | 5-phenyl-3-(1-phenyl-1H-pyrazol-5-yl)-pyridin-2(1H)-one | 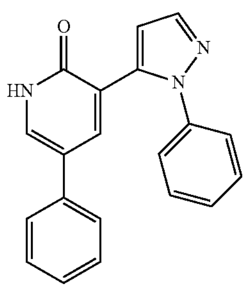 [SMILES: O=c1[nH]cc(-c2ccccc2)cc1-c1ccnn1-c1ccccc1] | — | 314.3 |
| 17 | 2-phenyl-6-(1-phenyl-1H-pyrazol-5-yl)-pyrimidin-4(3H)-one | 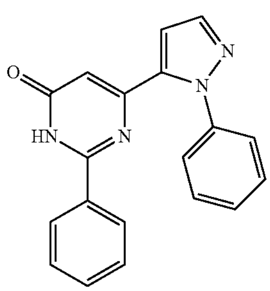 [SMILES: O=c1cc(-c2ccnn2-c2ccccc2)nc(-c2ccccc2)[nH]1] | — | 315.1 |
| 18 | 3-(1-phenyl-1H-pyrazol-5-yl)-1-[3-(trifluoromethyl)-phenyl]pyridin-4(1H)-one | 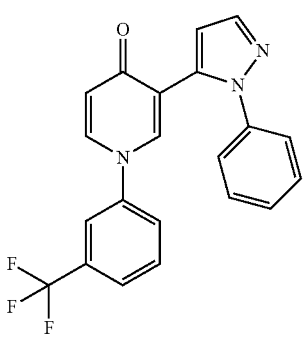 [SMILES: O=c1ccn(-c2cccc(C(F)(F)F)c2)cc1-c1ccnn1-c1ccccc1] | — | 382.3 |

TABLE 1-5

| Ex. No. | IUPAC name | structure | salt | MS |
|---|---|---|---|---|
| 19 | 5-(1-phenyl-1H-pyrazol-5-yl)-1-[3-(trifluoromethyl)-phenyl]pyridazin-4(1H)-one | 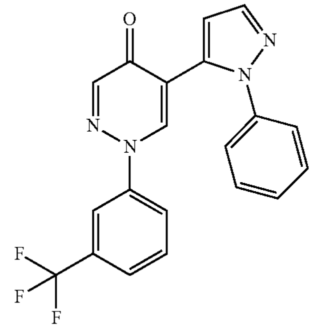 [SMILES: O=c1cnn(-c2cccc(C(F)(F)F)c2)cc1-c1ccnn1-c1ccccc1] | — | 383.3 |
| 20 | 5-(2-fluorophenyl)-1-(1-phenyl-1H-pyrazol-5-yl)pyridin-2(1H)-one | 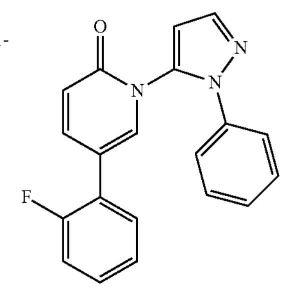 | — | 332.2 |
| 21 | 2-(1-phenyl-1H-pyrazol-5-yl)-6-[3-(trifluoromethyl)-phenyl]pyridazin-3(2H)-one | 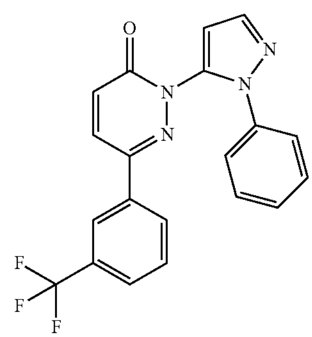 [SMILES: O=c1ccc(-c2cccc(C(F)(F)F)c2)nn1-c1ccnn1-c1ccccc1] | — | — |

$^1$H NMR (300 MHz, CDCl$_3$) δ 6.70 (1H, d, J = 1.9 Hz), 7.09 (1H, d, J = 10.2 Hz), 7.28-7.42 (5H, m), 7.51-7.56 (1H, m), 7.66-7.73 (4H, m), 7.82 (1H, d, J = 2.3 Hz).

| 22 | 1-(1-benzyl-piperidin-3-yl)-3-(1-phenyl-1H-pyrazol-5-yl)pyridazin-4(1H)-one | | — | 412.3 |

TABLE 1-6

| Ex. No. | IUPAC name | structure | salt | MS |
|---|---|---|---|---|
| 23 | 1-benzyl-5-methoxy-3-(1-phenyl-1H-pyrazol-5-yl)-pyridazin-4(1H)-one | | — | — |

¹H NMR (400 MHz, DMSO-d₆) δ 3.81 (3H, s), 5.10 (2H, s), 6.95 (1H, d, J = 1.6 Hz), 7.05-7.07 (2H, m), 7.24-7.38 (8H, m), 7.74 (1H, d, J = 1.6 Hz), 8.33 (1H, s).

| Ex. No. | IUPAC name | structure | salt | MS |
|---|---|---|---|---|
| 24 | 3-(1-phenyl-1H-pyrazol-5-yl)-1-piperidin-3-yl-pyridazin-4(1H)-one | 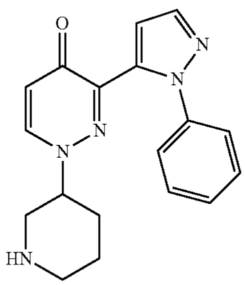 [SMILES: O=c1ccn(C2CCCNC2)nc1-c1ccnn1-c1ccccc1] | HCl | 322.2 |
| 25 | 1-(1-benzyl-1,2,3,6-tetrahydropyridin-4-yl)-5-methoxy-3-(1-phenyl-1H-pyrazol-5-yl)-pyridazin-4(1H)-one | 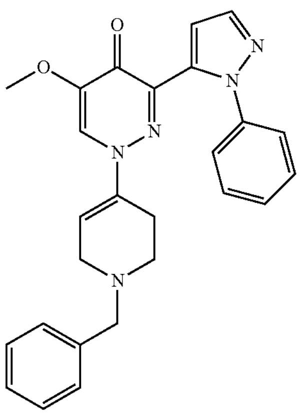 [SMILES: COc1cn(C2=CCN(Cc3ccccc3)CC2)nc(-c2ccnn2-c2ccccc2)c1=O] | — | 440.2 |
| 26 | 3-(1-phenyl-1H-pyrazol-5-yl)-1-(1-prop-2-en-1-yl-1,2,3,6-tetrahydropyridin-4-yl)-pyridazin-4(1H)-one | 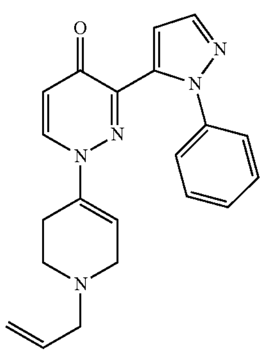 [SMILES: C=CCN1CC=C(n2ccc(=O)c(-c3ccnn3-c3ccccc3)n2)CC1] | — | 360.2 |

TABLE 1-7

| Ex. No. | IUPAC name | structure | salt | MS |
|---|---|---|---|---|
| 27 | 5-methoxy-3-(1-phenyl-1H-pyrazol-5-yl)-1-(1-prop-2-en-1-yl-1,2,3,6-tetrahydropyridin-4-yl)pyridazin-4(1H)-one | 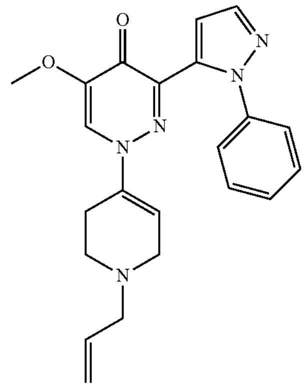 [SMILES: C=CCN1CC=C(n2cc(OC)c(=O)c(-c3ccnn3-c3ccccc3)n2)CC1] | — | 390.2 |
| 28 | 1-(1-benzyl-piperidin-4-yl)-3-(1-phenyl-1H-pyrazol-5-yl)-pyridazin-4(1H)-one | 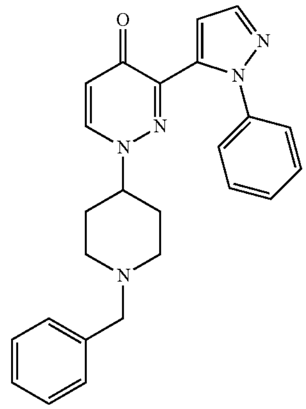 [SMILES: O=c1ccn(C2CCN(Cc3ccccc3)CC2)nc1-c1ccnn1-c1ccccc1] | — | 412.1 |
| 29 | 3-(1-phenyl-1H-pyrazol-5-yl)-1-piperidin-4-ylpyridazin-4(1H)-one | 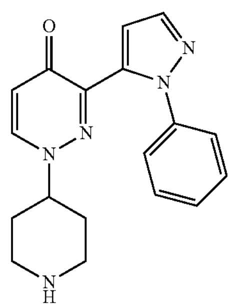 [SMILES: O=c1ccn(C2CCNCC2)nc1-c1ccnn1-c1ccccc1] | — | 322.1 |
| 30 | 1-[1-(1-methyl-ethyl)-piperidin-4-yl]-3-(1-phenyl-1H-pyrazol-5-yl)pyridazin-4(1H)-one | 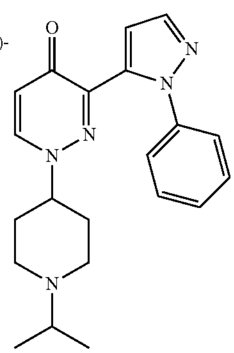 | — | 364.3 |

TABLE 1-7-continued

| Ex. No. | IUPAC name | structure | salt | MS |
|---|---|---|---|---|
| 31 | 1-(1-phenyl-piperidin-4-yl)-3-(1-phenyl-1H-pyrazol-5-yl)-pyridazin-4(1H)-one | 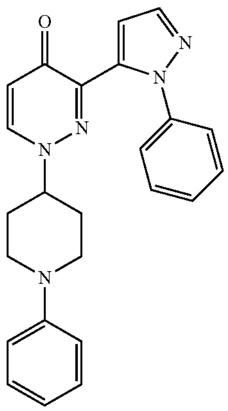 [SMILES: O=c1ccn(C2CCN(c3ccccc3)CC2)nc1-c1ccnn1-c1ccccc1] | — | 398.2 |

TABLE 1-8

| Ex. No. | IUPAC name | structure | salt | MS |
|---|---|---|---|---|
| 32 | tert-butyl 4-[4-oxo-3-(1-phenyl-1H-pyrazol-5-yl)pyridazin-1(4H)-yl]-piperidine-1-carboxylate | 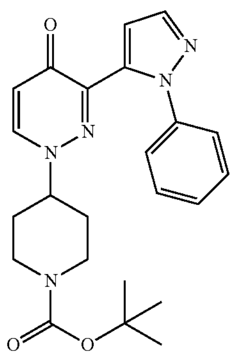 [SMILES: CC(C)(C)OC(=O)N1CCC(n2ccc(=O)c(-c3ccnn3-c3ccccc3)n2)CC1] | — | 422.2 |
| 33 | 1-(1-methyl-piperidin-4-yl)-3-(1-phenyl-1H-pyrazol-5-yl)-pyridazin-4(1H)-one | 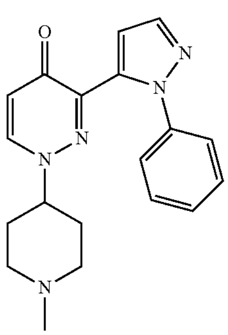 [SMILES: CN1CCC(n2ccc(=O)c(-c3ccnn3-c3ccccc3)n2)CC1] | — | 336.2 |

TABLE 1-8-continued

| Ex. No. | IUPAC name | structure | salt | MS |
|---|---|---|---|---|
| 34 | 1-[1-(4-fluoro-phenyl)-piperidin-4-yl]-3-(1-phenyl-1H-pyrazol-5-yl)pyridazin-4(1H)-one | 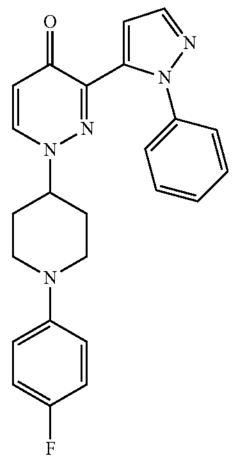 [SMILES: O=c1ccn(C2CCN(c3ccc(F)cc3)CC2)nc1-c1ccnn1-c1ccccc1] | — | 416.2 |
| 35 | 5-methoxy-3-(1-phenyl-1H-pyrazol-5-yl)-1-piperidin-4-ylpyridazin-4(1H)-one | 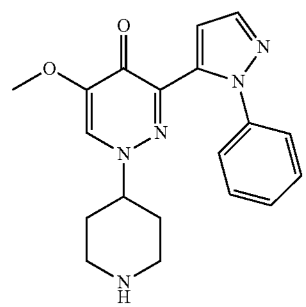 [SMILES: COc1cn(C2CCNCC2)nc(-c2ccnn2-c2ccccc2)c1=O] | — | 352.1 |
| 36 | 3-(1-phenyl-1H-pyrazol-5-yl)-1-{1-[4-(trifluoro-methoxy)-phenyl]piperidin-4-yl}-pyridazin-4(1H)-one | 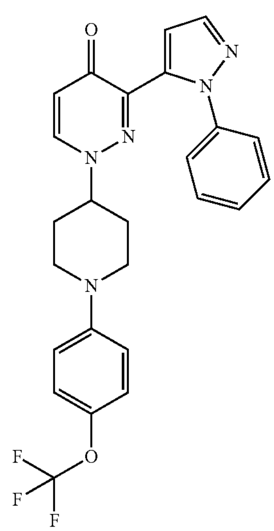 [SMILES: O=c1ccn(C2CCN(c3ccc(OC(F)(F)F)cc3)CC2)nc1-c1ccnn1-c1ccccc1] | — | 482.2 |

TABLE 1-9

| Ex. No. | IUPAC name | structure | salt | MS |
|---|---|---|---|---|
| 37 | 3-(1-phenyl-1H-pyrazol-5-yl)-1-{1-[4-(trifluoromethyl)phenyl]piperidin-4-yl}pyridazin-4(1H)-one | 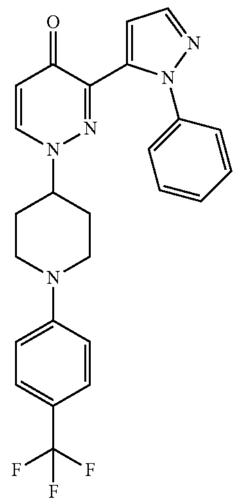 [SMILES: O=c1ccn(C2CCN(c3ccc(C(F)(F)F)cc3)CC2)nc1-c1ccnn1-c1ccccc1] | — | 466.1 |
| 38 | 1-{1-[4-(pentafluoro-λ⁶-sulfanyl)phenyl]piperidin-4-yl}-3-(1-phenyl-1H-pyrazol-5-yl)pyridazin-4(1H)-one | 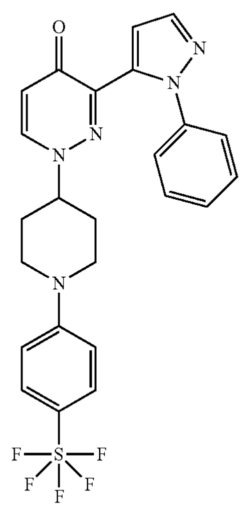 [SMILES: O=c1ccn(C2CCN(c3ccc(S(F)(F)(F)(F)F)cc3)CC2)nc1-c1ccnn1-c1ccccc1] | — | 524.1 |
| 39 | 1-[1-(4-methoxybenzyl)-1,2,3,6-tetrahydropyridin-4-yl]-3-(1-phenyl-1H-pyrazol-5-yl)pyridazin-4(1H)-one | 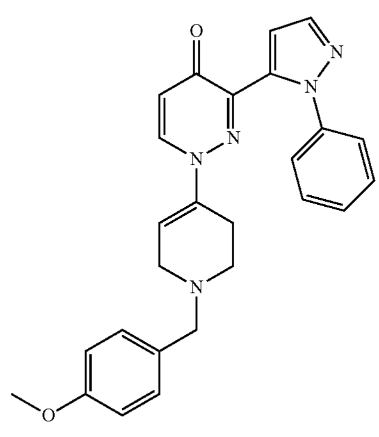 [SMILES: COc1ccc(CN2CC=C(n3ccc(=O)c(-c4ccnn4-c4ccccc4)n3)CC2)cc1] | — | 440.2 |

TABLE 1-9-continued

| Ex. No. | IUPAC name | structure | salt | MS |
|---|---|---|---|---|
| 40 | 1-(1-acetylpiperidin-4-yl)-3-(1-phenyl-1H-pyrazol-5-yl)pyridazin-4(1H)-one | 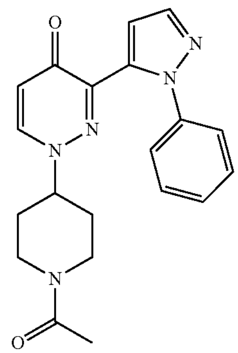 [SMILES: CC(=O)N1CCC(n2ccc(=O)c(-c3ccnn3-c3ccccc3)n2)CC1] | — | 364.1 |
| 41 | 1-[1-(4-fluorophenyl)piperidin-4-yl]-5-methoxy-3-(1-phenyl-1H-pyrazol-5-yl)pyridazin-4(1H)-one | 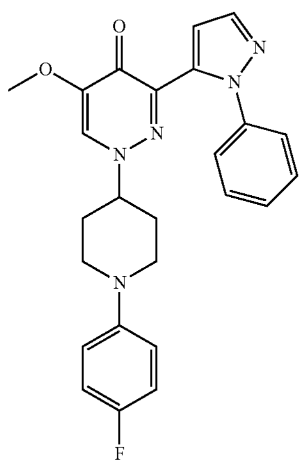 [SMILES: COc1cn(C2CCN(c3ccc(F)cc3)CC2)nc(-c2ccnn2-c2ccccc2)c1=O] | — | 446.2 |

TABLE 1-10

| Ex. No. | IUPAC name | structure | salt | MS |
|---|---|---|---|---|
| 42 | 1-(1-methyl-1,2,3,6-tetrahydropyridin-4-yl)-3-(1-phenyl-1H-pyrazol-5-yl)pyridazin-4(1H)-one | 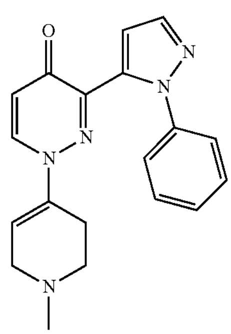 [SMILES: CN1CC=C(n2ccc(=O)c(-c3ccnn3-c3ccccc3)n2)CC1] | — | 334.1 |

TABLE 1-10-continued

| Ex. No. | IUPAC name | structure | salt | MS |
|---|---|---|---|---|
| 43 | 1-(1-acetylpiperidin-3-yl)-3-(1-phenyl-1H-pyrazol-5-yl)pyridazin-4(1H)-one | 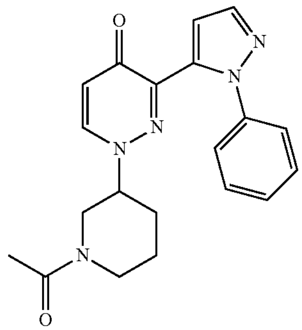 [SMILES: CC(=O)N1CCCC(n2ccc(=O)c(-c3ccnn3-c3ccccc3)n2)C1] | — | 364.1 |
| 44 | 1-[1-(phenylcarbonyl)piperidin-3-yl]-3-(1-phenyl-1H-pyrazol-5-yl)pyridazin-4(1H)-one | 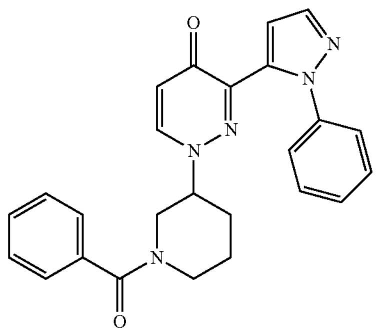 [SMILES: O=C(c1ccccc1)N1CCCC(n2ccc(=O)c(-c3ccnn3-c3ccccc3)n2)C1] | — | 426.2 |
| 45 | 1-{1-[(4-fluorophenyl)carbonyl]piperidin-3-yl}-3-(1-phenyl-1H-pyrazol-5-yl)pyridazin-4(1H)-one | 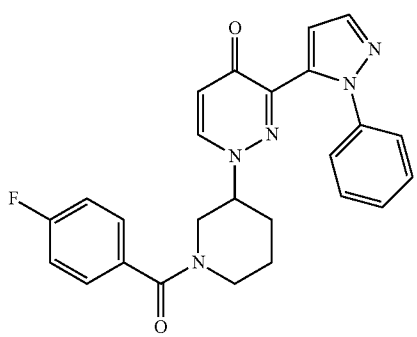 [SMILES: O=C(c1ccc(F)cc1)N1CCCC(n2ccc(=O)c(-c3ccnn3-c3ccccc3)n2)C1] | — | 444.2 |
| 46 | 1-(1-phenylpiperidin-3-yl)-3-(1-phenyl-1H-pyrazol-5-yl)pyridazin-4(1H)-one | 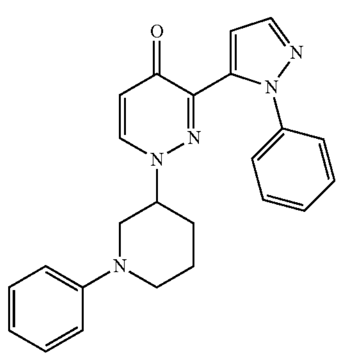 [SMILES: O=c1ccn(C2CCCN(c3ccccc3)C2)nc1-c1ccnn1-c1ccccc1] | — | 398.2 |

TABLE 1-11

| Ex. No. | IUPAC name | structure | salt | MS |
|---|---|---|---|---|
| 47 | 3-(1-phenyl-1H-pyrazol-5-yl)-1-(1,2,3,6-tetrahydro-pyridin-4-yl)pyridazin-4(1H)-one | 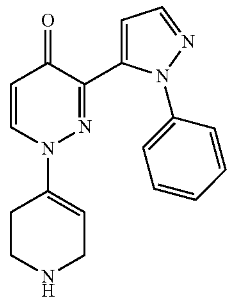 [SMILES: O=c1ccn(C2=CCNCC2)nc1-c1ccnn1-c1ccccc1] | — | 320.1 |
| 48 | 3-(1-phenyl-1H-pyrazol-5-yl)-1-(1-pyridin-2-ylpiperidin-4-yl)-pyridazin-4(1H)-one | 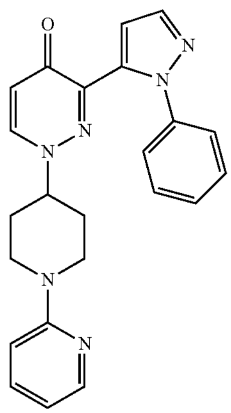 [SMILES: O=c1ccn(C2CCN(c3ccccn3)CC2)nc1-c1ccnn1-c1ccccc1] | — | 399.2 |
| 49 | 1-[1-(phenyl-carbonyl)-piperidin-4-yl]-3-(1-phenyl-1H-pyrazol-5-yl)pyridazin-4(1H)-one | 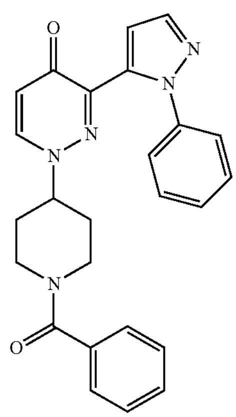 [SMILES: O=C(c1ccccc1)N1CCC(n2ccc(=O)c(-c3ccnn3-c3ccccc3)n2)CC1] | — | 425.9 |
| 50 | 2-{4-[5-methoxy-4-oxo-3-(1-phenyl-1H-pyrazol-5-yl)pyridazin-1(4H)-yl]-piperidin-1-yl}benzo-nitrile | 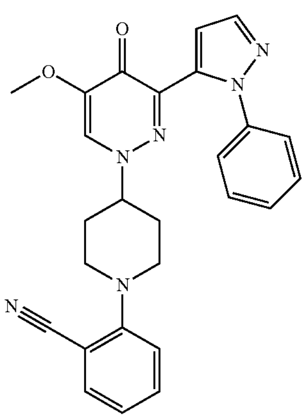 [SMILES: COc1cn(C2CCN(c3ccccc3C#N)CC2)nc(-c2ccnn2-c2ccccc2)c1=O] | — | 453.2 |

TABLE 1-11-continued

| Ex. No. | IUPAC name | structure | salt | MS |
|---|---|---|---|---|
| 51 | 5-methoxy-3-(1-phenyl-1H-pyrazol-5-yl)-1-(1,2,3,6-tetrahydro-pyridin-4-yl)pyridazin-4(1H)-one | 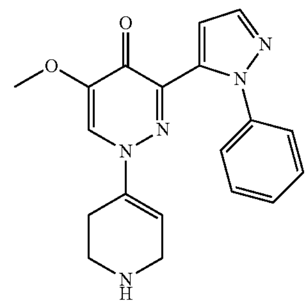 [SMILES: COc1cn(C2=CCNCC2)nc(-c2ccnn2-c2ccccc2)c1=O] | — | 350.2 |

TABLE 1-12

| Ex. No. | IUPAC name | structure | salt | MS |
|---|---|---|---|---|
| 52 | 1-[1-(2,3-difluoro-phenyl)-piperidin-4-yl]-5-methoxy-3-(1-phenyl-1H-pyrazol-5-yl)-pyridazin-4(1H)-one | 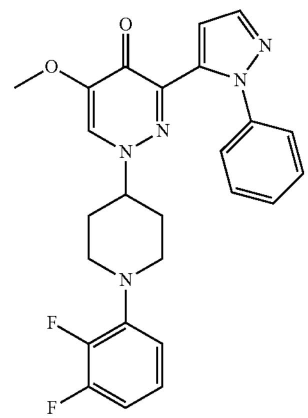 [SMILES: COc1cn(C2CCN(c3cccc(F)c3F)CC2)nc(-c2ccnn2-c2ccccc2)c1=O] | — | 464.2 |
| 53 | 5-methoxy-3-(1-phenyl-1H-pyrazol-5-yl)-1-[1-(1,3-thiazol-2-yl)-piperidin-4-yl]-pyridazin-4(1H)-one | 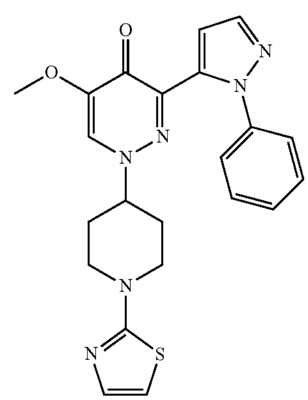 [SMILES: COc1cn(C2CCN(c3nccs3)CC2)nc(-c2ccnn2-c2ccccc2)c1=O] | — | 435.1 |

TABLE 1-12-continued

| Ex. No. | IUPAC name | structure | salt | MS |
|---|---|---|---|---|
| 54 | 4-[4-oxo-3-(1-phenyl-1H-pyrazol-5-yl)-pyridazin-1(4H)-yl]-N-phenyl-piperidine-1-carboxamide | 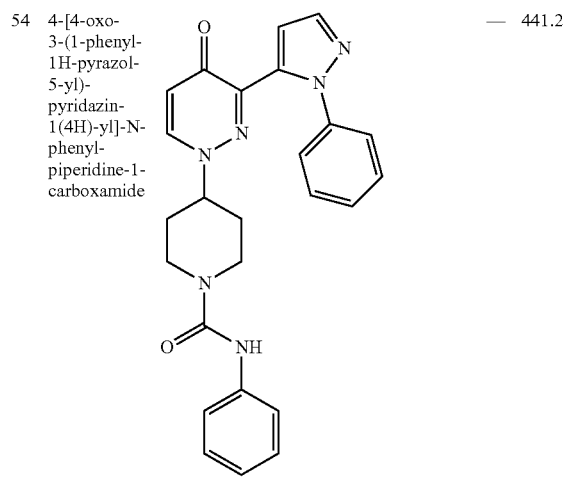 | — | 441.2 |
| 55 | 1-[1-(3-chloro-pyridin-2-yl)piperidin-4-yl]-5-methoxy-3-(1-phenyl-1H-pyrazol-5-yl)-pyridazin-4(1H)-one | 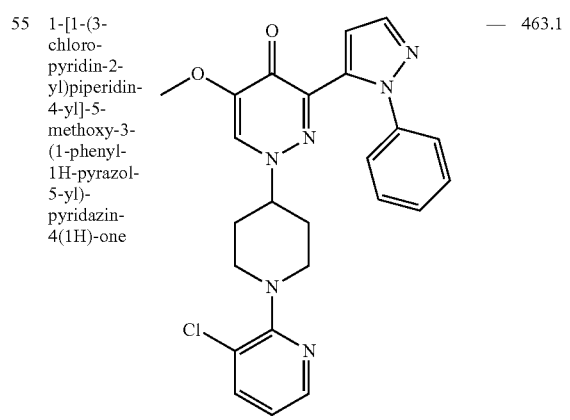 | — | 463.1 |
| 56 | 2-{4-[5-methoxy-4-oxo-3-(1-phenyl-1H-pyrazol-5-yl)-pyridazin-1(4H)-yl]-piperidin-1-yl}pyridine-3-carbonitrile | 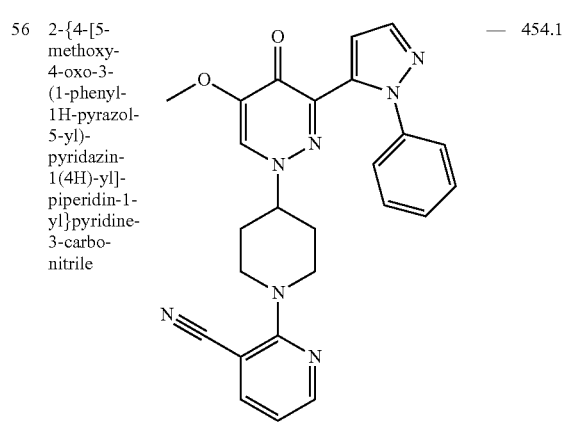 | — | 454.1 |

TABLE 1-13

| Ex. No. | IUPAC name | structure | salt | MS |
|---|---|---|---|---|
| 57 | 1-(3'-chloro-3,6-dihydro-2H-1,2'-bipyridin-4-yl)-5-methoxy-3-(1-phenyl-1H-pyrazol-5-yl)-pyridazin-4(1H)-one | 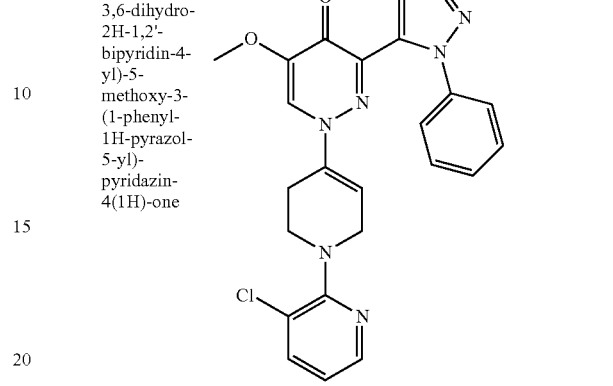 | — | 461.0 |
| 58 | 5-methoxy-3-(1-phenyl-1H-pyrazol-5-yl)-1-(1,2,3,4-tetrahydro-naphthalen-2-yl)-pyridazin-4(1H)-one | 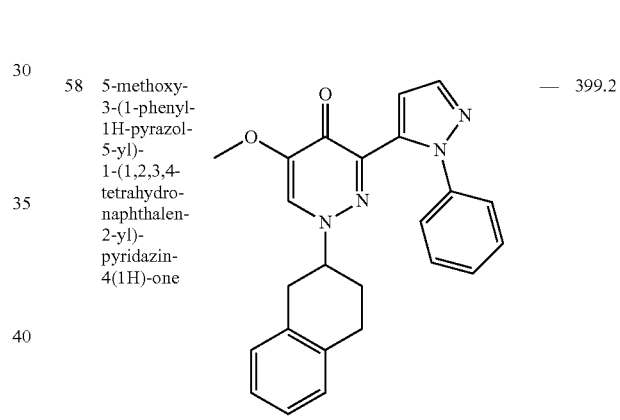 | — | 399.2 |
| 59 | 1-(cyclopropylmethyl)-5-methoxy-3-(1-phenyl-1H-pyrazol-5-yl)-pyridazin-4(1H)-one | 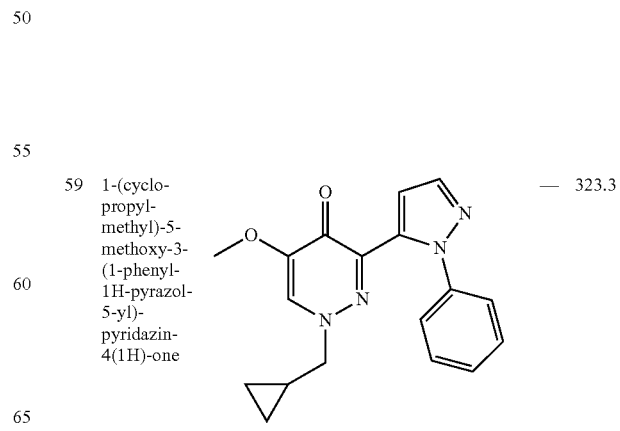 | — | 323.3 |

TABLE 1-13-continued

| Ex. No. | IUPAC name | structure | salt | MS |
|---|---|---|---|---|
| 60 | 5-methoxy-3-(1-phenyl-1H-pyrazol-5-yl)-1-(phenyl-sulfonyl)-pyridazin-4(1H)-one | 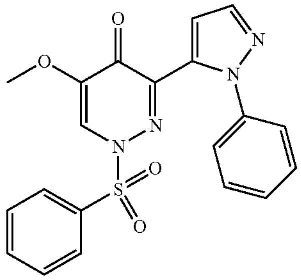 [SMILES: COc1cn(S(=O)(=O)c2ccccc2)nc(-c2ccnn2-c2ccccc2)c1=O] | — | 409.0 |
| 61 | 1-(biphenyl-3-ylmethyl)-5-methoxy-3-(1-phenyl-1H-pyrazol-5-yl)-pyridazin-4(1H)-one | | — | 435.2 |

TABLE 1-14

| Ex. No. | IUPAC name | structure | salt | MS |
|---|---|---|---|---|
| 62 | 1-(biphenyl-4-ylmethyl)-5-methoxy-3-(1-phenyl-1H-pyrazol-5-yl)pyridazin-4(1H)-one | 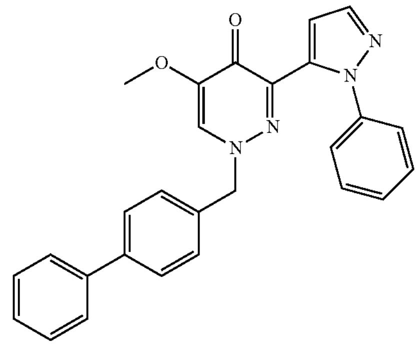 [SMILES: COc1cn(Cc2ccc(-c3ccccc3)cc2)nc(-c2ccnn2-c2ccccc2)c1=O] | — | 435.2 |
| 63 | 1-(biphenyl-2-ylmethyl)-5-methoxy-3-(1-phenyl-1H-pyrazol-5-yl)pyridazin-4(1H)-one | 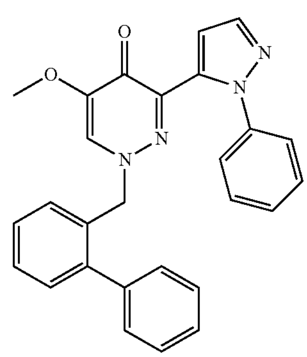 [SMILES: COc1cn(Cc2ccccc2-c2ccccc2)nc(-c2ccnn2-c2ccccc2)c1=O] | — | 435.4 |

TABLE 1-14-continued

| Ex. No. | IUPAC name | structure | salt | MS |
|---|---|---|---|---|
| 64 | 3-(1-phenyl-1H-pyrazol-5-yl)-1-{1-[2-(trifluoromethyl)phenyl]piperidin-4-yl}pyridazin-4(1H)-one | 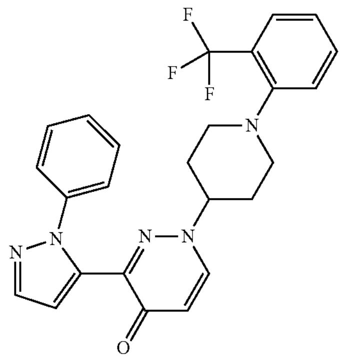 [SMILES: O=c1ccn(C2CCN(c3ccccc3C(F)(F)F)CC2)nc1-c1ccnn1-c1ccccc1] | — | 465.2 |

The compounds of Examples 65-96 shown in the following Tables were produced in the same manner as in Example 64. In the Tables, MS shows measured values.

TABLE 2-1

| Ex. No. | IUPAC name | structure | salt | MS |
|---|---|---|---|---|
| 65 | 3-(1-phenyl-1H-pyrazol-5-yl)-1-{1-[3-(trifluoromethyl)phenyl]piperidin-4-yl}pyridazin-4(1H)-one | 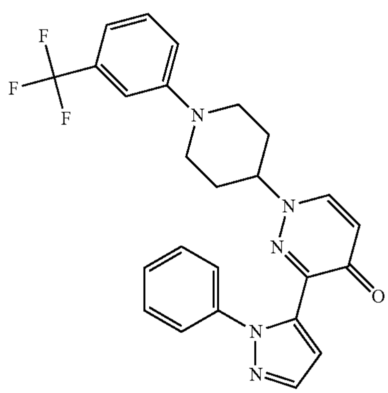 [SMILES: O=c1ccn(C2CCN(c3cccc(C(F)(F)F)c3)CC2)nc1-c1ccnn1-c1ccccc1] | — | 465.2 |
| 66 | 3-(1-phenyl-1H-pyrazol-5-yl)-1-{1-[2-(trifluoromethoxy)phenyl]piperidin-4-yl}pyridazin-4(1H)-one | 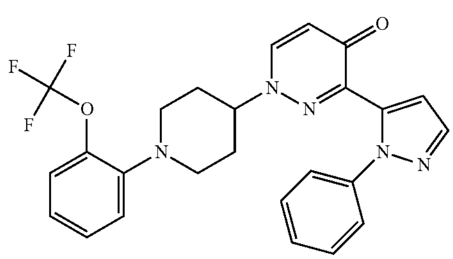 [SMILES: O=c1ccn(C2CCN(c3ccccc3OC(F)(F)F)CC2)nc1-c1ccnn1-c1ccccc1] | — | 481.2 |
| 67 | 1-[1-(2-chlorophenyl)piperidin-4-yl]-3-(1-phenyl-1H-pyrazol-5-yl)pyridazin-4(1H)-one | 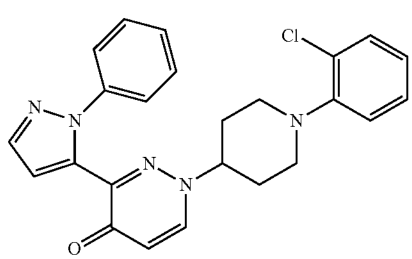 [SMILES: O=c1ccn(C2CCN(c3ccccc3Cl)CC2)nc1-c1ccnn1-c1ccccc1] | — | 431.2 |

TABLE 2-1-continued

| Ex. No. | IUPAC name | structure | salt | MS |
|---|---|---|---|---|
| 68 | 1-[1-(3-chlorophenyl)piperidin-4-yl]-3-(1-phenyl-1H-pyrazol-5-yl)pyridazin-4(1H)-one | 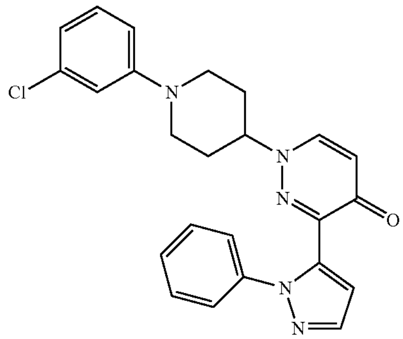 [SMILES: O=c1ccn(C2CCN(c3cccc(Cl)c3)CC2)nc1-c1ccnn1-c1ccccc1] | — | 431.2 |
| 69 | 1-[1-(4-chlorophenyl)piperidin-4-yl]-3-(1-phenyl-1H-pyrazol-5-yl)pyridazin-4(1H)-one | 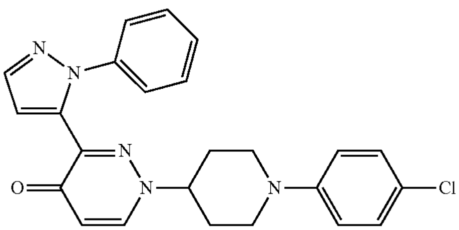 [SMILES: O=c1ccn(C2CCN(c3ccc(Cl)cc3)CC2)nc1-c1ccnn1-c1ccccc1] | — | 431.2 |

TABLE 2-2

| Ex. No. | IUPAC name | structure | salt | MS |
|---|---|---|---|---|
| 70 | 1-{1-[2-(difluoromethoxy)phenyl]piperidin-4-yl}-3-(1-phenyl-1H-pyrazol-5-yl)pyridazin-4(1H)-one | 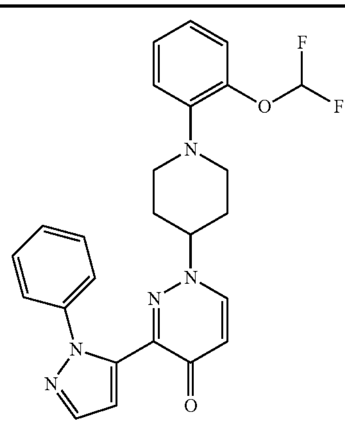 | — | 463.2 |
| 71 | 1-[1-(2,6-dichlorophenyl)piperidin-4-yl]-3-(1-phenyl-1H-pyrazol-5-yl)pyridazin-4(1H)-one | 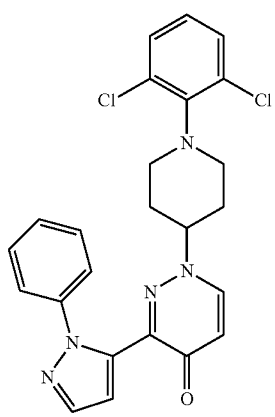 [SMILES: O=c1ccn(C2CCN(c3c(Cl)cccc3Cl)CC2)nc1-c1ccnn1-c1ccccc1] | — | 465.1 |

TABLE 2-2-continued

| Ex. No. | IUPAC name | structure | salt | MS |
|---|---|---|---|---|
| 72 | 3-(1-phenyl-1H-pyrazol-5-yl)-1-{1-[5-(trifluoromethyl)pyridin-2-yl]piperidin-4-yl}pyridazin-4(1H)-one | 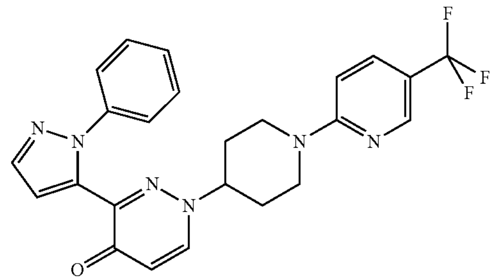 [SMILES: O=c1ccn(C2CCN(c3ccc(C(F)(F)F)cn3)CC2)nc1-c1ccnn1-c1ccccc1] | — | 466.2 |
| 73 | 1-[1-(2-methoxyphenyl)piperidin-4-yl]-3-(1-phenyl-1H-pyrazol-5-yl)pyridazin-4(1H)-one | 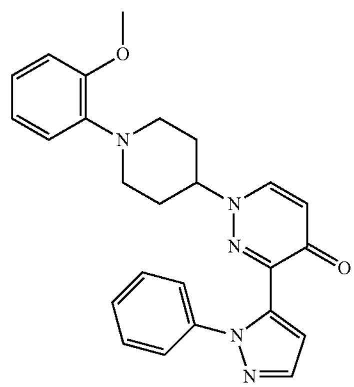 [SMILES: COc1ccccc1N1CCC(n2ccc(=O)c(-c3ccnn3-c3ccccc3)n2)CC1] | — | 427.2 |
| 74 | 1-[1-(3-methoxyphenyl)piperidin-4-yl]-3-(1-phenyl-1H-pyrazol-5-yl)pyridazin-4(1H)-one | 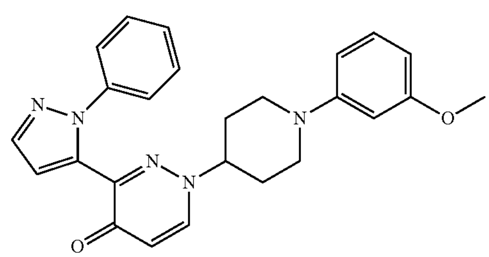 [SMILES: COc1cccc(N2CCC(n3ccc(=O)c(-c4ccnn4-c4ccccc4)n3)CC2)c1] | — | 427.2 |

TABLE 2-3

| Ex. No. | IUPAC name | structure | salt | MS |
|---|---|---|---|---|
| 75 | 1-[1-(4-methoxyphenyl)piperidin-4-yl]-3-(1-phenyl-1H-pyrazol-5-yl)pyridazin-4(1H)-one | 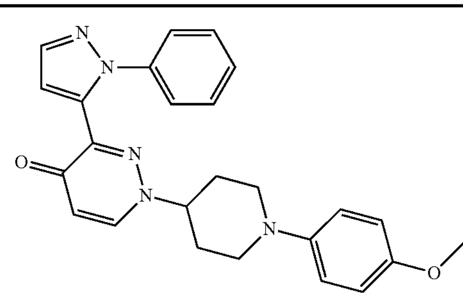 | — | 427.2 |

TABLE 2-3-continued

| Ex. No. | IUPAC name | structure | salt | MS |
|---|---|---|---|---|
| 76 | 1-{1-[4-(dimethylamino)-phenyl]piperidin-4-yl}-3-(1-phenyl-1H-pyrazol-5-yl)pyridazin-4(1H)-one | 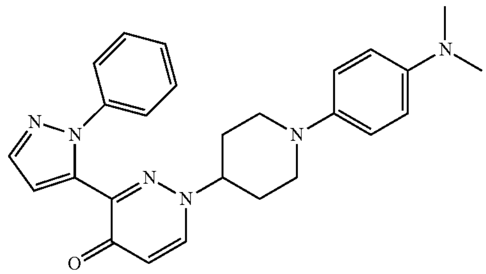 [SMILES: CN(C)c1ccc(N2CCC(n3ccc(=O)c(-c4ccnn4-c4ccccc4)n3)CC2)cc1] | — | 440.2 |
| 77 | 2-{4-[4-oxo-3-(1-phenyl-1H-pyrazol-5-yl)pyridazin-1(4H)-yl]piperidin-1-yl}benzonitrile | 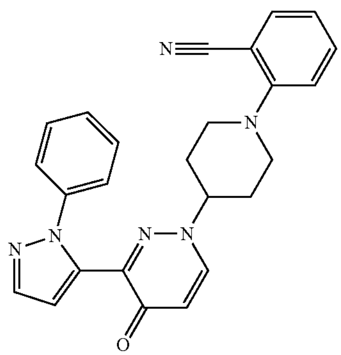 [SMILES: N#Cc1ccccc1N1CCC(n2ccc(=O)c(-c3ccnn3-c3ccccc3)n2)CC1] | — | 422.2 |
| 78 | 3-{4-[4-oxo-3-(1-phenyl-1H-pyrazol-5-yl)pyridazin-1(4H)-yl]piperidin-1-yl}benzonitrile | 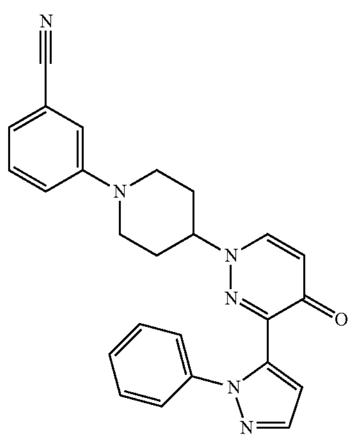 [SMILES: N#Cc1cccc(N2CCC(n3ccc(=O)c(-c4ccnn4-c4ccccc4)n3)CC2)c1] | — | 422.2 |
| 79 | 4-{4-[4-oxo-3-(1-phenyl-1H-pyrazol-5-yl)pyridazin-1(4H)-yl]piperidin-1-yl}benzonitrile | 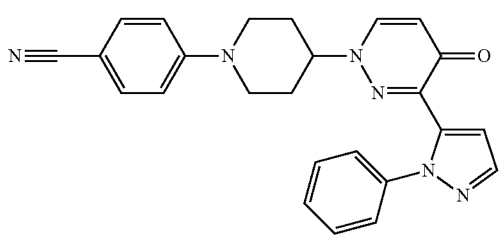 [SMILES: N#Cc1ccc(N2CCC(n3ccc(=O)c(-c4ccnn4-c4ccccc4)n3)CC2)cc1] | — | 422.2 |

TABLE 2-4

| Ex. No. | IUPAC name | structure | salt | MS |
|---|---|---|---|---|
| 80 | 1-[1-(2-methylphenyl)piperidin-4-yl]-3-(1-phenyl-1H-pyrazol-5-yl)pyridazin-4(1H)-one | 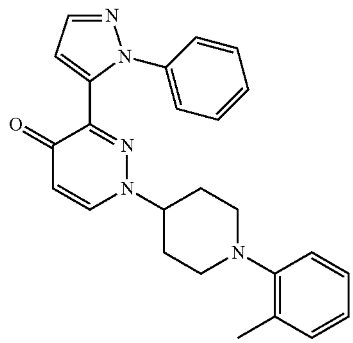 [SMILES: Cc1ccccc1N1CCC(n2ccc(=O)c(-c3ccnn3-c3ccccc3)n2)CC1] | — | 411.2 |
| 81 | 1-[1-(3-methylphenyl)piperidin-4-yl]-3-(1-phenyl-1H-pyrazol-5-yl)pyridazin-4(1H)-one | 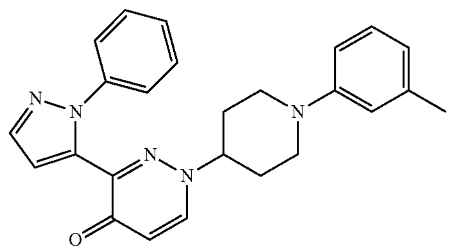 [SMILES: Cc1cccc(N2CCC(n3ccc(=O)c(-c4ccnn4-c4ccccc4)n3)CC2)c1] | — | 411.2 |
| 82 | 1-[1-(4-methylphenyl)piperidin-4-yl]-3-(1-phenyl-1H-pyrazol-5-yl)pyridazin-4(1H)-one | 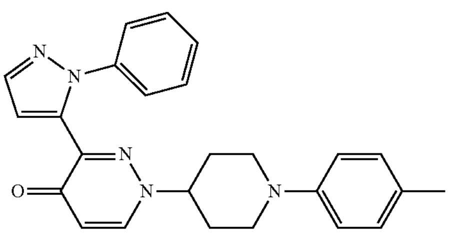 [SMILES: Cc1ccc(N2CCC(n3ccc(=O)c(-c4ccnn4-c4ccccc4)n3)CC2)cc1] | — | 411.2 |
| 83 | 1-[1-(3-acetylphenyl)piperidin-4-yl]-3-(1-phenyl-1H-pyrazol-5-yl)pyridazin-4(1H)-one | 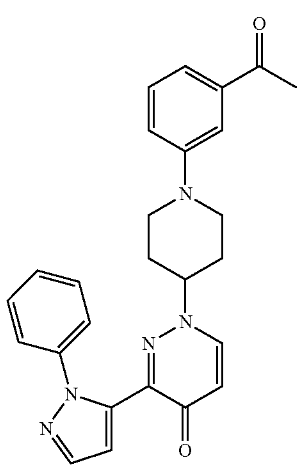 [SMILES: CC(=O)c1cccc(N2CCC(n3ccc(=O)c(-c4ccnn4-c4ccccc4)n3)CC2)c1] | — | 439.2 |
| 84 | 1-[1-(4-acetylphenyl)piperidin-4-yl]-3-(1-phenyl-1H-pyrazol-5-yl)pyridazin-4(1H)-one | 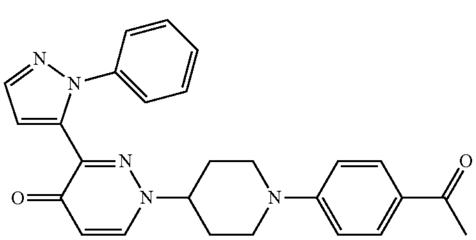 [SMILES: CC(=O)c1ccc(N2CCC(n3ccc(=O)c(-c4ccnn4-c4ccccc4)n3)CC2)cc1] | — | 439.2 |

TABLE 2-5

| Ex. No. | IUPAC name | structure | salt | MS |
|---|---|---|---|---|
| 85 | 1-(1-naphthalen-2-ylpiperidin-4-yl)-3-(1-phenyl-1H-pyrazol-5-yl)pyridazin-4(1H)-one | 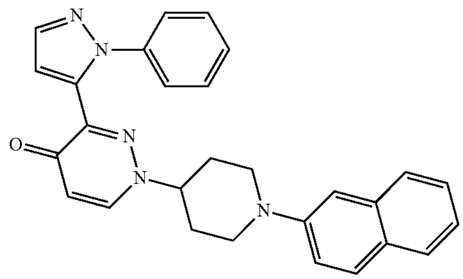 [SMILES: O=c1ccn(C2CCN(c3ccc4ccccc4c3)CC2)nc1-c1ccnn1-c1ccccc1] | — | 447.2 |
| 86 | 1-[1-(3,5-dichlorophenyl)piperidin-4-yl]-3-(1-phenyl-1H-pyrazol-5-yl)pyridazin-4(1H)-one | 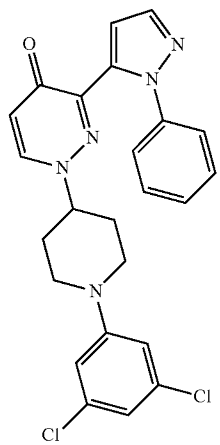 [SMILES: O=c1ccn(C2CCN(c3cc(Cl)cc(Cl)c3)CC2)nc1-c1ccnn1-c1ccccc1] | — | 465.1 |
| 87 | 1-[1-(2,3-dihydro-1-benzofuran-5-yl)piperidin-4-yl]-3-(1-phenyl-1H-pyrazol-5-yl)pyridazin-4(1H)-one | 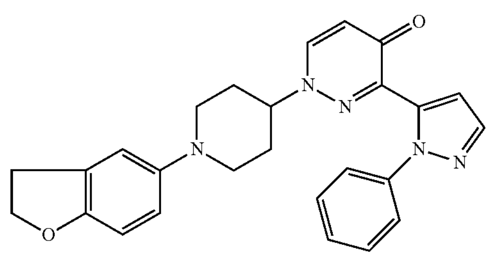 [SMILES: O=c1ccn(C2CCN(c3ccc4c(c3)CCO4)CC2)nc1-c1ccnn1-c1ccccc1] | — | 439.2 |
| 88 | 1-[1-(2,2-difluoro-1,3-benzodioxol-5-yl)piperidin-4-yl]-3-(1-phenyl-1H-pyrazol-5-yl)pyridazin-4(1H)-one | 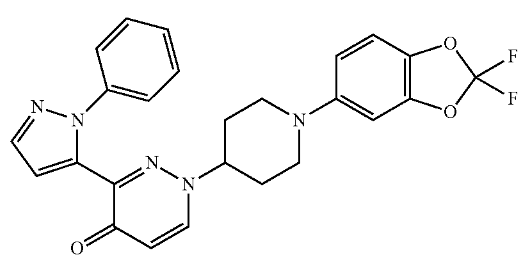 [SMILES: O=c1ccn(C2CCN(c3ccc4c(c3)OC(F)(F)O4)CC2)nc1-c1ccnn1-c1ccccc1] | — | 477.2 |
| 89 | 1-[1-(5-chlorothiophen-2-yl)piperidin-4-yl]-3-(1-phenyl-1H-pyrazol-5-yl)pyridazin-4(1H)-one | 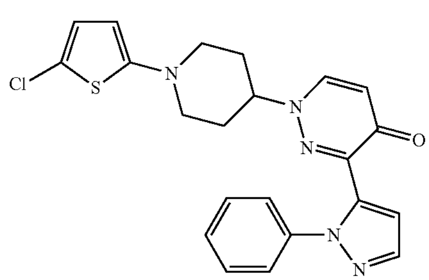 [SMILES: O=c1ccn(C2CCN(c3ccc(Cl)s3)CC2)nc1-c1ccnn1-c1ccccc1] | — | 437.1 |

TABLE 2-6

| Ex. No. | IUPAC name | structure | salt | MS |
|---|---|---|---|---|
| 90 | 1-[1-(2-methyl-1,3-benzothiazol-5-yl)piperidin-4-yl]-3-(1-phenyl-1H-pyrazol-5-yl)pyridazin-4(1H)-one | 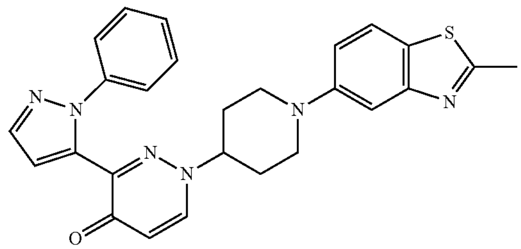 [SMILES: Cc1nc2cc(N3CCC(n4ccc(=O)c(-c5ccnn5-c5ccccc5)n4)CC3)ccc2s1] | — | 468.2 |
| 91 | 1-[1-(1,3-benzothiazol-5-yl)piperidin-4-yl]-3-(1-phenyl-1H-pyrazol-5-yl)pyridazin-4(1H)-one | 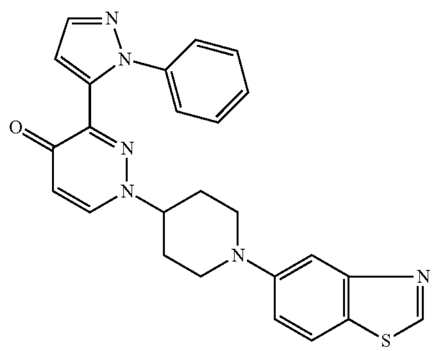 [SMILES: O=c1ccn(C2CCN(c3ccc4scnc4c3)CC2)nc1-c1ccnn1-c1ccccc1] | — | 454.2 |
| 92 | 1-[1-(1-benzofuran-5-yl)piperidin-4-yl]-3-(1-phenyl-1H-pyrazol-5-yl)pyridazin-4(1H)-one | 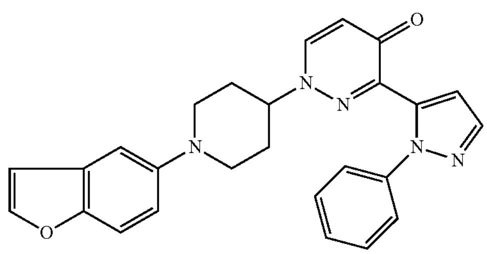 [SMILES: O=c1ccn(C2CCN(c3ccc4occc4c3)CC2)nc1-c1ccnn1-c1ccccc1] | — | 437.2 |
| 93 | 1-[1-(1,3-benzothiazol-6-yl)piperidin-4-yl]-3-(1-phenyl-1H-pyrazol-5-yl)pyridazin-4(1H)-one | 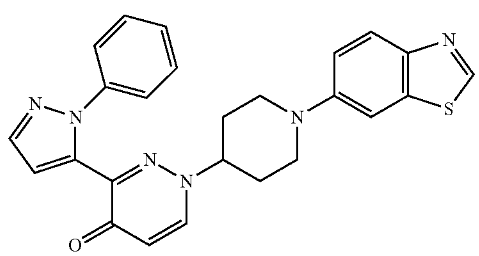 [SMILES: O=c1ccn(C2CCN(c3ccc4ncsc4c3)CC2)nc1-c1ccnn1-c1ccccc1] | — | 454.2 |
| 94 | 1-{1-[4-(methylsulfonyl)phenyl]piperidin-4-yl}-3-(1-phenyl-1H-pyrazol-5-yl)pyridazin-4(1H)-one | 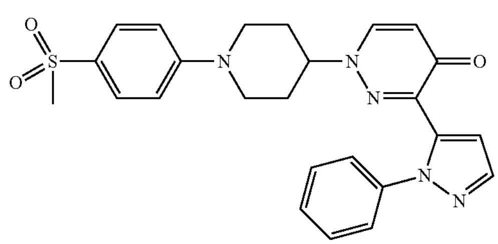 [SMILES: CS(=O)(=O)c1ccc(N2CCC(n3ccc(=O)c(-c4ccnn4-c4ccccc4)n3)CC2)cc1] | — | 475.2 |

TABLE 2-7

| Ex. No. | IUPAC name | structure | salt | MS |
|---|---|---|---|---|
| 95 | 3-(1-phenyl-1H-pyrazol-5-yl)-1-{1-[6-(trifluoromethyl)pyridin-3-yl]piperidin-4-yl}pyridazin-4(1H)-one | 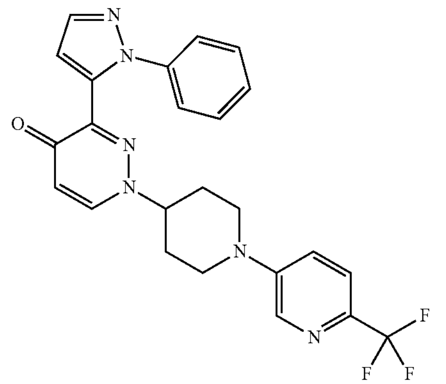 [SMILES: O=c1ccn(C2CCN(c3ccc(C(F)(F)F)nc3)CC2)nc1-c1ccnn1-c1ccccc1] | — | 466.2 |
| 96 | 1-[1-(5-acetylthiophen-2-yl)piperidin-4-yl]-3-(1-phenyl-1H-pyrazol-5-yl)pyridazin-4(1H)-one | 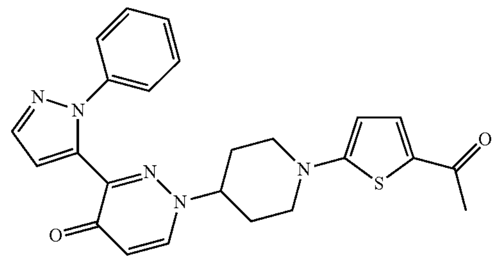 [SMILES: CC(=O)c1ccc(N2CCC(n3ccc(=O)c(-c4ccnn4-c4ccccc4)n3)CC2)s1] | — | 445.2 |

Example 97

5-methoxy-3-(1-phenyl-1H-pyrazol-5-yl)-1-(1,2,3,4-tetrahydronaphthalen-1-yl)pyridazin-4(1H)-one The title compound (11 mg) was obtained in the same manner as in Example 58.

MS (ESI+): [M+H]$^+$ 399.1

Example 98

5-methoxy-3-(1-phenyl-1H-pyrazol-5-yl)-1-{1-[3-(trifluoromethyl)pyridin-2-yl]azetidin-3-yl}pyridazin-4(1H)-one A) 1-[3-(trifluoromethyl)pyridin-2-yl]azetidin-3-ol A suspension of azetidin-3-ol hydrochloride (500 mg), 2-chloro-3-(trifluoromethyl)pyridine (425 mg) and cesium carbonate (1.14 g) in DMF (5 ml) was stirred at 50° C. for 12 hr, and water was added. The reaction mixture was extracted with ethyl acetate, the extract was dried over anhydrous magnesium sulfate, and concentrated under reduced pressure. The residue was purified by silica gel column chromatography (hexane/ethyl acetate) to give the title compound (120 mg).

$^1$H NMR (300 MHz, DMSO-d$_6$) δ3.76-3.93 (2H, m), 4.23-4.36 (2H, m), 4.45-4.62 (1H, m), 5.66 (1H, d, J=6.4 Hz), 6.65-6.86 (1H, m), 7.78-7.94 (1H, m), 8.21-8.39 (1H, m).

B) 5-methoxy-3-(1-phenyl-1H-pyrazol-5-yl)-1-{1-[3-(trifluoromethyl)pyridin-2-yl]azetidin-3-yl}pyridazin-4(1H)-one The title compound (35 mg) was obtained in the same manner as in Example 58.

MS (ESI+): [M+H]$^+$ 399.1

Example 99

5-methoxy-1-[1-(phenylcarbonyl)azetidin-3-yl]-3-(1-phenyl-1H-pyrazol-5-yl)pyridazin-4(1H)-one A) 1-(phenylcarbonyl)azetidin-3-ol To a mixture of azetidin-3-ol hydrochloride (200 mg), saturated aqueous sodium hydrogen carbonate solution (2 mL) and THF (2 mL) was added benzoylchloride (132 mg) under ice-cooling. The reaction mixture was stirred at room temperature for 3 days, water was added, and the mixture was extracted with ethyl acetate. The extract was dried over anhydrous magnesium sulfate, and concentrated under reduced pressure. The residue was purified by silica gel column chromatography (methanol/ethyl acetate) to give the title compound (130 mg).

$^1$H NMR (300 MHz, DMSO-d$_6$) δ3.69-3.85 (1H, m), 3.94-4.08 (1H, m), 4.16-4.29 (1H, m), 4.36-4.57 (2H, m), 5.74 (1H, d, J=6.0 Hz), 7.36-7.58 (3H, m), 7.57-7.68 (2H, m).

B) 5-methoxy-1-[1-(phenylcarbonyl)azetidin-3-yl]-3-(1-phenyl-1H-pyrazol-5-yl)pyridazin-4(1H)-one The title compound (37 mg) was obtained in the same manner as in Example 58.

MS (ESI+): [M+H]$^+$ 428.3

Example 100

5-methoxy-1-(1-phenylazetidin-3-yl)-3-(1-phenyl-1H-pyrazol-5-yl)pyridazin-4(1H)-one

A) azetidin-3-ylbenzoate hydrochloride

To a solution of tert-butyl 3-hydroxyazetidine-1-carboxylate (1 g), triethylamine (1.2 mL) and DMAP (7 mg) in THF (10 ml) was added benzoylchloride (0.81 g) under ice-cooling. The reaction mixture was stirred at room temperature for 2 hr, water was added, and the mixture was extracted with ethyl acetate. The extract was dried over anhydrous magnesium sulfate, and concentrated under reduced pressure. The residue was dissolved in ethyl acetate (10 mL), and 4M hydrogen chloride in ethyl acetate solution (3 mL) was added. The reaction mixture was stirred at room temperature for 2 hr, and the precipitate was collected by filtration to give the title compound (710 mg).

$^1$H NMR (300 MHz, DMSO-$d_6$) δ4.15 (2H, brs), 4.35 (2H, brs), 5.29-5.49 (1H, m), 7.47-7.68 (2H, m), 7.65-7.81 (1H, m), 7.95-8.07 (2H, m), 9.21-9.85 (2H, m).

B) 1-phenylazetidin-3-ol

A suspension of azetidin-3-ylbenzoate hydrochloride (600 mg), bromobenzene (530 mg), Pd$_2$(dba)$_3$ (129 mg), Xantphos (134 mg) and sodium tert-butoxide (515 mg) in toluene (12 mL) was irradiated with microwave at 150° C. for 30 min under an argon atmosphere. The reaction mixture was filtered and concentrated under reduced pressure. The residue was dissolved in ethanol (12 mL), and 1N aqueous sodium hydroxide solution (3 mL) was added. The reaction mixture was stirred at room temperature for 1 hr, water was added, and the mixture was extracted with ethyl acetate. The extract was dried over anhydrous magnesium sulfate and concentrated under reduced pressure. The residue was purified by basic silica gel column chromatography (hexane/ethyl acetate) to give the title compound (131 mg).

$^1$H NMR (300 MHz, DMSO-$d_6$) δ3.40-3.50 (2H, m), 3.98-4.14 (2H, m), 4.48-4.62 (1H, m), 5.57 (1H, d, J=6.8 Hz), 6.41 (2H, d, J=7.6 Hz), 6.61-6.71 (1H, m), 7.11-7.21 (2H, m).

C) 5-methoxy-1-(1-phenylazetidin-3-yl)-3-(1-phenyl-1H-pyrazol-5-yl)pyridazin-4(1H)-one The title compound (26 mg) was obtained in the same manner as in Example 58.
MS (ESI+): [M+H]$^+$ 400.4

Example 101

1-[1-(diphenylmethyl)azetidin-3-yl]-5-methoxy-3-(1-phenyl-1H-pyrazol-5-yl)pyridazin-4(1H)-one A suspension of 5-methoxy-3-(1-phenyl-1H-pyrazol-5-yl)pyridazin-4-ol (200 mg), 1-(diphenylmethyl)azetidin-3-yl methanesulfonate (354 mg) and cesium carbonate (729 mg) in DMF (5 mL) was stirred at 100° C. for 12 hr, and water was added. The reaction mixture was extracted with ethyl acetate, the extract was dried over anhydrous magnesium sulfate, and concentrated under reduced pressure. The residue was purified by silica gel column chromatography (hexane/ethyl acetate) to give the title compound (35 mg).
MS (ESI+): [M+H]$^+$ 490.4

Example 102

5-methoxy-3-(1-phenyl-1H-pyrazol-5-yl)-1-[2-(trifluoromethyl)benzyl]pyridazin-4(1H)-one To a solution of 5-methoxy-3-(1-phenyl-1H-pyrazol-5-yl)pyridazin-4-ol (21 mg) in DMF (0.5 mL) were added tetra n-butylammoniumiodide (9 mg) and 60% NaH oil mixture (4 mg) at 0° C., and the mixture was stirred as it was for 20 min. To the reaction mixture was added 2-(trifluoromethyl)benzyl bromide (24 mg), and the mixture was stirred at room temperature for 60 hr. To the reaction mixture was added water (0.5 mL), and the mixture was extracted with ethyl acetate (2 mL×2) (the extract was separated by an organic layer-separation filter). The extract was distilled by blowing air at 60° C., and the residue was dissolved in DMSO, and purified by preparative HPLC (column: YMC combiprep pro C18 RS, solvent: 10 mM NH$_4$HCO$_3$/MeCN). The obtained eluate containing the title compound was concentrated by blowing air at 60° C. to give the title compound (10.8 mg).
MS (ESI+): [M+H]$^+$ 427.1

The structures and the like of the compounds of Examples 97-102 are shown in the following Tables.

TABLE 3-1

| Ex. No. | IUPAC name | structure | salt | MS |
|---|---|---|---|---|
| 97 | 5-methoxy-3-(1-phenyl-1H-pyrazol-5-yl)-1-(1,2,3,4-tetrahydro-naphthalen-1-yl)-pyridazin-4(1H)-one | 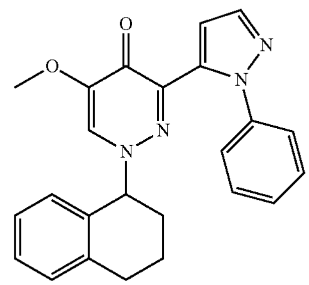 [SMILES: COc1cn(C2CCCc3ccccc32)nc(-c2ccnn2-c2ccccc2)c1=O] | — | 399.1 |
| 98 | 5-methoxy-3-(1-phenyl-1H-pyrazol-5-yl)-1-{1-[3-(trifluoromethyl)-pyridin-2-yl]-azetidin-3-yl}-pyridazin-4(1H)-one | 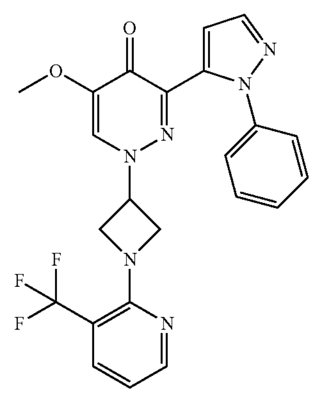 [SMILES: COc1cn(C2CN(c3ncccc3C(F)(F)F)C2)nc(-c2ccnn2-c2ccccc2)c1=O] | — | 399.1 |

TABLE 3-1-continued

| Ex. No. | IUPAC name | structure | salt | MS |
|---|---|---|---|---|
| 99 | 5-methoxy-1-[1-(phenylcarbonyl)-azetidin-3-yl]-3-(1-phenyl-1H-pyrazol-5-yl)pyridazin-4(1H)-one | 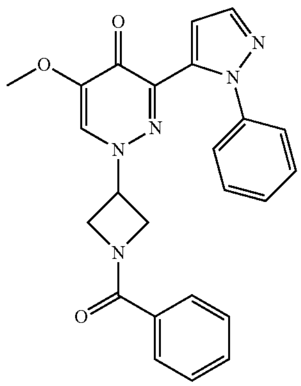 [SMILES: COc1cn(C2CN(C(=O)c3ccccc3)C2)nc(-c2ccnn2-c2ccccc2)c1=O] | — | 428.3 |
| 100 | 5-methoxy-1-(1-phenyl-azetidin-3-yl)-3-(1-phenyl-1H-pyrazol-5-yl)pyridazin-4(1H)-one | 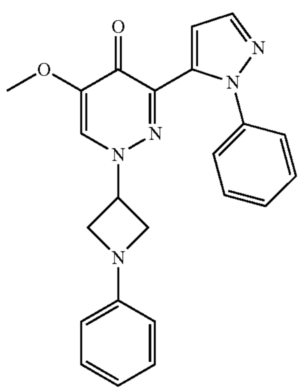 [SMILES: COc1cn(C2CN(c3ccccc3)C2)nc(-c2ccnn2-c2ccccc2)c1=O] | — | 400.4 |
| 101 | 1-[1-(diphenyl-methyl)-azetidin-3-yl]-5-methoxy-3-(1-phenyl-1H-pyrazol-5-yl)-pyridazin-4(1H)-one | 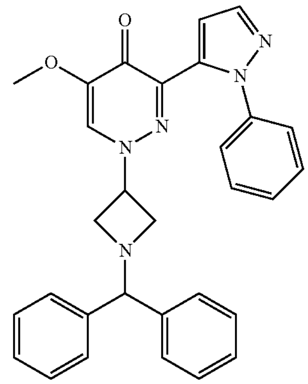 [SMILES: COc1cn(C2CN(C(c3ccccc3)c3ccccc3)C2)nc(-c2ccnn2-c2ccccc2)c1=O] | — | 490.4 |

TABLE 3-2

| Ex. No. | IUPAC name | structure | salt | MS |
|---|---|---|---|---|
| 102 | 5-methoxy-3-(1-phenyl-1H-pyrazol-5-yl)-1-[2-(trifluoro-methyl)-benzyl]pyridazin-4(1H)-one | 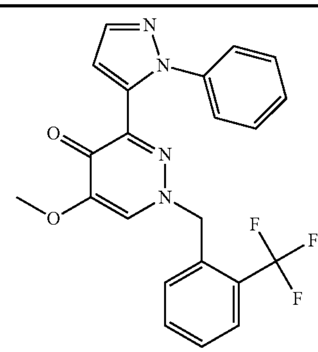 | — | 427.1 |

The compounds of Examples 103-138 shown in the following Tables were produced in the same manner as in Example 102. MS in the Tables shows measured values.

TABLE 4-1

| Ex. No. | IUPAC name | structure | salt | MS |
|---|---|---|---|---|
| 103 | 5-methoxy-3-(1-phenyl-1H-pyrazol-5-yl)-1-[3-(trifluoromethyl)benzyl]pyridazin-4(1H)-one | 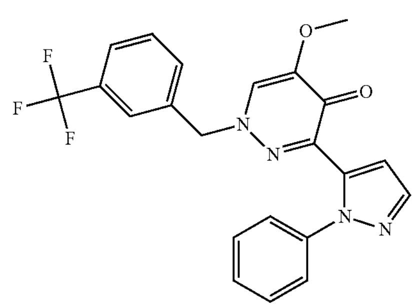 [SMILES: COc1cn(Cc2cccc(C(F)(F)F)c2)nc(-c2ccnn2-c2ccccc2)c1=O] | — | 427.1 |

TABLE 4-1-continued

| Ex. No. | IUPAC name | structure | salt | MS |
|---|---|---|---|---|
| 104 | 5-methoxy-3-(1-phenyl-1H-pyrazol-5-yl)-1-[4-(trifluoromethyl)benzyl]pyridazin-4(1H)-one | 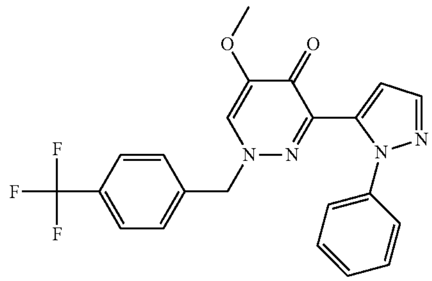 [SMILES: COc1cn(Cc2ccc(C(F)(F)F)cc2)nc(-c2ccnn2-c2ccccc2)c1=O] | — | 427.1 |
| 105 | 5-methoxy-1-(2-methoxybenzyl)-3-(1-phenyl-1H-pyrazol-5-yl)pyridazin-4(1H)-one | 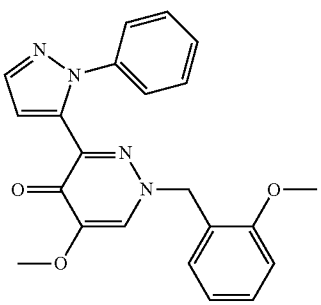 [SMILES: COc1ccccc1Cn1cc(OC)c(=O)c(-c2ccnn2-c2ccccc2)n1] | — | 389.2 |
| 106 | 5-methoxy-1-(3-methoxybenzyl)-3-(1-phenyl-1H-pyrazol-5-yl)pyridazin-4(1H)-one | 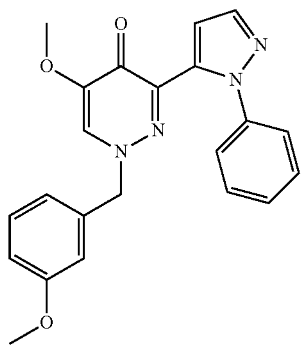 [SMILES: COc1cccc(Cn2cc(OC)c(=O)c(-c3ccnn3-c3ccccc3)n2)c1] | — | 389.2 |
| 107 | 5-methoxy-1-(4-methoxybenzyl)-3-(1-phenyl-1H-pyrazol-5-yl)pyridazin-4(1H)-one | 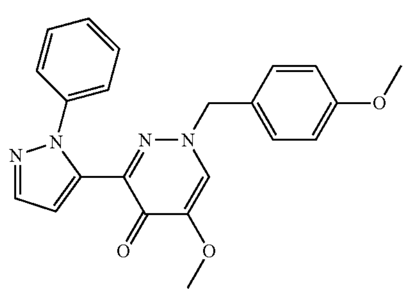 [SMILES: COc1ccc(Cn2cc(OC)c(=O)c(-c3ccnn3-c3ccccc3)n2)cc1] | — | 389.2 |

TABLE 4-2

| Ex. No. | IUPAC name | structure | salt | MS |
|---|---|---|---|---|
| 108 | 2-{[5-methoxy-4-oxo-3-(1-phenyl-1H-pyrazol-5-yl)pyridazin-1(4H)-yl]methyl}benzonitrile | 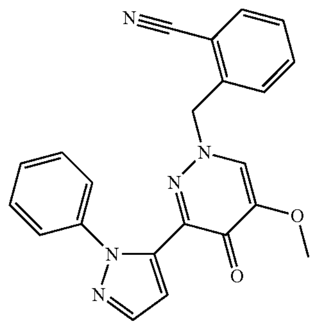 [SMILES: COc1cn(Cc2ccccc2C#N)nc(-c2ccnn2-c2ccccc2)c1=O] | — | 384.1 |
| 109 | 3-{[5-methoxy-4-oxo-3-(1-phenyl-1H-pyrazol-5-yl)pyridazin-1(4H)-yl]methyl}benzonitrile | 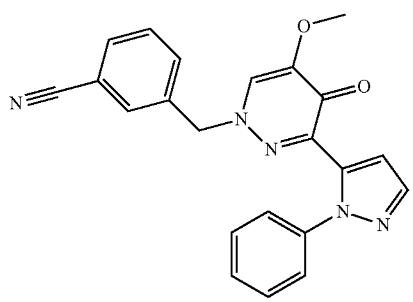 [SMILES: COc1cn(Cc2cccc(C#N)c2)nc(-c2ccnn2-c2ccccc2)c1=O] | — | 384.1 |
| 110 | 4-{[5-methoxy-4-oxo-3-(1-phenyl-1H-pyrazol-5-yl)pyridazin-1(4H)-yl]methyl}benzonitrile | 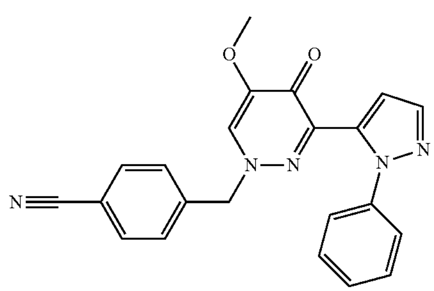 [SMILES: COc1cn(Cc2ccc(C#N)cc2)nc(-c2ccnn2-c2ccccc2)c1=O] | — | 384.1 |
| 111 | methyl 3-{[5-methoxy-4-oxo-3-(1-phenyl-1H-pyrazol-5-yl)pyridazin-1(4H)-yl]methyl}benzoate | 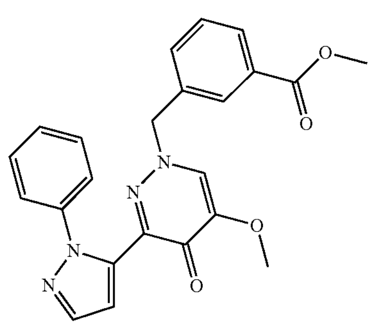 [SMILES: COC(=O)c1cccc(Cn2cc(OC)c(=O)c(-c3ccnn3-c3ccccc3)n2)c1] | — | 417.2 |

TABLE 4-2-continued
| Ex. No. | IUPAC name | structure | salt | MS |
|---|---|---|---|---|
| 112 | methyl 4-{[5-methoxy-4-oxo-3-(1-phenyl-1H-pyrazol-5-yl)pyridazin-1(4H)-yl]methyl}benzoate | 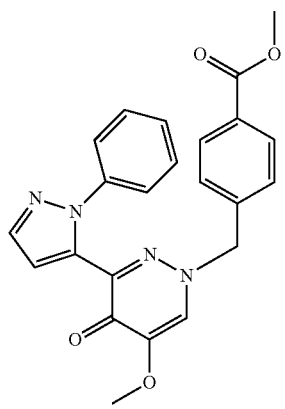 [SMILES: COC(=O)c1ccc(Cn2cc(OC)c(=O)c(-c3ccnn3-c3ccccc3)n2)cc1] | — | 417.2 |
TABLE 4-3
| Ex. No. | IUPAC name | structure | salt | MS |
|---|---|---|---|---|
| 113 | 5-methoxy-1-(1-phenylethyl)-3-(1-phenyl-1H-pyrazol-5-yl)pyridazin-4(1H)-one | 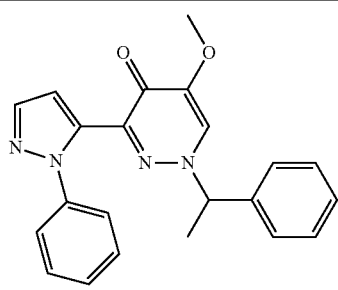 | — | 373.2 |
| 114 | 5-methoxy-3-(1-phenyl-1H-pyrazol-5-yl)-1-(pyridin-2-ylmethyl)pyridazin-4(1H)-one | 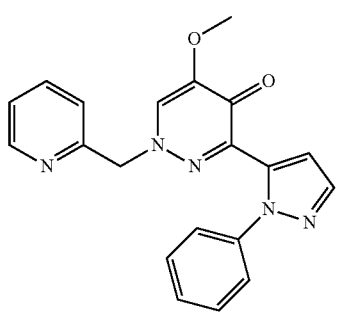 [SMILES: COc1cn(Cc2ccccn2)nc(-c2ccnn2-c2ccccc2)c1=O] | — | 360.1 |
| 115 | 5-methoxy-3-(1-phenyl-1H-pyrazol-5-yl)-1-(pyridin-4-ylmethyl)pyridazin-4(1H)-one | 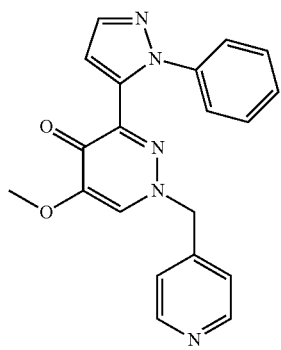 [SMILES: COc1cn(Cc2ccncc2)nc(-c2ccnn2-c2ccccc2)c1=O] | — | 360.1 |

TABLE 4-3-continued

| Ex. No. | IUPAC name | structure | salt | MS |
|---|---|---|---|---|
| 116 | 5-methoxy-3-(1-phenyl-1H-pyrazol-5-yl)-1-(quinolin-2-ylmethyl)pyridazin-4(1H)-one | 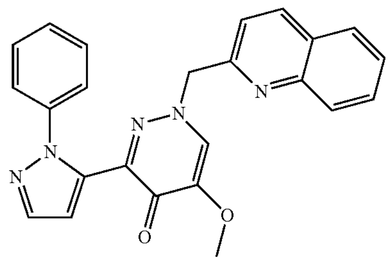 [SMILES: COc1cn(Cc2ccc3ccccc3n2)nc(-c2ccnn2-c2ccccc2)c1=O] | — | 410.1 |
| 117 | 1-(isoquinoline-1-ylmethyl)-5-methoxy-3-(1-phenyl-1H-pyrazol-5-yl)pyridazin-4(1H)-one | 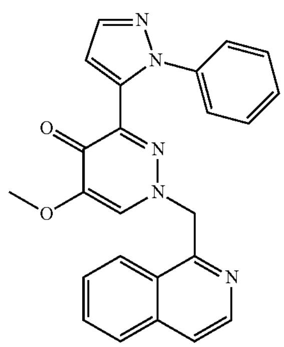 [SMILES: COc1cn(Cc2nccc3ccccc23)nc(-c2ccnn2-c2ccccc2)c1=O] | — | 410.1 |

TABLE 4-4

| Ex. No. | IUPAC name | structure | salt | MS |
|---|---|---|---|---|
| 118 | 5-methoxy-1-{[3-methyl-4-(2,2,2-trifluoroethoxy)pyridin-2-yl]methyl}-3-(1-phenyl-1H-pyrazol-5-yl)pyridazin-4(1H)-one | 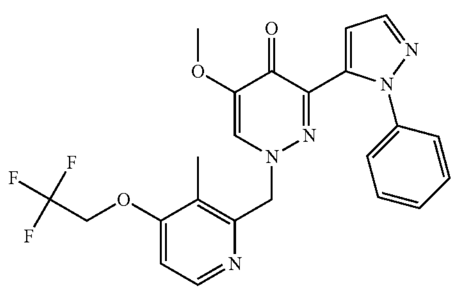 [SMILES: COc1cn(Cc2nccc(OCC(F)(F)F)c2C)nc(-c2ccnn2-c2ccccc2)c1=O] | — | 472.1 |
| 119 | methyl 6-{[5-methoxy-4-oxo-3-(1-phenyl-1H-pyrazol-5-yl)pyridazin-1(4H)-yl]methyl}pyridine-2-carboxylate | 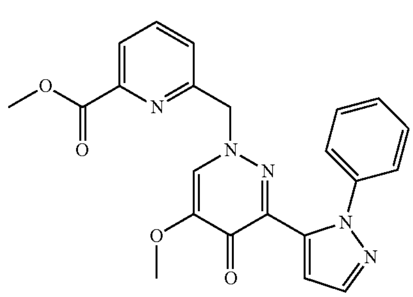 [SMILES: COC(=O)c1cccc(Cn2cc(OC)c(=O)c(-c3ccnn3-c3ccccc3)n2)n1] | — | 418.1 |

TABLE 4-4-continued

| Ex. No. | IUPAC name | structure | salt | MS |
|---|---|---|---|---|
| 120 | ethyl 5-{[5-methoxy-4-oxo-3-(1-phenyl-1H-pyrazol-5-yl)pyridazin-1(4H)-yl]methyl}furan-2-carboxylate | 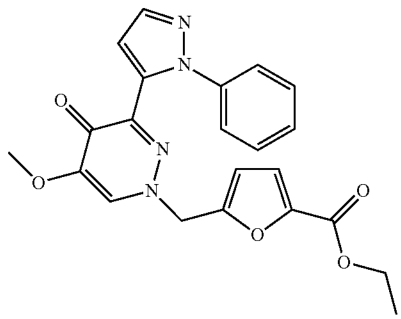 [SMILES: CCOC(=O)c1ccc(Cn2cc(OC)c(=O)c(-c3ccnn3-c3ccccc3)n2)o1] | — | 421.1 |
| 121 | 5-methoxy-3-(1-phenyl-1H-pyrazol-5-yl)-1-{[5-(trifluoromethyl)furan-2-yl]methyl}pyridazin-4(1H)-one | 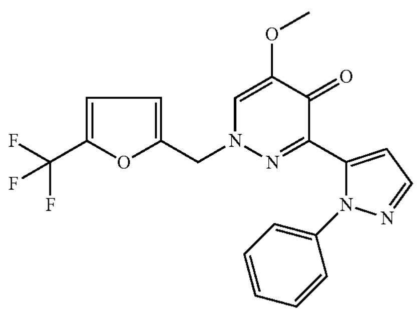 [SMILES: COc1cn(Cc2ccc(C(F)(F)F)o2)nc(-c2ccnn2-c2ccccc2)c1=O] | — | 417.1 |
| 122 | 1-cyclobutyl-5-methoxy-3-(1-phenyl-1H-pyrazol-5-yl)pyridazin-4(1H)-one | 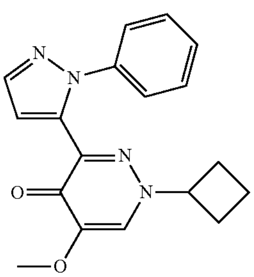 [SMILES: COc1cn(C2CCC2)nc(-c2ccnn2-c2ccccc2)c1=O] | — | 323.2 |

TABLE 4-5

| Ex. No. | IUPAC name | structure | salt | MS |
|---|---|---|---|---|
| 123 | 1-cyclopentyl-5-methoxy-3-(1-phenyl-1H-pyrazol-5-yl)pyridazin-4(1H)-one | 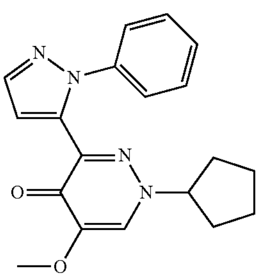 [SMILES: COc1cn(C2CCCC2)nc(-c2ccnn2-c2ccccc2)c1=O] | — | 337.1 |

TABLE 4-5-continued

| Ex. No. | IUPAC name | structure | salt | MS |
|---|---|---|---|---|
| 124 | 1-cyclohexyl-5-methoxy-3-(1-phenyl-1H-pyrazol-5-yl)pyridazin-4(1H)-one | 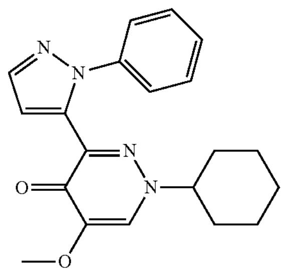 [SMILES: COc1cn(C2CCCCC2)nc(-c2ccnn2-c2ccccc2)c1=O] | — | 351.2 |
| 125 | 5-methoxy-3-(1-phenyl-1H-pyrazol-5-yl)-1-(3,3,3-trifluoropropyl)pyridazin-4(1H)-one | 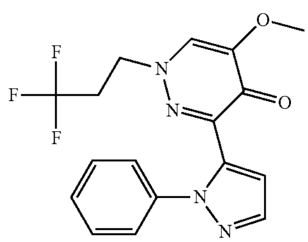 [SMILES: COc1cn(CCC(F)(F)F)nc(-c2ccnn2-c2ccccc2)c1=O] | — | 365.1 |
| 126 | 5-methoxy-3-(1-phenyl-1H-pyrazol-5-yl)-1-(tetrahydro-2H-pyran-2-ylmethyl)pyridazin-4(1H)-one | 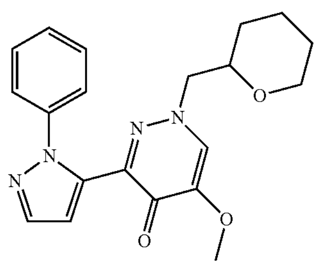 | — | 367.2 |
| 127 | 5-methoxy-3-(1-phenyl-1H-pyrazol-5-yl)-1-(tetrahydrofuran-2-ylmethyl)pyridazin-4(1H)-one | 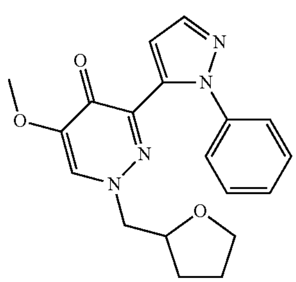 [SMILES: COc1cn(CC2CCCO2)nc(-c2ccnn2-c2ccccc2)c1=O] | — | 353.2 |

TABLE 4-6

| Ex. No. | IUPAC name | structure | salt | MS |
|---|---|---|---|---|
| 128 | 5-methoxy-3-(1-phenyl-1H-pyrazol-5-yl)-1-(2-piperidin-1-ylethyl)pyridazin-4(1H)-one | 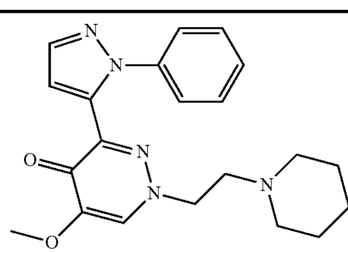 | — | 380.2 |

TABLE 4-6-continued

| Ex. No. | IUPAC name | structure | salt | MS |
|---|---|---|---|---|
| 129 | 5-methoxy-3-(1-phenyl-1H-pyrazol-5-yl)-1-(2-pyrrolidin-1-ylethyl)pyridazin-4(1H)-one | 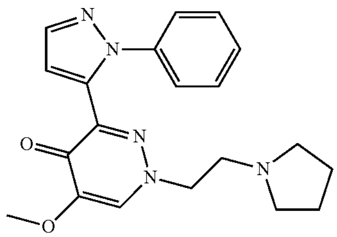 [SMILES: COc1cn(CCN2CCCC2)nc(-c2ccnn2-c2ccccc2)c1=O] | — | 366.2 |
| 130 | 5-methoxy-1-(2-morpholin-4-ylethyl)-3-(1-phenyl-1H-pyrazol-5-yl)pyridazin-4(1H)-one | 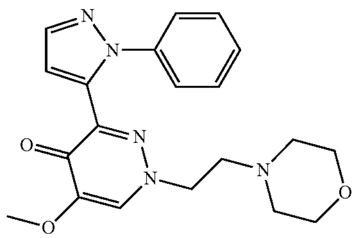 [SMILES: COc1cn(CCN2CCOCC2)nc(-c2ccnn2-c2ccccc2)c1=O] | — | 382.1 |
| 131 | 1-(cyclohexylmethyl)-5-methoxy-3-(1-phenyl-1H-pyrazol-5-yl)pyridazin-4(1H)-one | 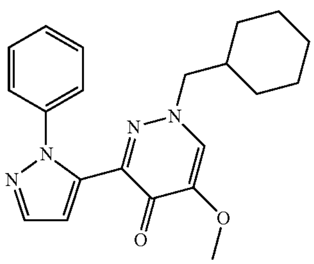 [SMILES: COc1cn(CC2CCCCC2)nc(-c2ccnn2-c2ccccc2)c1=O] | — | 365.2 |
| 132 | 1-(cyclobutylmethyl)-5-methoxy-3-(1-phenyl-1H-pyrazol-5-yl)pyridazin-4(1H)-one | 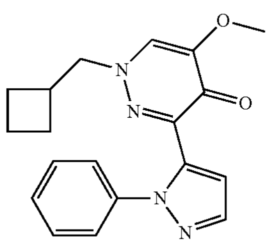 [SMILES: COc1cn(CC2CCC2)nc(-c2ccnn2-c2ccccc2)c1=O] | — | 337.2 |

TABLE 4-7

| Ex. No. | IUPAC name | structure | salt | MS |
|---|---|---|---|---|
| 133 | 5-methoxy-1-(2-phenylethyl)-3-(1-phenyl-1H-pyrazol-5-yl)pyridazin-4(1H)-one | 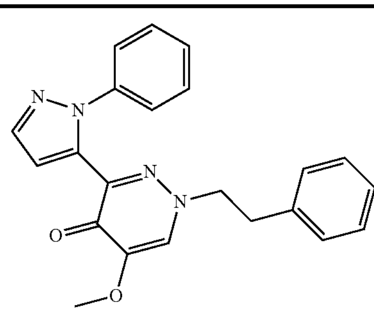 | — | 373.2 |

TABLE 4-7-continued

| Ex. No. | IUPAC name | structure | salt | MS |
|---|---|---|---|---|
| 134 | 1-(2-cyclohexylethyl)-5-methoxy-3-(1-phenyl-1H-pyrazol-5-yl)pyridazin-4(1H)-one | 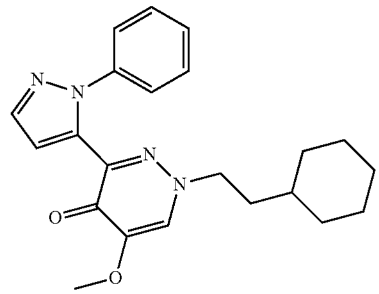 [SMILES: COc1cn(CCC2CCCCC2)nc(-c2ccnn2-c2ccccc2)c1=O] | — | 379.2 |
| 135 | 5-methoxy-1-(2-oxo-2-phenylethyl)-3-(1-phenyl-1H-pyrazol-5-yl)pyridazin-4(1H)-one | 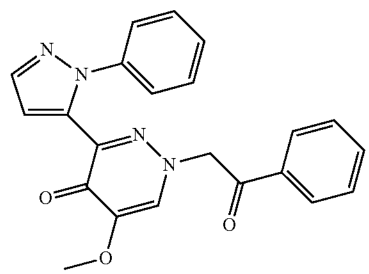 [SMILES: COc1cn(CC(=O)c2ccccc2)nc(-c2ccnn2-c2ccccc2)c1=O] | — | 387.1 |
| 136 | 5-methoxy-1-[(3-methyloxetan-3-yl)methyl]-3-(1-phenyl-1H-pyrazol-5-yl)pyridazin-4(1H)-one | 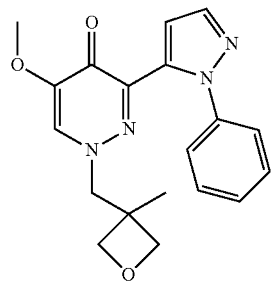 [SMILES: COc1cn(CC2(C)COC2)nc(-c2ccnn2-c2ccccc2)c1=O] | — | 353.2 |
| 137 | methyl 2-{[5-methoxy-4-oxo-3-(1-phenyl-1H-pyrazol-5-yl)pyridazin-1(4H)-yl]methyl}benzoate | 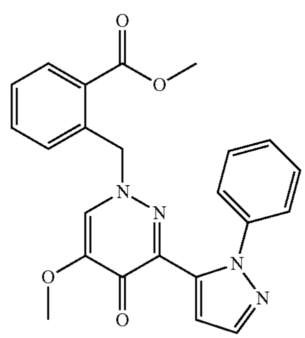 [SMILES: COC(=O)c1ccccc1Cn1cc(OC)c(=O)c(-c2ccnn2-c2ccccc2)n1] | — | 417.2 |
| 138 | 1-[3,5-bis(trifluoromethyl)benzyl]-5-methoxy-3-(1-phenyl-1H-pyrazol-5-yl)pyridazin-4(1H)-one | 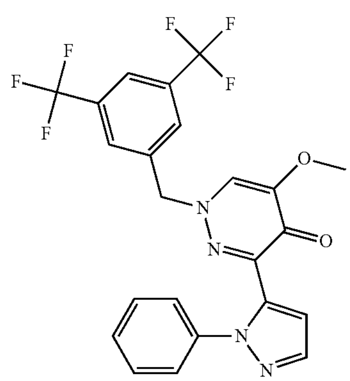 [SMILES: COc1cn(Cc2cc(C(F)(F)F)cc(C(F)(F)F)c2)nc(-c2ccnn2-c2ccccc2)c1=O] | — | 495.0 |

Example 139

3-(1-phenyl-1H-pyrazol-5-yl)-1-[1-(tetrahydro-2H-pyran-4-yl)piperidin-4-yl]pyridazin-4(1H)-one The title compound was obtained in the same manner as in Example 30.
MS (ESI+), found: 406.3

Example 140

2-phenyl-6-(1-phenyl-1H-pyrazol-5-yl)-4H-thiopyran-4-one

A) 1-phenyl-5-[(trimethylsilyl)ethynyl]-1H-pyrazole

To a solution of 5-iodo-1-phenyl-1H-pyrazole (2.00 g) (J. Org. Chem. 2008, 73, 1, 177-183) in triethylamine (40.0 mL) were added ethynyl(trimethyl)silane (0.80 g), CuI (0.141 g) and PdCl$_2$(PPh$_3$)$_2$ (0.260 g) under an argon atmosphere, and the mixture was stirred at 70° C. for 10 hr. The reaction mixture was filtered, and the filtrate was concentrated under reduced pressure. The residue was purified by silica gel column chromatography (dichloromethane) to give the title compound (1.54 g).
$^1$H-NMR (400 MHz, CDCl$_3$) δ 0.00 (9H, s), 6.42 (1H, d, J=1.6 Hz), 7.12-7.16 (1H, m), 7.23 (1H, t, J=16 Hz), 7.42 (1H, d, J=1.6 Hz), 7.58-7.60 (2H, m)

B) 5-ethynyl-1-phenyl-1H-pyrazole

To a solution of 1-phenyl-5-[(trimethylsilyl)ethynyl]-1H-pyrazole (1.20 g) in methanol (20.0 mL) was added potassium carbonate (0.173 g), and the mixture was stirred at room temperature for 3 hr. The reaction mixture was filtered, and the filtrate was concentrated to give the title compound (0.72 g).
$^1$H-NMR (400 MHz, CDCl$_3$) δ 2.37 (1H, d, J=8.0 Hz), 5.53 (1H, d, J=7.6 Hz), 6.70 (1H, d, J=2.0 Hz), 7.33-7.39 (4H, m), 7.41-7.47 (5H, m), 7.67 (1H, d, J=2.0 Hz), 7.76-7.79 (2H, m)

C) 1-phenyl-5-(1-phenyl-1H-pyrazol-5-yl)penta-1,4-diyn-3-ol

To a solution of 5-ethynyl-1-phenyl-1H-pyrazole (0.500 g) in THF (20.0 mL) was added dropwise 2.5M butyllithium in THF solution (1.55 mL) at −78° C., and the mixture was stirred for 30 min. To the reaction mixture was added dropwise a solution of 3-phenylprop-2-ynal (0.464 g) in THF (5.00 mL) at −78° C., the mixture was stirred for 45 min, and saturated aqueous ammonium chloride solution (10.0 mL) was added. The mixture was extracted with dichloromethane, the extract was washed with saturated brine, dried over anhydrous sodium sulfate, and the solvent was evaporated under reduced pressure. The residue was purified by silica gel column chromatography (dichloromethane/methanol) to give the title compound (0.73 g).
$^1$H-NMR (400 MHz, CDCl$_3$) δ 2.37 (1H, d, J=8.0 Hz), 5.53 (1H, d, J=7.6 Hz), 6.70 (1H, d, J=2.0 Hz), 7.33-7.39 (4H, m), 7.41-7.47 (5H, m), 7.67 (1H, d, J=2.0 Hz), 7.76-7.79 (2H, m)

D) 1-phenyl-5-(1-phenyl-1H-pyrazol-5-yl)penta-1,4-diyn-3-one

To a solution of 1-phenyl-5-(1-phenyl-1H-pyrazol-5-yl)penta-1,4-diyn-3-ol (0.50 g) in dichloromethane (20.0 mL) was added manganese dioxide (0.438 g), and the mixture was heated under reflux for 2 hr. The reaction mixture was filtered, and the filtrate was concentrated under reduced pressure. The residue was purified by silica gel column chromatography (dichloromethane) to give the title compound (0.310 g).
$^1$H-NMR (400 MHz, CDCl$_3$) δ 6.95 (1H, d, J=2.0 Hz), 7.41-7.44 (3H, m), 7.49-7.53 (3H, m), 7.56-7.59 (2H, m), 7.76-7.80 (3H, m)

E) 2-phenyl-6-(1-phenyl-1H-pyrazol-5-yl)-4H-thiopyran-4-one

To sodium sulfide (0.079 g) was added 0.25 M sodium ethoxide in ethanol solution (20.0 mL), and the mixture was stirred at room temperature for 10 min. To a solution of 1-phenyl-5-(1-phenyl-1H-pyrazol-5-yl)penta-1,4-diyn-3-one (0.25 g) in ethanol (10.0 mL) was added the above-mentioned solution, and the mixture was stirred at room temperature for 1 hr. The reaction mixture was filtered through celite, and the filtrate was concentrated under reduced pressure. The residue was purified by silica gel column chromatography (dichloromethane/methanol) to give the title compound (80.0 mg).
MS (ESI+): [M+H]$^+$ 331.2

Example 141

3-methoxy-5-phenyl-1-(1-phenyl-1H-pyrazol-5-yl)pyrazin-2(1H)-one

A) di-tert-butyl (1-phenyl-1H-pyrazol-5-yl)imidodicarbonate

To a mixture of 1-phenyl-1H-pyrazol-5-amine (3.00 g), triethylamine (5.72 g), DMAP (0.200 g) and dichloromethane (100 mL) was added di-tert-butyl-dicarbonate (10.3 g) at room temperature, and the mixture was stirred for 3 hr. The reaction mixture was washed with saturated brine, the organic layer was dried over anhydrous sodium sulfate, and the solvent was evaporated under reduced pressure. The residue was purified by silica gel column chromatography (dichloromethane/methanol) to give the title compound (5.37 g).
$^1$H-NMR (400 MHz, CDCl$_3$) δ 1.30 (18H, s), 1.32 (9H, s), 6.26 (1H, d, J=2.0 Hz), 7.37 (1H, d, J=6.4 Hz), 7.42-7.46 (4H, m), 7.65 (1H, d, J=2.0 Hz).

B) tert-butyl (1-phenyl-1H-pyrazol-5-yl)carbamate

To a solution of di-tert-butyl (1-phenyl-1H-pyrazol-5-yl)imidodicarbonate (5.30 g) in methanol (100 mL) was added 1N aqueous sodium hydroxide solution (73.0 mL) at room temperature, and the mixture was stirred at 50° C. for 2 hr. The reaction mixture was concentrated and adjusted to pH 5-6 with 2N hydrochloric acid. The reaction mixture was extracted with dichloromethane, and the extract was washed with saturated brine, dried over anhydrous sodium sulfate, and the solvent was evaporated under reduced pressure to give the title compound (3.80 g).
$^1$H-NMR (400 MHz, CDCl$_3$) δ 1.44 (9H, s), 6.43 (1H, brs), 6.67 (1H, s), 7.38-7.51 (5H, m), 7.56 (1H, d, J=2.0 Hz).

C) tert-butyl (cyanomethyl)(1-phenyl-1H-pyrazol-5-yl)carbamate

To a mixture of tert-butyl (1-phenyl-1H-pyrazol-5-yl)carbamate (3.80 g), 60% NaH (0.422 g) and THF (60.0 mL) was added bromoacetonitrile (1.93 g) at room temperature, and the mixture was stirred for 30 min. To the reaction mixture was added water, and the mixture was extracted with dichloromethane. The extract was washed with saturated brine, dried over anhydrous sodium sulfate, and the solvent was evaporated under reduced pressure to give the title compound (4.38 g).

$^1$H-NMR (400 MHz, CDCl$_3$) δ 1.19 (9H, s), 4.39 (2H, brs), 6.44 (1H, d, J=2.0 Hz), 7.370-7.502 (5H, m), 7.69 (1H, d, J=2.0 Hz).

D) [(1-phenyl-1H-pyrazol-5-yl)amino]acetonitrile

To a solution of tert-butyl (cyanomethyl)(1-phenyl-1H-pyrazol-5-yl)carbamate (4.38 g) in dichloromethane was added TFA (16.7 g) at room temperature, and the mixture was stirred for 5 hr. The reaction mixture was concentrated under reduced pressure, and adjusted to pH 9-10 with 1N aqueous sodium hydroxide solution. The reaction mixture was extracted with dichloromethane. The extract was washed with saturated brine, dried over anhydrous sodium sulfate, and the solvent was evaporated under reduced pressure. The residue was purified by silica gel column chromatography (dichloromethane/methanol) to give the title compound (1.90 g).

$^1$H-NMR (400 MHz, CDCl$_3$) δ 3.99 (2H, d, J=6.8 Hz), 4.26 (1H, t, J=6.8 Hz), 5.60 (1H, d, J=2.0 Hz), 7.35-7.39 (1H, m), 7.43-7.49 (6H, m).

E) 3,5-dichloro-1-(1-phenyl-1H-pyrazol-5-yl)pyrazin-2(1H)-one

To a solution of [(1-phenyl-1H-pyrazol-5-yl)amino]acetonitrile (1.20 g) in dichlorobenzene (15.0 mL) was added oxalyl chloride (0.922 g) at room temperature, and the mixture was stirred at 100° C. for 12 hr. The reaction mixture was purified by silica gel column chromatography (dichloromethane/methanol) to give the title compound (0.850 g).

$^1$H-NMR (400 MHz, CDCl$_3$) δ 6.73 (1H, d, J=2.0 Hz), 7.32-7.34 (2H, m), 7.40-7.49 (3H, m), 7.87 (1H, d, J=2.0 Hz), 8.22 (1H, s).

F) 5-chloro-3-methoxy-1-(1-phenyl-1H-pyrazol-5-yl)pyrazin-2(1H)-one

To a solution of 3,5-dichloro-1-(1-phenyl-1H-pyrazol-5-yl)pyrazin-2(1H)-one (0.627 g) in methanol (15.0 mL) was added sodium methoxide (0.132 g) at room temperature, and the mixture was stirred for 2 hr. The reaction mixture was concentrated and adjusted to pH 5-6 with 2N hydrochloric acid. The reaction mixture was extracted with dichloromethane. The extract was washed with saturated brine, dried over anhydrous sodium sulfate, and the solvent was evaporated under reduced pressure. The residue was purified by silica gel column chromatography (dichloromethane/methanol) to give the title compound (0.362 g).

$^1$H-NMR (400 MHz, CDCl$_3$) δ 3.99 (1H, s), 6.52 (1H, d, J=2.0 Hz), 6.79 (1H, s), 7.26-7.42 (5H, m), 7.78 (1H, d, J=2.0 Hz).

G) 3-methoxy-5-phenyl-1-(1-phenyl-1H-pyrazol-5-yl)pyrazin-2(1H)-one

To a mixture of 5-chloro-3-methoxy-1-(1-phenyl-1H-pyrazol-5-yl)pyrazin-2(1H)-one (245 mg), tri-tert-butylphosphine (25.0 mg), Pd$_2$(dba)$_3$ (37.0 mg), cesium carbonate (791 mg) and 1,4-dioxane (10.0 ml) was added phenylboronic acid (120 mg) at room temperature. The reaction mixture was heated using a microwave reactor at 95° C. for 1.5 hr. The reaction mixture was concentrated, dichloromethane was added, and the mixture was washed with saturated brine. The extract was dried over anhydrous sodium sulfate, and the solvent was evaporated under reduced pressure. The residue was purified by silica gel column chromatography (petroleum ether/ethyl acetate) to give the title compound (18.0 mg).

MS (ESI+): [M+H]$^+$ 345.2

Example 142

3-(4,4-dimethyl-5-oxo-1-phenyl-4,5-dihydro-1H-imidazol-2-yl)-5-methoxy-1-[3-(trifluoromethyl)phenyl]pyridazin-4(1H)-one A) methyl N-({5-methoxy-4-oxo-1-[3-(trifluoromethyl)phenyl]-1,4-dihydropyridazin-3-yl}carbonyl)-2-methylalaninate A mixture of 5-methoxy-4-oxo-1-[3-(trifluoromethyl)phenyl]-1,4-dihydropyridazine-3-carboxylic acid (300 mg), methyl 2-methylalaninate (134 mg), HOBt (219 mg), WSC (275 mg) and N,N-diisopropylethylamine (0.834 mL) in THF (3.18 mL) was stirred at room temperature for 17 hr, and water was added. The precipitate was collected by filtration, and washed with water and hexane to give the title compound (336 mg).

$^1$H NMR (300 MHz, DMSO-d$_6$) δ 1.51 (6H, s), 3.02 (3H, s), 3.95 (3H, s), 7.85-7.93 (2H, m), 8.20 (1H, d, J=8.4 Hz), 8.24 (1H, s), 8.86 (1H, s), 10.42 (1H, s).

B) N-[1,1-dimethyl-2-oxo-2-(phenylamino)ethyl]-5-methoxy-4-oxo-1-[3-(trifluoromethyl)phenyl]-1,4-dihydropyridazine-3-carboxamide A mixed solution of methyl N-({5-methoxy-4-oxo-1-[3-(trifluoromethyl)phenyl]-1,4-dihydropyridazin-3-yl}carbonyl)-2-methylalaninate (336 mg), 2N aqueous sodium hydroxide solution (1.22 mL) and methanol (2.7 mL) was stirred at room temperature for 5 hr, and the mixture was neutralized with 10% aqueous citric acid solution. The precipitate was collected by filtration, and washed with water to give a solid (301 mg). A mixture of the obtained solid (216 mg), aniline (0.074 mL), HOBt (124 mg), WSC (156 mg) and N,N-diisopropylethylamine (0.472 mL) in THF (1.80 mL) was stirred at room temperature for 17 hr, and water was added. The precipitate was collected by filtration, and washed with water and hexane to give the title compound (142 mg).

$^1$H NMR (300 MHz, DMSO-d$_6$) δ 1.58 (6H, s), 3.97 (3H, s), 7.03 (1H, t, J=7.4 Hz), 7.28 (2H, t, J=8.0 Hz), 7.66 (2H, d, J=7.6 Hz), 7.84-7.91 (2H, m), 8.19 (1H, d, J=8.0 Hz), 8.24 (1H, s), 8.86 (1H, s), 9.70 (1H, s), 10.23 (1H, s).

C) 3-(4,4-dimethyl-5-oxo-1-phenyl-4,5-dihydro-1H-imidazol-2-yl)-5-methoxy-1-[3-(trifluoromethyl)phenyl]pyridazin-4(1H)-one A mixture of N-[1,1-dimethyl-2-oxo-2-(phenylamino)ethyl]-5-methoxy-4-oxo-1-[3-(trifluoromethyl)phenyl]-1,4-dihydropyridazine-3-carboxamide (142 mg), sodium acetate (74 mg) and acetic acid (1 mL) was irradiated with microwave at 120° C. for 2 hr. After cooling to room temperature, to the reaction mixture was added water, and the mixture was extracted with ethyl acetate. The extract was washed with saturated aqueous sodium hydrogen carbonate solution, dried over sodium sulfate, and concentrated under reduced pressure. The residue was purified by silica gel column chromatography (ethyl acetate/methanol) to give the title compound (37 mg).

MS (ESI+): [M+H]+ 457.3

The structures and the like of the compounds of Examples 139-142 are shown in the following Tables.

TABLE 5-1

| Ex. No. | IUPAC name | structure | salt | MS |
|---|---|---|---|---|
| 139 | 3-(1-phenyl-1H-pyrazol-5-yl)-1-[1-(tetrahydro-2H-pyran-4-yl)-piperidin-4-yl]-pyridazin-4(1H)-one | 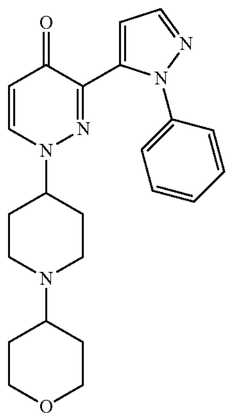 [SMILES: O=c1ccn(C2CCN(C3CCOCC3)CC2)nc1-c1ccnn1-c1ccccc1] | — | 406.3 |
| 140 | 2-phenyl-6-(1-phenyl-1H-pyrazol-5-yl)-4H-thiopyran-4-one | 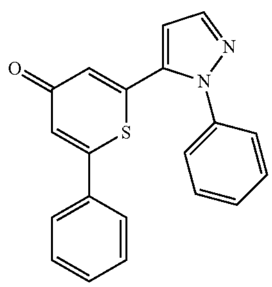 [SMILES: O=c1cc(-c2ccccc2)sc(-c2ccnn2-c2ccccc2)c1] | — | 331.2 |
| 141 | 3-methoxy-5-phenyl-1-(1-phenyl-1H-pyrazol-5-yl)-pyrazine-2(1H)-one | 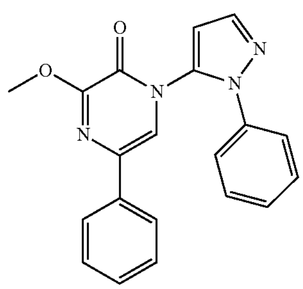 [SMILES: COc1nc(-c2ccccc2)cn(-c2ccnn2-c2ccccc2)c1=O] | — | 345.2 |
| 142 | 3-(4,4-dimethyl-5-oxo-1-phenyl-4,5-dihydro-1H-imidazol-2-yl)-5-methoxy-1-[3-(trifluoromethyl)-phenyl]pyridazin-4(1H)-one | 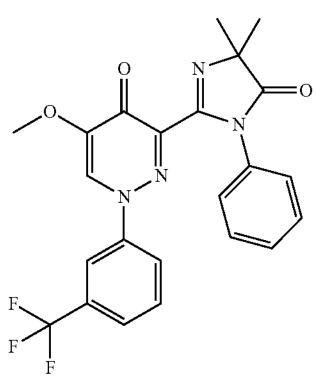 [SMILES: COc1cn(-c2cccc(C(F)(F)F)c2)nc(C2=NC(C)(C)C(=O)N2c2ccccc2)c1=O] | — | 457.3 |

Example 143

1-cyclopropyl-5-methoxy-3-(1-phenyl-1H-pyrazol-5-yl)pyridazin-4(1H)-one

To a solution of 5-methoxy-3-(1-phenyl-1H-pyrazol-5-yl)pyridazin-4-ol (1.0 g) in DMF (20 ml) were added cesium carbonate (2.429 g), bromocyclopropane (0.597 ml) and sodium iodide (0.559 g) at room temperature. The reaction mixture was stirred at 150° C. for 30 hr in an autoclave, allowed to cool to room temperature, and poured into water (100 ml). The mixture was extracted with ethyl acetate, the organic layer was washed with saturated brine, dried over magnesium sulfate, and concentrated to dryness under reduced pressure. The residue was purified by silica gel column chromatography (methanol/ethyl acetate). The fraction containing the title compound was purified again by silica gel column chromatography (NH, methanol/ethyl acetate), and crystallized from methanol/ethyl acetate to give the title compound (15 mg).

MS (ESI+): [M+H]+ 309.1.

Example 144

5-methoxy-3-(1-phenyl-1H-pyrazol-5-yl)-1-(2,2,2-trifluoroethyl)pyridazin-4(1H)-one Under an argon atmosphere, to a solution of 5-methoxy-3-(1-phenyl-1H-pyrazol-5-yl)pyridazin-4-ol (2.0 g) in dehydrated DMF (40 ml) was added 60% NaH in oil (596 mg) while stirring under ice-cooling, and the mixture was stirred at the same temperature for 0.5 hr. Then, trifluoromethanesulfonic acid 2,2,2-trifluoroethyl ester (2.6 g) was added, and the mixture was stirred at room temperature for 18 hr. To the reaction mixture was added methanol, and the mixture was concentrated to dryness under reduced pressure, and the residue was purified by silica gel column chromatography (ethyl acetate/hexane) to give the title compound (1.71 g).

MS (ESI+): [M+H]+ 351.0.

The structures and the like of the compounds of Examples 143 and 144 are shown in the following Tables.

TABLE 6

| Ex. No. | IUPAC name | structure | salt | MS |
|---|---|---|---|---|
| 143 | 1-cyclopropyl-5-methoxy-3-(1-phenyl-1H-pyrazol-5-yl)-pyridazin-4(1H)-one | 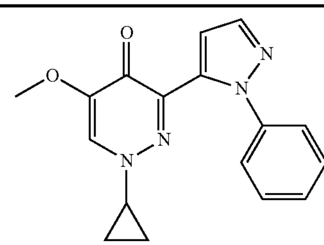 | | 309.1 |
| 144 | 5-methoxy-3-(1-phenyl-1H-pyrazol-5-yl)-1-(2,2,2-trifluoroethyl)-pyridazin-4(1H)-one | 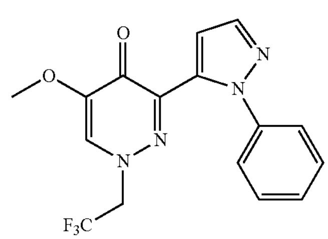 [SMILES: COc1cn(CC(F)(F)F)nc(-c2ccnn2-c2ccccc2)c1=O] | | 351.0 |

Formulation Example 1

| | | |
|---|---|---|
| (1) compound of the Example 1 | 10.0 g | |
| (2) Lactose | 70.0 g | |
| (3) Cornstarch | 50.0 g | |
| (4) Soluble starch | 7.0 g | |
| (5) Magnesium stearate | 3.0 g | |

After 10.0 g of the compound of Example 1 and 3.0 g of magnesium stearate are granulated in 70 ml aqueous solution of soluble starch (7.0 g as soluble starch) and then dried, the resulting mixture is mixed with 70.0 g of lactose and 50.0 g of cornstarch (lactose, cornstarch, soluble starch and magnesium stearate were all products in compliance with Japanese Pharmacopoeia). The mixture is compressed to obtain a tablet.

Experimental Example

PDE10A Enzyme Activity Inhibition Test

Human PDE10A full-length gene was transfected into Sf9 or COS-7 cells, the cells were disrupted and centrifuged, and human PDE10A enzyme was obtained from the residue. The enzyme extracted from Sf9 cells was partially purified using His-tag affinity column. The enzyme was stored at −70° C. until use. The PDE activity was measured using an SPA (Scintillation Proximity Assay) (GE Healthcare). To measure the inhibitory activity of the compound, 10 μL of serially diluted compound was reacted with 20 μL of PDE enzyme in an assay buffer (50 mM HEPES-NaOH, 8.3 mM MgCl$_2$, 1.7 mM EGTA, 0.1% BSA (pH 7.4)) for 30 min at room temperature. The final concentration of DMSO in the reaction mixture was 1 percent. The compounds were evaluated in duplicate in 96-well half-area plates (Corning). To start the reaction, 10 μL of substrate [$^3$H] cGMP (25 and 50 nM; GE Healthcare and PerkinElmer, respectively) was added to 40 μL. After 60 min of reaction at room temperature, yttrium SPA beads containing zinc sulphate were added (6 mg/mL, 20 μL) to terminate the PDE reaction. After standing still for 1 hr, the measurement was performed using a scintillation counter (PerkinElmer) and the PDE10A enzyme activity inhibition rate was calculated. The inhibition rate was calculated based on the control containing enzyme and DMSO as 0% and the control without enzyme as 100%. The results are shown in the following Table.

TABLE 7

| Example No. | A: 50% or more of inhibition rate at 100 nM<br>B: less than 50% of inhibition rate at 100 nM |
|---|---|
| 1 | A |
| 2 | A |
| 11 | A |
| 12 | B |
| 13 | B |
| 14 | B |
| 15 | B |
| 16 | A |
| 17 | B |
| 18 | B |
| 19 | B |
| 20 | B |
| 21 | B |
| 23 | A |
| 25 | A |
| 28 | B |

TABLE 7-continued

| Example No. | A: 50% or more of inhibition rate at 100 nM<br>B: less than 50% of inhibition rate at 100 nM |
|---|---|
| 31 | A |
| 46 | B |
| 49 | B |
| 53 | A |
| 56 | A |
| 58 | A |
| 59 | B |
| 60 | B |
| 61 | A |
| 64 | B |
| 97 | B |
| 98 | A |
| 102 | B |
| 140 | B |
| 141 | B |
| 142 | B |

INDUSTRIAL APPLICABILITY

The medicament of the present invention can be utilized as a medicament for the prophylaxis or treatment of mental diseases such as schizophrenia and the like, and the like.

This application is based on a patent application No. 2010-179430 filed in Japan (filing date: Aug. 10, 2010), the contents of which are incorporated in full herein.

The invention claimed is:
1. A compound represented by formula (1),
$W^1$-$W^2$ (1),
wherein:
(i) $W^1$ is

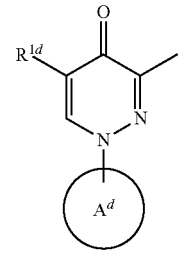

wherein
ring $A^d$ is
(A) $C_{3-8}$ cycloalkane,
(B) a tetrahydronaphthalene ring,
(C) a tetrahydropyridine ring optionally substituted by substituent(s) selected from the group consisting of (a) a $C_{1-6}$ alkyl group, (b) a $C_{1-6}$ alkyl group, (c) a $C_{1-6}$ alkyl group substituted by a phenyl group optionally substituted by a $C_{1-6}$ alkoxy group, and (d) a pyridyl group substituted by a halogen atom,
(D) a piperidine ring optionally substituted by substituent(s) selected from the group consisting of (a) a naphthyl group, (b) a thiazolyl group, (c) a benzofuranyl group, (d) a dihydrobenzofuranyl group, (e) a tetrahydropyranyl group, (f) a thienyl group substituted by a halogen atom or a $C_{1-6}$ alkylcarbonyl group, (g) a methylenedioxyphenyl group substituted by a halogen atom, (h) a benzothiazolyl group optionally substituted by a $C_{1-6}$ alkyl group, (i) a $C_{1-6}$ alkylcarbonyl group, (j) a $C_{1-6}$ alkoxycarbonyl group substituted by a $C_{1-6}$ alkyl group, (k) a $C_{1-6}$ alkyl group optionally substituted by a phenyl group, (l) a phenylcarbonyl group optionally substituted by a halogen atom, (m) a carbamoyl group mono-substituted by a phenyl group, (n) a pyridyl group optionally substituted by substituent(s) selected from the group consisting of a halogen atom, a cyano group, and a $C_{1-6}$ alkyl group substituted by a halogen atom, and (o) a phenyl group optionally substituted by substituent(s) selected from the group consisting of a halogen atom, a $C_{1-6}$ alkyl group optionally substituted by a halogen atom, $C_{1-6}$ alkoxy optionally substituted by a halogen atom, a cyano group, a $C_{1-6}$ alkylcarbonyl group, a $C_{1-6}$ alkylsulfonyl group, a sulfur atom substituted by 1-5 halogen atoms, and an amino group di-substituted by a $C_{1-6}$ alkyl group, or (E) an azetidine ring substituted by substituent(s) selected from the group consisting of (a) a phenyl group, (b) a phenylcarboxy group, (c) a pyridyl group substituted by a $C_{1-6}$ alkyl group substituted by a halogen atom, and (d) a $C_{1-6}$ alkyl group di-substituted by a phenyl group, and
$R^{1d}$ is a hydrogen atom or a $C_{1-6}$ alkoxy group; and
$W^2$ is

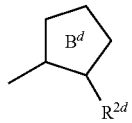

wherein
ring $B^d$ is a pyrazole ring, and
$R^{2d}$ is a phenyl group, or
(ii) $W^1$ is

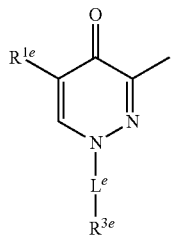

wherein $R^{1e}$ is a $C_{1-6}$ alkoxy group,
$R^{3e}$ is
(a) a $C_{1-6}$ alkyl group substituted by a halogen atom,
(b) a $C_{3-7}$ cycloalkyl group,
(c) a tetrahydropyranyl group,
(d) a piperidyl group,
(e) a tetrahydrofuranyl group,
(f) a pyrrolidyl group,
(g) a morpholinyl group,
(h) a quinolinyl group,
(i) an isoquinolinyl group,
(j) an oxetanyl group substituted by a $C_{1-6}$ alkyl group, (k) a phenyl group optionally substituted by 1 to 3 substituents selected from the group consisting of a $C_{1-6}$ alkyl group substituted by a halogen atom, a $C_{1-6}$ alkoxy group, a $C_{1-6}$ alkoxycarbonyl group, a cyano group, and a phenyl group,
(l) a pyridyl group optionally substituted by 1 to 3 substituents selected from the group consisting of a $C_{1-6}$ alkoxycarbonyl group and a $C_{1-6}$ alkoxy group substituted by a halogen atom, or
(m) a furyl group substituted by substituent(s) selected from the group consisting of a $C_{1-6}$ alkyl group substituted by a halogen atom and a $C_{1-6}$ alkoxycarbonyl group, and $L^e$ is a $C_{1-3}$ alkylene group optionally substituted by an oxo group or a sulfonyl group; and
$W^2$ is

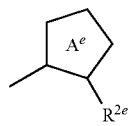

wherein
ring $A^e$ is a pyrazole ring, and
$R^{2e}$ is a phenyl group,
or a pharmaceutically acceptable salt thereof.

2. A pharmaceutical composition comprising the compound or pharmaceutically acceptable salt according to claim 1, and a pharmaceutically acceptable carrier.

3. A method for treating schizophrenia in a mammal, which comprises administering to said mammal an effective amount of the compound according to claim 1, or a pharmaceutically acceptable salt thereof.

4. A compound of 1-(1-Benzyl-1,2,3,6-tetrahydropyridin-4-yl)-5-methoxy-3-(1-phenyl-1H-pyrazol-5-yl)pyridazin-4(1H)-one, or a pharmaceutically acceptable salt thereof.

5. A pharmaceutical composition comprising the compound or pharmaceutically acceptable salt according to claim 4, and a pharmaceutically acceptable carrier.

6. A method for treating schizophrenia in a mammal, which comprises administering to said mammal an effective amount of the compound according to claim 4, or a pharmaceutically acceptable salt thereof.

7. A compound of 2-{4-[5-Methoxy-4-oxo-3-(1-phenyl-1H-pyrazol-5-yl)pyridazin-1(4H)-yl]piperidin-1-yl}pyridine-3-carbonitrile, or a pharmaceutically acceptable salt thereof.

8. A pharmaceutical composition comprising the compound or pharmaceutically acceptable salt according to claim 7, and a pharmaceutically acceptable carrier.

9. A method for treating schizophrenia in a mammal, which comprises administering to said mammal an effective amount of the compound according to claim 7, or a pharmaceutically acceptable salt thereof.

* * * * *